US005643567A

United States Patent [19]
Hung et al.

[11] Patent Number: 5,643,567
[45] Date of Patent: Jul. 1, 1997

[54] METHODS FOR THE SUPPRESSION OF NEU MEDIATED TUMORS BY ADENOVIRAL E1A AND SV40 LARGE T ANTIGEN

[75] Inventors: Mien-Chie Hung; Di-Hua Yu; Angahin Matin; Yujiao Joe Zhang, all of Houston, Tex.

[73] Assignee: Board of Regents, The University of Texas System, Austin, Tex.

[21] Appl. No.: 276,359

[22] Filed: Jul. 15, 1994

Related U.S. Application Data

[63] Continuation-in-part of Ser. No. 162,406, Dec. 3, 1993, which is a continuation-in-part of Ser. No. 70,410, Jun. 4, 1993, which is a continuation-in-part of Ser. No. 621,465, Dec. 4, 1990, abandoned.

[51] Int. Cl.$^6$ .......................... A61K 48/00; F01N 63/00; C12N 15/00
[52] U.S. Cl. .......................... 424/93.2; 424/136; 514/44; 935/55
[58] Field of Search .......................... 514/44; 435/172.3, 435/55, 57, 62; 424/93.2, 93.6

[56] References Cited

U.S. PATENT DOCUMENTS 4,394,448   7/1983   Szoka, Jr. et al. .................. 435/172

FOREIGN PATENT DOCUMENTS

| WO90/15595 | 12/1990 | WIPO . |
| WO93/03769 | 3/1993 | WIPO . |
| WO94/21115 | 9/1994 | WIPO . |

OTHER PUBLICATIONS

Douglas et al., "Modulation of transformation of primary epithelial cells by the second exon of the Ad55 E1A12S gene," *Oncogene*, 6:2093–2103, 1991.
Montell et al., "Complete Transformation by Adenovirus 2 Requires Both E1A Proteins," *Cell*, 36:951–961, 1984.
Offringa et al., "A Novel Function of the Transforming Domain of E1a: Repression of AP-1 Activity," *Cell*, 62:527–538, 1990.
Whyte et al., "Cellular Targets for Transformation by the Adenovirus E1A Proteins," *Cell*, 56:67–75, 1989.
Freedman and Shin, "Use of Nude Mice for Studies on the Tumorigenicity of Animal Cells," *The Nude Mouse in Experimental and Clinical Research*, 1978.
Gazit et al., "Chemo-adoptive immunotherapy of nude nice implanted with human colorectal carcinoma and melanoma cell lines," *Cancer Immunology Immunotherapy*, 35:135–144, 1992.
Inoue, et al., "Consideration of Simultaneous Combination Chemotherapy—Employing a Sensitivity Test in Dunn Osteosarcoma and NR Fibrosarcoma by Intra-Test Contact of Tumor Cell Suspension, and Subcutaneous Inoculation–," *Jpn. Soc. Cancer Ther.* 25(12):2781–2789, 1989.
Yu et al., "Transcriptional Repression of the neu Protooncogene by the Adenovirus 5 E1A Gene Products," *Proc. Natl. Acad. Sci. USA*, 87:4499–4503, 1990.

Teramota et al., "Serum Enzyme Immunoassay Kit for the Detection of c–erbB–2 Oncoprotein," Annual AACI Meeting, Abstract #1446, 1991j.
Zhang et al., "Amplification and Rearrangement of c–erb B Proto–Oncogenes in Cancer of Human Femal Genital Tract," *Oncogene*, 4:985–989, 1989.
Slamon et al., "Studies of the HER–2/neu Proto–Oncogene in Human Breast and Ovarian Cancer," *Science*, 244:707–712, 1989.
Steeg et al., "Altered Expression of NM23, a Gene Associated with Low Tumor Metastatic Potential, during Adenovirus 2 Ela Inhibition of Experimental Metastasis," *Cancer Res.*, 48:6550–6554, 1988.
Smith & Ziff, "The Amino–Terminal Region of the Adenovirus Serotype 5 Ela Protein Performs Two Separate Functions when Expressed in Primary Baby Rat Kidney Cells," *Mol. Cell Biol.*, 8(9):3882–3890, 1988.
Bargmann & Weinberg, "Increased Tyrosine Kinase Activity Associated with the Protein Encoded by the Activated neu Oncogene," *Proc. Natl. Acad. Sci. USA*, 85:5394–5398, 1988.
Pozzatti et al., "The Ela Gene of Adenovirus Type 2 Reduces the Metastatic Potential of ras–Transformed Rat Embryo Cells," *Mol. Cell Biol.*, 8(7):2984–2988, 1988.
Whyte et al., "Two Regions of the Adenovirus Early Region 1A Proteins Are Required for Transformation," *J. Virol.*, 62(1):257–265, 1988.
Egan et al., "Transformation by Oncogenes Encoding Protein Kinases Induces the Metastatic Phenotype," *Science*, 238:202–205, 1987.
Sassone–Corsi & Borrelli, "Promoter Trans–Activation of Protooncogenes c–fos and c–myc, but not c–Ha–ras, by Products of Adenovirus Early Region 1A," *Proc. Natl. Acad. Sci. USA*, 84:6430–6433, 1987.

(List continued on next page.)

*Primary Examiner*—Deborah Crouch
*Attorney, Agent, or Firm*—Arnold, White & Durkee

[57] ABSTRACT

Disclosed are methods and compositions for the suppression of expression of the neu oncogene, as well as suppression of neu oncogene-mediated transformation, tumorigenesis and metastasis. The method disclosed involves introduction of adenovirus early 1A gene (the E1A gene) products, or the large T antigen (the LT gene product), or both into affected cells. These products, which are preferably introduced by transfection of the E1A gene into affected cells, serve to suppress neu gene expression as measured by a reduction of p185 expression. Furthermore, the E1A gene products surprisingly serve to suppress the oncogenic phenotype, as indicated by a reduction in cell growth, growth in soft agar, as well as tumorigenic and metastatic potential in vivo. The inventors propose that E1A gene products, LT gene products or derivatives therefrom, may ultimately be employed a treatment modalities for neu-mediated cancers, such as cancers of the female genital tract and breast. The inventors also propose methods of transfecting cells with either the E1A or the LT gene products using adenoviral vectors or liposomes.

22 Claims, 40 Drawing Sheets

OTHER PUBLICATIONS

Kraus et al., "Overexpression of the EGF Receptor–Related Proto–Oncogene erbB–2 in Human Mammary Tumor Cell Lines by Different Molecular Mechanisms," *EMBO J.*, 6(3):605–610, 1987.

Slamon et al., "Human Breast Cancer: Correlation of Relapse and Survival with Amplification of the HER–2/neu Oncogene," *Science*, 235:177–182, 1987.

Pozzatti et al., "Primary Rat Embryo Cells Transformed by One or Two Oncogenes Show Different Metastatic Potentials," *Science*, 232:223–227, 1986j.

Stern et al., "p185, a Product of the neu Proto–Oncogene, Is a Receptorlike Protein Associated with Tyrosine Kinase Activity," *Mol. Cell Biol.*, 6(5):1729–1740, 1986.

Schecter et al., "The neu Gene: An erbB–Homologous Gene Distinct from and Unlinked to the Gene Encoding the EGF Receptor," *Science*, 229:976–978, 1985.

Brunet et al., "Concentration Dependence of Transcriptional Transactivation in Inducible E1A–Containing Human Cells," *Mol. Cell. Bio.*, 8(11):4799–4807 (1988).

Felgner et al., "Gene Therapeutics: The Direct Delivery of Purified Genes in vivo and Their Application as Drugs, Without the Use of Retroviruses, Is Discussed," *Nature*, 349:351–352 (1991).

Frisch et al., "Adenovirus E1A Represses Protease Expression and Inhibits Metastasis of Human Tumor Cells," *Oncogene*, 5:75–83 (1990).

Harlow et al., "Monoclonal Antibodies Specific for Adenovirus Early Region 1A Proteins: Extensive Heterogeneity in Early Region 1A Products," *J. of Virology*, 55(3):533–546 (1985).

Hearing et al., "Sequence–Independent Autoregulation of the Adenovirus Type 5 E1A Transcription Unit," *Mol. Cell. Bio.*, 5(11):3214–3221 (1985).

Nabel et al., "Site–Specific Gene Expression in Vivo by Direct Gene Transfer into the Arterial Wall,"0 *Science*, 249:1285–88 (1990).

Moran et al., "Multiple Functional Domains in the Adenovirus E1A Gene," *Cell*, 48:177–178 (1987).

Ruley, "Adenovirus Early Region 1A Enables Viral and Cellular Transforming Genes to Transform Primary Cells in Culture," *Nature*, 304:602–606 (1983).

Senear et al., "Morphological Transformation of Established Rodent Cell Lines by High–Level Expression of the Adenvirus Type 2 E1a Gene," *Mol. Cell. Bio.*, 6(4):1253–1260 (1986).

Suen et al., *Breast Cancer Research and Treatment*, 14(1):Abstract 213 (1989).

Whyte et al., "Association between an Oncogene and an Anti–Oncogene; The Adenovirus E1A Proteins Bind to the Retinoblastoma Gene Product," *Nature*, 334:124–129 (1988).

Yu et al., "Adenovirus Type 5 E1A Gene Products Act as Transformation Suppressors of the neu Oncogene," *Mol. Cell. Bio.*, 11(3):1745–1750 (1991).

Zhou, et al., "A Retrovirus Vector which Transduces a Functional Estrogen Receptor Gene at High Efficiency," *Mol. Endocrinology*, 3(7):1157–1164 (1989).

Zhau, et al., *Chemical Abstracts*, 114(21):205–Abstract No. 114:200732Z (1991).

Bargmann et al., "Multiple Independent Activations of the neu Oncogene by a Point Mutation Altering the Transmembrane Domain of p185," *Cell*, 45:649–657, 1986.

Bargmann et al., "The neu Oncogene Encodes an Epidermal Growth Factor Receptor–Related Protein," *Nature*, 319:226–230, 1986.

Berk and Sharp, "Structure of the Adenovirus 2 Early mRNAs," *Cell*, 14:695–711, 1978.

Fung et al., "Activation of the Cellular Oncogene c–erbB by LTR Insertion: Molecular Basis for Induction of Erythroblastosis by Avian Leukosis virus," *Cell*, 33:357–368, 1983.

Berk, "Adenovirus Promoters and E1A Transactivation," *Ann. Rev. Genet.*, 20:45–79, 1986.

Coussens et al., "Tyrosine Kinase Receptor with Extensive Homology to EGF Receptor Shares Chromosomal Location with neu Oncogene," *Science*, 230:1132–1139, 1985.

Downward et al., "Close Similarity of Epidermal Growth Factor Receptor and v–erb–B Oncogene protein Sequence," *Nature*, 307:521–527, 1984.

Haley et al., "Transformation Properties of Type 5 Adenovirus Mutants that Differentially Express the E1A Gene Products," *Proc. Natl. Acad. Sci. USA*, 81:5734–5738, 1984.

Houweling et al., "Partial Transformation of Primary Rat Cells by the Leftmost 4.5% Fragment of Adenovirus 5 DNA," *J. Virology*, 105:537–550, 1980.

Hung et al., "Amplification of the Proto–neu Oncogene Facilitates Oncogenic Activation by a Single Point Mutation," *Proc. Natl. Acad. Sci. USA*, 86:2545–2548, 1989.

Hung, "The neu Proto–Oncogene and Breast Cancer," *Cancer Bull.*, 40:300–303, 1988.

Hung et al., "Modecular Cloning of the neu Gene: Absence of Gross Structural Alteration in Oncogenic Alleles," *Proc. Natl. Acad. Sci. USA*, 83:261–264, 1986.

Land et al., "Cellular Oncogenes and Multistep Carcinogenesis," *Science*, 222:771–776, 1983.

Lupu et al., "Direct Interaction of a Ligand for the erbB2 Oncogene Product with the EGF Receptor and p185$^{erbB2}$," *Science*, 249:1552–1554, 1990.

Müller et al., "Differential Expression of Cellular Oncogenes During Pre– and Postnatal Development of the Mouse," *Nature*, 299:640–644, 1982.

Schechter et al., "The neu Oncogene: An erb–B–Related Gene Encoding a 185,000–$M_r$ Tumour Antigen," *Nature*, 312:513–516, 1984.

Semba et al., "A v–erbB–Related Protooncogene, c–erbB–2, Is Distinct from the c–erbB–1Epideral Growth Factor–Receptor Gene and Is Amplified in a Human Salivary Gland Adenocarcinoma," *Proc. Natl. Acad. Sci. USA*, 82:6497–6501, 1985.

Shih et al., "Transforming Genes of Carcinomas and Neuroblastomas Introduced into Mouse Fibroblasts," *Nature* 290:261–264, 1981.

Wallich et al., "Abrogation of Metastatic Properties of Tumour Cells by de novo Expression of H–2K Antigens Following H–2 Gene Transfection," *Nature*, 315:301–305, 1985.

Yamamoto et al., "Similarity of Protein Encoded by the Human c–erb–B–2 Gene to Epidermal Growth Factor Receptor," *Nature*, 319:230–232, 1986.

Yarden and Weinberg, "Experimental Approaches to Hypothetical Hormones: Detection of a Candidate Ligand of the neu Protooncogene," *Proc. Natl. Acad. Sci. USA*, 86:3179–3183, 1989.

Buchman et al., Appendix A: The SV40 Nucleotide Sequence, *DNA Tumor Viruses*, 799–813.

Felgner, P.K., and Ringold, G.M., Cationic liposome–mediated transfection, *Nature*, 337:387–388, 1989.

Figge et al., Prediction of similar Transforming Regions in Simian Virus 40 Large T, Adenovirus E1A, and myc Oncoproteins, *Journal of Virology,* 62:(5)1814–1818, 1988.

Goo, X., and Huang, L., A Novel Cationic Liposome Reagent for Efficient Transfection of Mammalian Cells, *Biochemical and Biophysical Research Communication,* 179:(1)280–285, 1991.

Kalderon, D., and Smith, A.E., In Vitro Mutagenesis of a Putative DNA Binding Domain of SV40 Large–T, *Virology,* 139:109–137, 1984.

Lehvaslaiho et al., A chimeric EGF–R–neu proto–oncogene allows EGF to regulate neu tyrosine kinase and cell transformation, *EMBO Journal,* 8:(1)159–166, 1989.

Leibiger et al., Expression of exogenous DNA in rat liver cells after liposome–mediated transfection in vivo, *Biochemcical and Biophysical Research Communications,* 174:(3)1223–1231, 1991.

Nicolau et al., Liposomes as Carriers for Gene Transfer in Vivo, *Biology Cell,* 47:121–130, 1983.

Nicolau et al., Liposomes for Gene Transfer and Expression in Vivo, *Colloids and Surfaces,* 14:325–337, 1985.

Nicolau et al., Liposomes as Carriers for in Vivo Gene Transfer and Expression, *Methods in Enzymology,* 149:157–177, 1987.

Rustgi et al., Amino–terminal domains of c–myc and N–myc proteins mediate binding to the retinoblastoma gene product, *Nature,* 352:541–544, 1991.

Suen, T., and Hung, M., Multiple cis–and trans–Acting Elements Involved in Regulation of the neu Gene, *Molecular and Cellular Biology,* 10:(12)6306–6315, 1990.

Toose, J., Comparison of the Regions of Polyoma Virus and SV40 That Code for Small and Large T Antigens, *Molecular Biology of Tumor Viruses,* 2nd ed. Part 2, 857–861.

Tzeng et al., Breast cancer formation in transgenic animal induced by the whey acidic protein SV40 T antigen (WAP–SV–T) hybrid gene, *Oncogene,* 8:1965–1971, 1993.

Weinberg, R.A., The Action of Oncogenes in the Cytoplasm and Nucleus, *Science,* 230–770–776, 1985.

Wolff et al., Differential Effects of the Simian Virus 40 Early Genes on Mammary Epithelial Cell Growth, Morphology, and Gene Expression, *Experimental Cell Research,* 202:67–76, 1992.

Yu et al., Enhanced c–erbB–2/neu Expression in Human Ovarian Cancer Cells Correlates with More Severe Malignancy That Can Be Suppressed by E1A[1]*Cancer Research,* 53:891–898, 1993.

Hung, et al., "Transcriptional Repression of the HER–2/neu Protooncogene by Transforming Oncogenes from DNA Tumor Virus," Proceedings of the American Association for Cancer Research, Washington, dc, 31:13, Abstract No. 74.

Matin and Hung, "Negative Regulation of the Neu Promoter by the SV40 Large T Antigen," *Cell Growth & Differentiation,* 4:1051–1056, Dec. 1993.

Shin, "Use of Nude Mice for Tumorigenicity Testing and Mass Propagation," *Methods in Enzymology,* 58:370–379, 1979.

Vousden and Jat, "Functional Similarity between HPV16E7, SV40 Large T and Adenovirus E1a Proteins," *Oncogene,* 4:153–158, 1989.

Yu et al., "Enhanced c–erbB–2/neu Expression in Human Ovarian Cancer Cells Correlates with More Severe Malignancy That Can Be Suppressed by E1A," 53:891–898, 1993.

Matin, "Regulation of neu gene expression by the simian virus 40 large T antigen and tumor suppressors Rb and p53," *Diss. Abstr. Int. B,* 54(5):2365, 1993.

Hung et al., "Transcriptional repression of the HER–2/neu protooncogene by transforming oncogenes from DNA tumor virus," *Proc. AM. Assoc. Cancer Res., 81st Annual Meeting,* 31:13, Mar. 1990.

Tumorigenicity assay

| Cell Line | Time to develop tumors (No. of tumors/no. of injection) | | | | | Tumor volume at 16 days (mm³) |
|---|---|---|---|---|---|---|
| | 8 | 12 | 14 | 20 | 26 (days) | |
| B104-1-1 | 6/6 | 6/6 | 6/6 | 6/6 | 6/6 | 8240±203 |
| NIH3T3 | 0/6 | 0/6 | 0/6 | 0/6 | 0/6 | N.D. |
| N-E1A-1 | 0/6 | 0/6 | 0/6 | 0/6 | 0/6 | N.D. |
| B-E1A-1 | 0/6 | 0/6 | 0/6 | 5/6 | 6/6 | N.D. |
| B-E1A-2 | 0/6 | 2/6 | 6/6 | 6/6 | 6/6 | 216±53 |
| B-E1A-3 | 0/6 | 6/6 | 6/6 | 6/6 | 6/6 | 481±74 |

FIG. 9A

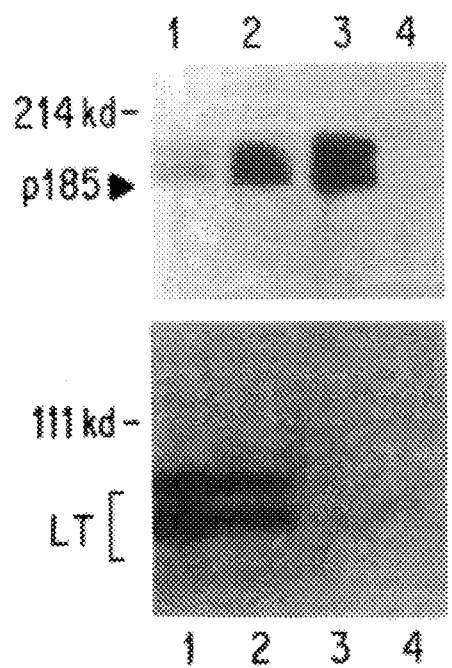
FIG.15A
FIG.15B
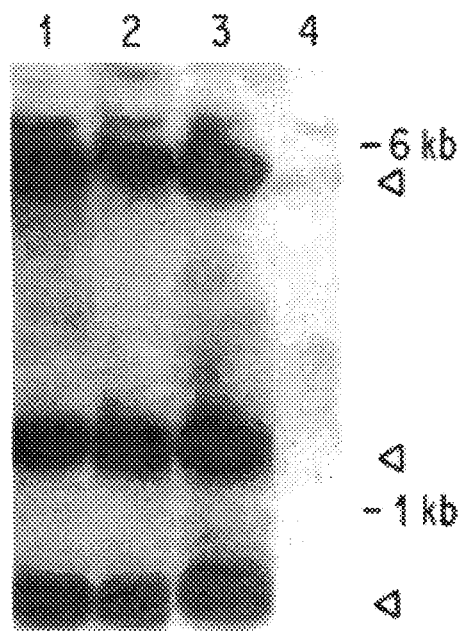
FIG.15C

METHODS FOR THE SUPPRESSION OF NEU MEDIATED TUMORS BY ADENOVIRAL E1A AND SV40 LARGE T ANTIGEN

The present application is a continuation-in-part of U.S. patent application Ser. No. 08/162,406 filed Dec. 3, 1993 which was a continuation-in-part of U.S. Ser. No. 08/070,410, filed Jun. 4, 1993, which was a continuation-in-part of U.S. Ser. No. 07/621,465, filed Dec. 4, 1990, abandoned. The entire text and figures of each of the above-referenced disclosures are specifically incorporated herein by reference without disclaimer.

The U.S. Government has rights in this invention pursuant to N.I.H. Grants CA 58880, CA 60856 and CA 45265.

BACKGROUND OF THE INVENTION

A. Field of the Invention

The present invention relates to methodology and associated genetic constructs for the suppression of oncogene-mediated, transformation, tumorigenesis and metastasis. In particular, this invention relates to the suppression of oncogenesis that is mediated by the HER-2/c-erb B-2/neu oncogene, an oncogene which has been correlated with a poor prognosis of breast and ovarian carcinoma in humans.

B. Background of the Related Art

During the last decade, a number of human malignancies have been discovered to be correlated with the presence and expression of "oncogenes" in the human genome. More than twenty different oncogenes have now been implicated in tumorigenesis, and are thought to play a direct role in human cancer (Weinberg, 1985). Many of these oncogenes apparently evolve through mutagenesis of a normal cellular counterpart, termed a "proto-oncogene", which leads to either an altered expression or activity of the expression product. There is considerable data linking proto-oncogenes to cell growth, including their expression in response to certain proliferation signals (see, e.g., Campisi et al., 1983) and expression during embryonic development (Muller et al., 1982). Moreover, a number of the proto-oncogenes are related to either a growth factor or a growth factor receptor.

The c-erbB gene encodes the epidermal growth factor receptor (EGFr) and is highly homologous to the transforming gene of the avian erythroblastosis virus (Downward et al., 1984). The c-erbB gene is a member of the tyrosine-specific protein kinase family to which many proto-oncogenes belong. The c-erbB gene has recently been found to be similar, but distinct from, an oncogene referred to variously as c-erbB-2, HER-2 or neu oncogene (referred to herein simply as the neu oncogene), now known to be intimately involved in the pathogenesis of cancers of the human female breast and genital tract.

The neu oncogene, which encodes a p185 tumor antigen, was first identified in transfection studies in which NIH 3T3 cells were transfected with DNA from chemically induced rat neuroglioblastomas (Shih et al., 1981). The p185 protein has an extracellular, transmembrane, and intracellular domain, and therefore has a structure consistent with that of a growth factor receptor (Schechter et al., 1984). The human neu gene was first isolated due to its homology with v-erbB and EGF-r probes (Senba et al., 1985).

Molecular cloning of the transforming neu oncogene and its normal cellular counterpart, the neu proto-oncogene, indicated that activation of the neu oncogene was due to a single point mutation resulting from one amino acid change in the transmembrane domain of the neu encoded p185 protein (Bargmann et al., 1986; Hung et al., 1989).

The neu oncogene is of particular importance to medical science because its presence is correlated with the incidence of cancers of the human breast and female genital tract. Moreover, amplification/overexpression of this gene has been directly correlated with relapse and survival in human breast cancer (Slamon et al., 1987). Therefore, it is an extremely important goal of medical science to evolve information regarding the neu oncogene, particularly information that could be applied to reversing or suppressing the oncogenic progression that seems to be elicited by the presence or activation of this gene. Unfortunately, little has been previously known about the manner in which one may proceed to suppress the oncogenic phenotype associated with the presence of oncogenes such as the neu oncogene.

An extensive body of research exists to support the involvement of a multistep process in the conversion of normal cells to the tumorigenic phenotype (see, e.g., Land et al., 1983). Molecular models supporting this hypothesis were first provided by studies on two DNA tumor viruses, adenovirus and polyomavirus. In the case of adenovirus, it was found that transformation of primary cells required the expression of both the early region 1A (E1A) and 1B (E1B) genes (Houweling et al., 1980). It was later found that the E1A gene products could cooperate with middle T antigen or with activated H-ras gene to transform primary cells (Ruley, 1985). These observations suggested that the involvement of multiple functions in the transformation process, and that various oncogenes may express similar functions on a cellular level.

The adenovirus E1A gene codes for several related proteins to which a number of interesting properties have been attributed. In addition to its ability to complement a second oncogene in transformation, a closely related function allows E1A to immortalize primary cells (Ruley; 1985). For example, introduction of E1A gene products into primary cells has been shown to provide these cells with an unlimited proliferative capacity when cultured in the presence of serum.

Another interesting action of E1A function is so-called "trans-activation", wherein E1A gene products stimulate transcription from a variety of viral and cellular promoters, including the adenovirus early and major late promoter. However, trans-activation is not universal for all promoters. In some instances, E1A causes a decrease in transcription from cellular promoters that are linked to enhancer elements (Haley et al., 1984). Recently, it has been shown that exogenously added E1A gene can reduce the metastatic potential of ras-transformed rat embryo fibroblast cells by activating the cellular NM23 gene that is associated with a lower metastatic potential (Pozzatti et 1988; Wallich et al., 1985).

The E1A gene products are referred to as the 13S and 12S products, in reference to the sedimentation value of two mRNAs produced by the gene. These two mRNAs arise through differential splicing of a common precursor, and code for related proteins of 289 and 243 amino acids, respectively. The proteins differ internally by 46 amino acids that are unique to the 13S protein. A number of E1A protein species can be resolved by PAGE analysis, and presumably arise as a result of extensive posttranslational modification of the primary translation products (Harlow et al., 1985).

Another viral oncoprotein, the SV 40 large T antigen (LT) shares structural and functional homology to E1A and c-myc (Figge et al., 1988). LT, E1A and c-myc have transforming domains which share amino acid sequence homology and similar secondary structure (Figge et al., 1988). All three proteins complex with the tumor suppressor, retinoblastoma gene product (Rb) (Whyte et al., 1988, DeCaprio et al., 1988, Rustgi et al., 1991), and the Rb binding domains of LT and E1A coincide with their transforming domains. Based on this similarity, it has been thought that LT and E1A transform cells by binding cellular Rb and abrogating its tumor suppressor function. LT, E1A and c-myc are also grouped as immortalization oncogenes as determined by the oncogene cooperation assay using rat embryo fibroblasts (Weinberg, 1985).

In spite of the similarity between the Rb binding domains of LT and E1A, the two proteins differ substantially in other regards. In fact, there is apparently only a short equivalent stretch of acidic amino acids (Figge et al., 1988). This stretch lies between amino acids 106–114 in LT and amino acids 121–139 in E1A. The large T antigen is encoded by the simian virus 40, a member of the polyoma virus family. In contrast, E1A is encoded by adenovirus 5 virus, which is a member of the adenovirus family. LT is 708 amino acids long, while E1A is substantially shorter at 298 amino acids. LT has been observed to bind directly to certain DNA sequences, however, E1A has not. LT binds with the tumor suppressors Rb and also with p53. E1A complexes with Rb but not with p53. E1A has been shown to induce apoptosis in cells, this has not been demonstrated for LT.

Further, LT is an apparent anomaly in the scheme of oncogenic classification. Oncogenes are typically classified as being cytoplasmic or nuclear oncogenes. However, LT, through the actions of a single protein, is able to introduce "nuclear" characteristics such as immortalization and "cytoplasmic" characteristics such as anchorage independence in cells (Weinberg, 1985). LT antigen can be found in both the nucleus and at the plasma membrane, and mutations that inhibit the transport of LT into the nucleus appear to reduce its immortalizing ability while leaving intact its effect on anchorage independence and its ability to transform already immortalized cells. Consequently, this oncogene is considered to be a member of both the nuclear and cytoplasmic oncogenic classes, since it sends its gene product to do work at two distinct cellular sites (Weinberg, 1985). In contrast, E1A is known as a nuclear oncogene only.

Despite advances in identifying certain components which contribute to the development of malignancies, it is clear that the art still lacks effective means of suppressing carcinogenesis. For example, there is as yet no particularly successful way of suppressing neu oncogene activation or the development of various cancers, such as those of the breast and genital tract, which are associated with this molecular event.

SUMMARY OF THE INVENTION

The present invention seeks to overcome these and other drawbacks inherent in the prior art by providing methods for the suppression of neu-mediated oncogenesis. Certain aspects of the present invention relate to the inventors' surprising discovery that, in contrast to previous characterizations of the E1A gene and the LT gene as being involved in promoting transformation, the E1A and LT gene products can actually serve to suppress not only the expression of the neu oncogene, but suppress the oncogenic phenotype which accompanies neu oncogene activation. Interestingly, these two gene products do so through different mechanisms. It is proposed that this exciting discovery opens the door to novel approaches to the treatment of neu oncogene-mediated cancers, as well as an improved understanding of the regulation of this oncogene in particular and the oncogenic phenotype in general.

The present invention thus arises out of the inventors' surprising discovery that products of the adenovirus E1A gene, a gene that is itself known to serve as an oncogene, can be effectively employed to suppress the transforming capability of the neu oncogene. Accordingly, the invention can be characterized in a general sense as relating to a method of suppressing neu oncogene-mediated transformation of a cell, which method includes introducing an E1A gene product into such a cell in a manner that is effective to suppress an oncogenic phenotype, as indicated by a reduction in transforming, tumorigenic or metastatic potential of the cell.

The invention also arises out of the inventors' surprising showing that introduction of LT antigen into cells leads to a significant decrease in the expression of neu encoded p185. LT, like E1A and c-myc, represses the upstream regulatory sequences of neu. However, LT represses a different region of the neu regulatory sequences compared to E1A and c-myc, suggesting LT affects neu expression through a different pathway.

Previous studies had shown that the tumor suppressor, Rb, represses the activity of the neu promoter (Yu et al., 1992). Since Rb was known to complex LT, the inventors investigated whether LT-Rb complex might affect the LT-mediated neu repression. Surprisingly, the inventors found that the Rb binding domain of LT is not required for its function in repressing neu promoter, indicating LT can repress neu expression without binding Rb. This indicates that LT and E1A are not acting in the same manner. Moreover, a non-transforming mutant of LT (K1), capable of repressing the transforming activity of neu, has been discovered. Repression of neu by LT is, therefore independent of its ability to complex Rb and to transform cells. Therefore, although E1A, LT and c-myc share a common domain for transformation (Figge et al., 1988) and Rb binding (Whyte et al., 1988; DeCaprio et al., 1988; Rustigi et al., 1991), this domain, at least in LT, is not required for repression of the neu promoter. This supports the observation that LT represses neu via a different pathway compared to E1A and c-myc.

These results also show that K1, a LT mutant which is defective for both Rb binding and transformation, can function as a transformation suppressor of the activated neu oncogene. This finding allows for the development of therapeutic agents that down-modulate neu expression in human cancers.

In general, in that it is proposed that the E1A gene products and LT are directly responsible for the observed suppressions of the oncogenic phenotype, it is believed that the objects of the invention may be achieved by introduction of E1A gene products or LT intracellularly in any convenient manner, including, for example, virus mediated gene transfer, DNA transfection via calcium phosphate or liposome methods, and even direct introduction of gene products by microinjection. It is proposed that methods such as these will work adequately, e.g., where one is seeking to study neu oncogene suppression. However, where a treatment regimen is contemplated it will likely be necessary to introduce the selected E1A gene product or LT by intracellular introduction of a DNA segment which encodes the particular domain of the E1A protein or LT that is required for repression of neu.

In any event, since the E1A gene products have been extensively characterized, and the gene itself has been cloned (see, e.g., Berk et al., 1978), the starting materials, i.e., the E1A products and gene, are readily available to those of skill in the art who desire to practice the invention.

LT is also characterized and the gene has been cloned. The entire SV40 nucleotide sequence is disclosed in the book *Molecular Biology of Tumor Viruses*, Part 2, 2d. ed., Tooze, J., Cold Spring Harbor Laboratory, Cold Spring Harbor, N.Y. (1981), Appendix A, pgs. 799–813. In addition to the genomic sequence, *Molecular Biology of Tumor Viruses* contains a map of SV40 landmarks including the location of the large T antigen within the SV40 genome [pg. 813]. The references Fiers et al., 1978 and Reddy et al., 1978 also report the genetic sequences of SV40. The amino acid sequence of LT can be found in *Molecular Biology of Tumor Viruses*, pgs. 854 and 857–861. Various mutant of native LT have been described. For example, Kalderon et al. (1984) describe many LT mutations, which were the result of deletion and point mutations of the native LT gene. The relevant amino acid sequences of each LT mutant reported in Kalderon et al. are contained in Table 2 of that reference. By combining the information in Kalderon et al. (1984) with the sequence information for native LT contained in *Molecular Biology of Tumor Viruses*, the sequence for any of these mutants can be determined. All of the genomic and amino acid sequences of native LT and LT mutants contained in the references cited in this paragraph are incorporated by reference in this specification.

Introduction of Gene Products

Where the gene itself is employed to introduce the gene products, a convenient method of introduction will be through the use of a recombinant vector which incorporates the desired gene, together with its associated control sequences. The preparation of recombinant vectors is well known to those of skill in the art and described in many references, such as, for example, Sambrook et al. (1989), specifically incorporated herein by reference.

In vectors, it is understood that the DNA coding sequences to be expressed, in this case those encoding the neu-suppressing gene products, are positioned adjacent to and under the control of a promoter. It is understood in the art that to bring a coding sequence under the control of such a promoter, one generally positions the 5' end of the transcription initiation site of the transcriptional reading frame of the gene product to be expressed between about 1 and about 50 nucleotides "downstream" of (i.e., 3' of) the chosen promoter. One may also desire to incorporate into the transcriptional unit of the vector an appropriate polyadenylation site (e.g., 5'-AATAAA-3'), if one was not contained within the original inserted DNA. Typically, these poly A addition sites are placed about 30 to 2000 nucleotides "downstream" of the coding sequence at a position prior to transcription termination.

While use of the control sequences of the specific gene (i.e., the E1A promoter for E1A and the LT promoter for LT) will be preferred, there is no reason why other control sequences could not be employed, so long as they are compatible with the genotype of the cell being treated. Thus, one may mention other useful promoters by way of example, including, e.g., an SV40 early promoter, a long terminal repeat promoter from retrovirus, an actin promoter, a heat shock promoter, a metallothionein promoter, and the like.

For introduction of the E1A or LT gene, it is proposed that one will desire to preferably employ a vector construct that will deliver the desired gene to the affected cells. This will, of course, generally require that the construct be delivered to the targeted tumor cells, for example, breast, genital, or lung tumor cells. It is proposed that this may be achieved most preferably by introduction of the desired gene through the use of a viral vector to carry either the E1A or LT sequences to efficiently infect the tumor, or pretumorous tissue. These vectors will preferably be an adenoviral, a retroviral, a vaccinia viral vector or adeno-associated virus. These vectors are preferred because they have been successfully used to deliver desired sequences to cells and tend to have a high infection efficiency.

Commonly used viral promoters for expression vectors are derived from polyoma, cytomegalovirus, Adenovirus 2, and Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the Hind III site toward the Bgl I site located in the viral origin of replication. Further, it is also possible, and often desirable, to utilize promoter or control sequences normally associated with the desired gene sequence, provided such control sequences are compatible with the host cell systems.

The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

A particularly desirable vector, at least as a starting point, is the E1A containing retroviral vector, termed pSVXE1A-G, described by Robert et al., 1985. This vector comprises the E1A gene which has been brought under the control of the SV-40 early promoter. For LT expression, the pZ189 (driven by the SV-80 promoter) and the pVU-O vectors both contain LT. LT mutants are contained in, for example, pK1 and pK7 as well as other vectors described by Kalderon et al. 1984. The inventors propose that these constructs could either be used directly in the practice of the invention, or could be used as a starting point for the introduction of other more desirable promoters such as those discussed above.

A preferred method of introducing the E1A gene to an animal is to introduce a replication-deficient adenovirus containing the E1A gene. An example of such an adenovirus is Ad. E1A(+). Since adenovirus is a common virus infecting humans in nature and the E1A gene is a gene that is present in native adenovirus, the use of a replication deficient E1A virus to introduce the gene may efficiently deliver and express E1A into target cells. The replication-deficient E1A virus made by E1B and E3 deletion also avoids the viral reproduction inside the cell and transfer to other cells and infection of other people, which means the viral infection activity is shut down after it infects the target cell. The E1A gene still is expressed inside the cells. Also, unlike retrovirus, which can only infect proliferating cells, adenovirus is able to transfer the E1A gene into both proliferating and non-proliferating cells. Further, the extrachromosomal location of adenovirus in the infected cells decreases the chance of cellular oncogene activation within the treated animal. While the wild-type adenovirus may be used directly to transfer the E1A gene into HER-2/neu expressing cancer cells, wild-type virus will produce large amounts of adenovirus in the human body and therefore might cause potential side effects due to the replication competent nature of the wild type adenovirus. It is therefore an advantage to use the replication-deficient adenovirus such as E1B and E3 deletion mutant Ad. E1A(+) to prevent such side effects. In fact, many modifications in the native adenovirus will result in a modified virus that will be useful for the purpose of the invention. Further modification of adenovirus such as E2A deletion may improve the E1A expression efficiency and reduce the side effects. The only requirement of a native or modified adenovirus is that it should express an E1A gene in order to have the utility of the invention.

Introduction of the adenovirus containing the E1A gene into a suitable host is typically done by injecting the virus contained in a buffer.

One manner in which the E1A gene that is contained in an adenovirus can be used is by introducing an LT gene product into such a cell as part of the same treatment method. The LT gene product can be an LT mutant, especially a nontransforming mutant such as K1. Such introduction can typically involve the introduction of an LT gene. In some preferred methods, the LT gene can be introduced by the use of an adenovirus that contains both the E1A gene and the LT gene. In this case, adenovirus is a preferably a replication-deficient adenovirus such as the Ad.E1A(+) adenovirus. However, the introduction of the LT gene can be by any manner described in this specification or known to those of skill in the art such as vital, plasmid, retroviral vectors or liposomes.

The present invention also provides particularly useful methods for introducing neu-suppressing gene products into cells. One method of in vivo gene transfer which can lead to expression of genes transfected into cells involves the use of liposomes. Liposomes can be used for both in vitro and in vivo transfection. Liposome-mediated gene transfer seems to have great potential for certain in vivo applications in animals (Nicolau et al., 1987). Studies have shown that intravenously injected liposomes are taken up essentially in the liver and the spleen, by the macrophages of the reticuloendothelial system. The specific cellular sites of uptake of injected liposomes appears to be mainly spleen macrophages and liver Kupffer cells. Intravenous injection of liposomes/DNA complexes can lead to the uptake of DNA by these cellular sites, and result in the expression of a gene product encoded in the DNA (Nicolau, 1983).

The inventors contemplate that neu-suppressing gene products can be introduced into cells using liposome-mediated gene transfer. It is proposed that such constructs can be coupled with liposomes and directly introduced via a catheter, as described by Nabel et al. (1990). By employing these methods, the neu-suppressing gene products can be expressed efficiently at a specific site in vivo, not just the liver and spleen cells which are accessible via intravenous injection. Therefore, this invention also encompasses compositions of DNA constructs encoding a neu-suppressing gene product formulated as a DNA/liposome complex and methods of using such constructs.

Liposomal transfection can be via liposomes composed of, for example, phosphatidylcholine (PC), phosphatidylserine (PS), cholesterol (Chol), N-[1-(2,3-dioleyloxy) propyl]-N,N-trimethylammonium chloride (DOTMA), dioleoylphosphatidylethanolamine (DOPE), and/or 3β[N-(N'N'-dimethylaminoethane)-carbarmoyl cholesterol (DC-Chol), as well as other lipids known to those of skill in the art. Those of skill in the art will recognize that there are a variety of liposomal transfection techniques which will be useful in the present invention. Among these techniques are those described in Nicolau et al., 1987, Nabel et al., 1990, and Gao et al., 1991. The inventors have had particular success with liposomes comprising DC-Chol. More particularly, the inventors have had success with liposomes comprising DC-Chol and DOPE which have been prepared following the teaching of Gao et al., 1991, in the manner described in the Preferred Embodiments Section. The inventors also anticipate utility for liposomes comprised of DOTMA, such as those which are available commercially under the trademark Lipofectin™, from Vical, Inc., in San Diego, Calif.

Liposomes may be introduced into contact with cells to be transfected by a variety of methods. In cell culture, the liposomes can simply be dispersed in the cell culture solution. For application in vivo, liposomes are typically injected. Intravenous injection allow liposome-mediated transfer of DNA complex to the liposomes to, for example, the liver and the spleen. In order to allow transfection of DNA into cells which are not accessible through intravenous injection, it is possible to directly inject the liposome-DNA complexes into a specific location in an animal's body. For example, Nabel et al. teach injection via a catheter into the arterial wall. In another example, the inventors have used intraperitoneal injection to allow for gene transfer into mice.

The present invention also contemplates compositions comprising a liposomal complex. This liposomal complex will comprise a lipid component and a DNA segment encoding a neu-suppressing gene. The neu-suppressing gene employed in the liposomal complex can be, for example, an LT gene or an E1A gene. Liposomal complexes comprising LT mutants may have certain advantages. These advantages may be particularly distinct when the LT gene encodes non-transforming LT mutant, such as K1. An E1A gene encoding either the E1A 12S or E1A 13S gene product, or both, may be complexed with a lipid to form the liposomal complex.

The lipid employed to make the liposomal complex can be any of the above-discussed lipids. In particular, DOTMA, DOPE, and/or DC-Chol may form all or part of the liposomal complex. The inventors have had particular success with complexes comprising DC-Chol. In a preferred embodiment, the lipid will comprise DC-Chol and DOPE. While any ratio of DC-Chol to DOPE is anticipated to have utility, it is anticipated that those comprising a ratio of DC-Chol:DOPE between 1:20 and 20:1 will be particularly advantageous. The inventors have found that liposomes prepared from a ratio of DC-Chol:DOPE of about 1:10 to about 1:5 have been useful in the studies they have performed. In most studies, the inventors have used a ratio of 1.2 μmol DC-Chol:8.0 μmol DOPE.

The present invention also comprises kits for the introduction of a neu-suppressing gene product into a cell comprising a neu-suppressing DNA/liposome complex.

In that the inventors' studies have demonstrated that both the 12S E1A, 13S E1A, and LT gene products are capable of suppressing neu gene expression, it is proposed that one may employ any product, or two or more together, in the practice of the invention. Of course, in that the 12S and 13S products are derived from essentially the same gene sequences, and are merely the result of differential splicing, where the E1A gene itself is employed it will be most convenient to simply use the wild type E1A gene directly. However, it is contemplated that certain regions of either the E1A or the LT gene may be employed exclusively without employing the entire wild type E1A or LT gene respectively. It is proposed that it will ultimately be preferable to employ the smallest region needed to suppress the neu gene so that one is not introducing unnecessary DNA into cells which receive either an E1A or LT gene construct. This may especially be true with regards to the rather large, 708 amino acid, LT protein. Techniques well known to those of skill in the art, such as the use of restriction enzymes, will allow for the generation of small regions of E1A and LT. The ability of these regions to inhibit new can easily be determined by the assays reported in the Examples.

In general, techniques for assessing the reduction in transforming, tumorigenic or metastatic potential are well known in the art. For example, the simplest assay is to measure the level of DNA synthesis in treated versus non-treated cells, in that DNA synthesis is a good measure of cell growth potential. Furthermore, the ability of transformed cells as compared to non-transformed cells to grow in soft agar has been widely employed as a measure of the transformation. Thus, either of these two assay techniques may be conveniently employed to assess the ability of the E1A or LT products employed to suppress neu oncogene mediated transformation.

A number of accepted assays are also available where one desires to assess suppression of neu oncogene-mediated tumorigenic or metastatic potential. The most convenient indicator of tumorigenic potential, and indeed the most reliable, is an in vivo assay employing nude mice, wherein the ability of treated cells to cause tumors in the mice is assessed. Nude mice may be similarly employed where one desires to assess metastatic potential, by determining the ability of treated cells to form metastatic nodules, for example, in the lungs of experimental mice.

In that the inventors have observed that E1A gene products and LT function through direct suppression of neu gene expression, the invention further concerns a method for suppressing neu gene expression or overexpression. In these embodiments, the method includes introducing an E1A gene product or LT into the affected cell in a manner effective to suppress the cellular level of the neu p185 transmembrane protein. The suppression of p185 expression may be readily assessed by a number of available methods, including most conveniently, electrophoretic gel analysis to determine a reduction in p185 levels. It is proposed that the same means of introducing the E1A gene, its products, or LT, will be applicable in these further embodiments as discussed in connection with the transformation embodiments above.

Suppression of neu-Mediated Oncogenesis

Certain embodiments of the present invention concern methods for suppressing neu oncogene-mediated transformation of a cell comprising introduction of a transformation suppressing amount of an LT gene product into the cell in a manner effective to suppress an oncogenic phenotype. Suppression of an oncogenic phenotype is indicated by a reduction in the transforming, tumorigenic or metastatic potential of the cell, which can be measured via the assays described above.

In some embodiments of the invention, new oncogene-mediated transformation of the cell will be suppressed by an LT mutant which is nontransforming. Examples of such nontransforming mutants are K1 and K7.

Methods for introducing the LT gene product into the cell include the introduction of a DNA segment which encodes the LT gene product. In many cases, the DNA segment which comprises the LT gene will also comprise associated controlled sequences from the LT gene. Introduction of DNA segments which encode the LT gene product can be achieved by any of a variety of means known to those of skill in the art. However, the inventors anticipate the particularly good results might be achieved by the introduction of the DNA through a vector, or through the precisely described liposome-mediated gene transfer techniques. Of course, those of skill will understand that other methods of genetic transfer such as retrovirus vectors, adenovirus vectors, and adeno-associated virus vectors will also be useful in regards to the present invention.

Plasmid vectors, viral vectors such as adenoviral, retroviral, polyoma, cytomegaloviral and SV40 vectors are all anticipated to have utility with regards to methods of the present invention. However, certain preferred embodiments will comprise the use of plasmid vectors comprising DNA segments which encode an LT gene product. Exemplary plasmid vectors comprise pZ189, pVU-0, pK1, pK7, pSV21421, pSVd1423, psVd1425, pSVd1428, and pSVd1451. The pSVd1 series of vectors is described in Sullenger et al. (1990). An exemplary retroviral vector for use in regards to the present invention is pBabe-neo (Morgenstern et al. 1990).

In certain preferred embodiments of the present invention, the LT gene product is introduced into a cell of a multi-cellular organism. Typically, commercial embodiments of the invention will involve the introduction of the LT gene product into mammals, since the mammals encompass most commercially important animals for both livestock and health purposes. Obviously, some of the most important embodiments of the invention will be those directed towards the suppression of neu-mediated cancer in human beings.

The methods of the present invention will allow for the suppression of a variety of neu-mediated oncogenic phenotypes. Examples of such phenotypes are: (1) the ability to grow in soft agar; (2) the ability to form foci; and (3) a transformed morphology. In preferred embodiments of the invention, the oncogenic phenotype will be cancer. Particular cancers against which the present invention is anticipated to be most useful are any exhibiting neu-overexpression, such as cancers of the human breast, ovaries, lungs, gastric system, oral mucosa, and prostate. The methods of the present invention will be directed, in some cases towards the suppression of either the tumorigenic potential of the cell, the metastatic potential of the cell, or a combination of both.

Certain embodiments of the present invention comprise the introduction of both the LT antigen gene product and the E1A gene product into the same cell. Both the E1A gene product and the LT gene product have the ability to suppress neu-mediated cancer. However, the inventors have reported the surprising and unexpected finding that these two proteins suppress neu-mediated cancer in different manners. That either E1A or LT suppresses neu-mediated cancer is surprising in itself, since both gene products are known to have their own transforming properties. However, the fact that E1A and LT employ different mechanisms to allow for suppression of neu-mediated cancer would not at all be expected in view of the art. Owing to the facts that LT and E1A employ different mechanisms of neu-suppression, it will be possible to use both gene products in combination to doubly protect against neu-mediated suppression.

In embodiments which call for the introduction of both an E1A gene product and an LT gene product into the same population of cells, a typical manner of introduction of each of the products will be through the introduction of DNA segments which encode each product. These segments may be transfected simultaneously, or at separate times. The transfection may occur through any of the vectors discussed above, through liposome-mediated gene transfer, or through any of the other methods of gene transfer known to those in the art. Any of the LT antigen gene products discussed above will have utility in this embodiment of the invention. For example, LT, K1, and K7 are all anticipated to have utility when introduced in conjunction with an E1A gene product. Exemplary E1A gene products which will be useful in the present invention include E1A 12S and E1A 13S. Of course, it will also be possible to introduce the E1A and LT gene products directly into cells, or to introduce one product directly and the other via DNA transfection, depending on the needs of a particular cell.

In some embodiments of the invention, DNA segments encoding both an E1A gene product and an LT gene product can be linked in the same DNA segment. Further, each of these gene products may be placed under the control of the same set of regulatory sequences. In this manner, simultaneous transfection and expression of E1A and LT gene products may be achieved.

Since simultaneous transfection with E1A and LT will lead to two types of neu-suppression, it is anticipated that the combination will be particularly useful in preventing cancer. The methods of these embodiments may be used to reduce the transforming potential, tumorigenic potential and/or metastatic potential of cells.

Following long-standing patent law convention, the terms "a" and "an" mean "one or more" when used in this application, including the claims.

Definitions and Techniques Affecting Gene Products and Genes

E1A Gene Products and Genes

In this patent the terms "E1A gene product" and "E1A" refers to proteins having amino acid sequences which are substantially identical to the native E1A amino acid sequence and which are biologically active in that they are capable of binding to Rb, suppressing neu oncogene-mediated transformation, immortalizing cells, or cross-reacting with anti-E1A antibody raised against E1A. Such sequences are disclosed, for example, in Berk et al., 1978. The term "E1A gene product" also includes analogs of E1A molecules which exhibit at least some biological activity in common with native E1A. Furthermore, those skilled in the art of mutagenesis will appreciate that other analogs, as yet undisclosed or undiscovered, may be used to construct E1A analogs. Such analogs may be generated in the manners described for the generation of LT mutants in Kalderon et al. (1984). There is no need for an "E1A gene product" or "E1A" to comprise all, or substantially all of the amino acid sequence of the native E1A gene. Shorter or longer sequences are anticipated to be of use in the invention.

The term "E1A gene" refers to any DNA sequence that is substantially identical to a DNA sequence encoding an E1A gene product as defined above. The term also refers to RNA, or antisense sequences compatible with such DNA sequences. An "E1A gene" may also comprise any combination of associated control sequences.

The term "substantially identical", when used to define either an E1A amino acid sequence or E1A gene nucleic acid sequence, means that a particular subject sequence, for example, a mutant sequence, varies from the sequence of natural E1A by one or more substitutions, deletions, or additions, the net effect of which is to retain at least some biological activity of the E1A protein. Alternatively, DNA analog sequences are "substantially identical" to specific DNA sequences disclosed herein if: (a) the DNA analog sequence is derived from coding regions of the natural E1A gene; or (b) the DNA analog sequence is capable of hybridization of DNA sequences of (a) under moderately stringent conditions and which encode biologically active E1A; or (c) DNA sequences which are degenerative as a result of the genetic code to the DNA analog sequences defined in (a) or (b). Substantially identical analog proteins will be greater than about 80% similar to the corresponding sequence of the native protein. Sequences having lesser degrees of similarity but comparable biological activity are considered to be equivalents. In determining nucleic acid sequences, all subject nucleic acid sequences capable of encoding substantially similar amino acid sequences are considered to be substantially similar to a reference nucleic acid sequence, regardless of differences in codon sequence.

LT Gene Products and Genes

In this patent the terms "LT gene product" and "LT" refers to proteins having amino acid sequences which are substantially identical to the native LT amino acid sequence and which are biologically active in that they are capable of binding to Rb, suppressing neu oncogene-mediated transformation, immortalizing cells, inducing anchorage independency, or cross-reacting with anti-LT antibody raised against LT. Such sequences are disclosed, for example, in Tooze—*Molecular Biology of the Tumor Viruses*, Fiers et al., 1978, and Reddy et al. 1978. The term "LT gene product" also includes analogs of LT molecules which exhibit at least some biological activity in common with native LT. Examples of such LT analogs are K1 and K7, which are defective for transformation of cells (Kalderon et al., 1984). Many other exemplary LT analogs are disclosed in Kalderon et al. 1984, particularly in Table 2. Furthermore, those skilled in the art of mutagenesis will appreciate that other analogs, as yet undisclosed or undiscovered, may be used to construct LT analogs. There is no need for an "LT gene product" or "LT" to comprise all, or substantially all of the amino acid sequence of the native LT gene. Shorter or longer sequences are anticipated to be of use in the invention.

The term "LT gene" refers to any DNA sequence that is substantially identical to a DNA sequence encoding an LT gene product as defined above. The term also refers to RNA, or antisense sequences compatible with such DNA sequences. An "LT gene" may also comprise any combination of associated control sequences.

The term "substantially identical", when used to define either an LT amino acid sequence or an LT nucleic acid sequence, means that a particular subject sequence, for example, a mutant sequence, varies from the sequence of natural LT by one or more substitutions, deletions, or additions, the net effect of which is to retain at least some biological activity of the LT protein. Alternatively, DNA analog sequences are "substantially identical" to specific DNA sequences disclosed herein if: (a) the DNA analog sequence is derived from coding regions of the natural LT gene; or (b) the DNA analog sequence is capable of hybridization of DNA sequences of (a) under moderately stringent conditions and which encode biologically active LT; or (c) DNA sequences which are degenerative as a result of the genetic code to the DNA analog sequences defined in (a) or (b). Substantially identical analog proteins will be greater than about 80% similar to the corresponding sequence of the native protein. Sequences having lesser degrees of similarity but comparable biological activity are considered to be equivalents. In determining nucleic acid sequences, all subject nucleic acid sequences capable of encoding substantially similar amino acid sequences are considered to be substantially similar to a reference nucleic acid sequence, regardless of differences in codon sequence.

Percent Similarity

Percent similarity may be determined, for example, by comparing sequence information using the GAP computer program, available from the University of Wisconsin Geneticist Computer Group. The GAP program utilizes the alignment method of Needleman et al., 1970, as revised by Smith et al., 1981. Briefly, the GAP program defines similarity as the number of aligned symbols (i.e. nucleotides or amino acids) which are similar, divided by the total number of symbols in the shorter of the two sequences. The preferred default parameters for the GAP program include (1) a unitary comparison matrix (containing a value of 1 for identities and 0 for non-identities) of nucleotides and the weighted comparison matrix of Gribskov et al., 1986, as described by Schwartz et al., 1979; (2) a penalty of 3.0 for each gap and an additional 0.01 penalty for each symbol and each gap; and (3) no penalty for end gaps.

Nucleic Acid Sequences

In certain embodiments, the invention concerns the use of neu-suppressing genes and gene products, such as the LT antigen gene product or the E1A gene product, or both, that include within their respective sequences a sequence which is essentially that of the known LT antigen gene or E1A gene, or the corresponding proteins. The term "a sequence essentially as that of LT antigen or E1A" means that the sequence substantially corresponds to a portion of the LT antigen or E1A gene and has relatively few bases or amino acids (whether DNA or protein) which are not identical to those of LT or E1A (or a biologically functional equivalent thereof, when referring to proteins). The term "biologically functional equivalent" is well understood in the art and is further defined in detail herein. Accordingly, sequences which have between about 70% and about 80%; or more preferably, between about 81% and about 90%; or even more preferably, between about 91% and about 99%; of amino acids which are identical or functionally equivalent to the amino acids of LT antigen or E1A will be sequences which are "essentially the same".

LT antigen and E1A genes which have functionally equivalent codons are also covered by the invention. The term "functionally equivalent codon" is used herein to refer to codons that encode the same amino acid, such as the six codons for arginine or serine, and also refers to codons that encode biologically equivalent amino acids (Table 1).

TABLE 1

Functionally Equivalent Codons.

| Amino Acids | | | Condons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | m | AUG |
| Asparagine | Asn | N | AAC AAU |
| Proline | Pro | p | PCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences which may, for example, include various non-coding sequences flanking either of the 5' or 3' portions of the coding region or may include various internal sequences, i.e., introns, which are known to occur within genes.

The present invention also encompasses the use of DNA segments which are complementary, or essentially complementary, to the sequences set forth in the specification. Nucleic acid sequences which are "complementary" are those which are capable of base-pairing according to the standard Watson-Crick complementarity rules. As used herein, the term "complementary sequences" means nucleic acid sequences which are substantially complementary, as may be assessed by the same nucleotide comparison set forth above, or as defined as being capable of hybridizing to the nucleic acid segment in question under relatively stringent conditions such as those described herein.

Biologically Functional Equivalents

As mentioned above, modification and changes may be made in the structure of E1A or LT and still obtain a molecule having like or otherwise desirable characteristics. For example, certain amino acids may be substituted for other amino acids in a protein structure without appreciable loss of interactive binding capacity with structures such as, for example, the neu-gene. Since it is the interactive capacity and nature of a protein that defines that protein's biological functional activity, certain amino acid sequence substitutions can be made in a protein sequence (or, of course, its underlying DNA coding sequence) and nevertheless obtain a protein with like or even countervailing properties (e.g., antagonistic v. agonistic). It is thus contemplated by the inventors that various changes may be made in the sequence of the E1A or LT proteins or peptides (or underlying DNA) without appreciable loss of their biological utility or activity.

It is also well understood by the skilled artisan that, inherent in the definition of a biologically functional equivalent protein or peptide, is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted. Of course, a plurality of distinct proteins/peptides with different substitutions may easily be made and used in accordance with the invention.

It is also well understood that where certain residues are shown to be particularly important to the biological or structural properties of a protein or peptide, e.g., residues in active sites, such residues may not generally be exchanged. This is the case in the present invention, where it any changes in the neu-binding region of either E1A or LT that render the peptide incapable of suppressing neu-mediated transformation would result in a loss of utility of the resulting peptide for the present invention.

Amino acid substitutions, such as those which might be employed in modifying either E1A or LT are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4) .

In making changes based upon similar hydrophilicity values, the substitution of amino acids whose hydrophilicity values are within ±2 is preferred, those which are within ±1 are particularly preferred, and those within ±0.5 are even more particularly preferred.

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid.

Sequence Modification Techniques

Modifications to the E1A and LT peptides may be carried out using techniques such as site directed mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art as exemplified by publications (Adelman et al., 1983). As will be appreciated, the technique typically employs a phage vector which exists in both a single stranded and double stranded form. Typical vectors useful in site-directed mutagenesis include vectors such as the M13 phage (Messing et al., 1981). These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart the two strands of a double stranded vector which includes within its sequence a DNA sequence which encodes the E1A gene or the LT gene. An oligonucleotide primer bearing the desired mutated sequence is prepared, generally synthetically, for example by the method of Crea et al. (1978). This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

Kalderon et al. (1984) report several mutagenic methods which have proved useful in mutating the native LT gene. Specifically, Kalderon et al. teach deletion mutations by displacement-loop mutagenesis and by the random insertion of EcoRI linkers into the LT gene. Further, point mutation by deletion-loop mutagenesis is taught. The reference also teaches screening procedures for determining the success of such mutations. The teachings of Kalderon et al. (1984) are incorporated by reference in this application.

The preparation of sequence variants of the selected gene using site-directed mutagenesis is provided as a means of producing potentially useful E1A, LT, or other neu-suppressing species and is not meant to be limiting as there are other ways in which sequence variants of these peptides may be obtained. For example, recombinant vectors encoding the desired genes may be treated with mutagenic agents to obtain sequence variants (see, e.g., a method described by Eichenlaub, 1979) for the mutagenesis of plasmid DNA using hydroxylamine.

Other Structural Equivalents

In addition to the E1A and LT peptidyl compounds described herein, the inventors also contemplate that other sterically similar compounds may be formulated to mimic the key portions of the peptide structure. Such compounds may be used in the same manner as the peptides of the invention and hence are also functional equivalents. The generation of a structural functional equivalent may be achieved by the techniques of modelling and chemical design known to those of skill in the art. It will be understood that all such sterically similar constructs fall within the scope of the present invention.

BRIEF DESCRIPTION OF THE DRAWINGS

FIG. 1A. Transcriptional repression of neu promoter by E1A gene products. Rat-1 cells were transfected with 5 µg of the pNeu-EcoR1-CAT construct, which contains the CAT gene driven by neu oncogene promoter containing 2.2-kb upstream DNA sequences. Lane 1, basal neu promoter activity (its relative CAT activity is defined as 100%); lanes 2–4, CAT activity after cotransfection with 10 µg of carrier DNA pSP64 vector (102%, lane 2); E1A-expressing plasmid pE1A (34%, lane 3); pE1Apr, a plasmid containing only the E1A promoter (98%, lane 4). The CAT activities of a reporter plasmid, RSV-CAT, containing the CAT gene under the control of RSV LTR (10%, lane 5) were not significantly changed by cotransfection of 10 µg of pE1A (98%, lane 6) or 20 µg of pE1A (96%, lane 7).

FIG. 1B. Effect of various adenovirus early genes on neu promoter activity. The pneuEcoRI-CAT was cotransfected with pSP64 vector or plasmid expressing various adenovirus early genes, E1A, E1b, E2A, and E3, as indicated. The relative CAT activities are as follows: SP64, 100%; E1A, 35%, E1B, 97%, E2A, 99%, E3, 102%. RSV-CAT was used as a positive control.

FIG. 3A. Schematic maps of the neu promoter 5' deletion constructs that were fused individually to the CAT gene to create the plasmids as indicated by the names of the restriction enzymes used for generating the constructs.

FIG. 3B. Level of expression of the CAT gene directed by each of the promoter fragment constructs after transfection of 5 µg of the plasmids into Rat-1 cells with 10 µg of cotransfected pE1A (E) or carrier DNA pSP64 (C). The names of restriction enzymes above each triplet assay refer to the constructs indicated in the maps.

FIG. 4A. Rat-1 cells were transfected with 5 µg of the pNeuEcoR1-CAT plasmids giving basal neu promoter activity (lane 1); the repressed CAT activity after cotransfection with 5 µg of the pE1A is shown in lane 2. Plasmids pSP64/Stu-Xho containing the Stu I-Xho I neu promoter fragment cloned in pSP64 were cotransfected with pneuEcoR1-CAT and pE1A. Lanes 3–6 show the competitive effects of increasing amounts (5, 10, 15, and 20 µg, respectively) of pSP64/Stu-Xho. Plasmids pSP64/R1-Xba containing the EcoRI-Xbu I neu promoter fragment were also cotransfected with pneuEcoR1-CAT and pE1A. Lanes 7–9 show CAT activities from neu promoter by cotransfecting 5, 10, and 20 µg of pSP64/RI-Xba, respectively. The relative CAT activities of lanes 1–9 are as follows: 100%, 32%, 27%, 31%, 58%, 79%, 38%, 31%, 24%.

FIG. 4B. Immunoblot for p185 protein in the cell lysates of SK-BR-3 breast cancer cells transfected by pneuEcoRV-CAT. Seventy-five micrograms of protein from each sample was electrophoresed on 7% SDS/PAGE gels prior to transfer on nitrocellulose. Filters were blotted with the primary antibody mAb-3. Lane 1, lysates of SK-BR-3 cells transfected with 5 µg of pE1A; lane 2, cotransfected with 5 µg E1A and 20 µg of pSP64/RI-XbaI; lane 3, cotransfected with 5 µg of E1A and 20 µg of pSP64/Stu-Xho; lane 4, lysates of SK-BR-3 cells after mock transfection. The protein size marker is shown on the right. The arrow indicates the position of p185 protein. The p185 protein bands were scanned by Bio-Rad video densitometer model 620 to determined the relative p185 protein level. The p185 protein level in the mock transfection sample is defined as 100% and the relative amounts of p185 proteins in lanes 1–3 are 57%, 54%, and 89%, respectively.

FIG. 6A. Southern blot analysis of NIH3T3, B104-1-1 and their transfectants using an EcoRI-SstI E1A DNA probe. 10 µg of genomic DNA from the indicated cell lines were digested to completion with EcoRI+SstI restriction endonucleases and subjected to electrophoresis on a 1% agarose gel. The DNAs were transferred to Nitran™ filter paper and hybridized with the E1A probe. The DNA markers are shown on the left.

FIG. 6B. Immunoblot analysis for E1A proteins in the cell lysates of the indicated cell lines. 50 µg of each sample were electrophoresed on 10% SDS-PAGE prior to transfer to nitrocellulose. Filters were incubated with the primary antibody M73 against E1A, obtained from Dr. L. S. Chang of Ohio State University. The protein molecular weight marker and the position of E1A proteins are shown on the right. 25 µg of Cell lysate from 293 cells was used as a positive control.

FIG. 6C. Immunoblot analysis for the neu encoded p185 protein in the cell lysates of the indicated cell lines. The studies were performed as described in section FIG. 6B above. The primary antibody was mAB-3 against p185, purchased from Oncogene Science Inc.

FIG. 6D. Southern blot analysis of the indicated cell lines using rat neu DNA probe. The studies were performed as described in section FIG. 6A above. The DNAs were digested with Bam HI restriction endonuclease.

(FIG. 7A) B104-1-1; (FIG. 7B) B-E1Apr; (FIG. 7C) N-E1A-1; (FIG. 7D) B-E1A-1; (FIG. 7E) B-E1A-2; (FIG. 7F) B-E1A-3 (Magnification: ×130).

FIGS. 8A and 8B show E1A effects on DNA synthesis. (FIG. 8A) [$^3$H]Thymidine Incorporation of the indicated cell lines. 9×10$^3$ cells were plated in 96 well multiwell plates and cultured in Dulbecco's modified Eagle medium supplemented with 10% calf serum for 16, 40 and 64 hrs. Cell received a 2 hr pulse of 1 μCi [$^3$H]-thymidine per well to label those that were synthesizing DNA prior to harvest. Radioactivities of individual samples were counted by scintillation counter. Average cpm counts were calculated from replicated samples.

FIG. 8B. Anchorage independent growth of E1A-transfected B104-1-1 and NIH3T3 cells. 1×10$^3$ cells were plated in 0.35% soft agar over a 0.7% agar lower layer. Colonies were counted after 4 weeks. A typical plate and the mean of triplicate samples plus or minus the standard error of the mean are shown for each group.

FIGS. 9A and 9B show the effects of a tumorigenicity study.

FIG. 9A. Summary of tumorigenicity of B104-1-1, NIH3T3 and their transfectant. 1×10$^5$ viable cells were injected subcutaneously into right and left flanks of female homozygous nu/nu mice, respectively. Tumor formation was scored at indicated days as presence or absence of a visible tumor mass. 16 days after injection, tumor volumes were estimated as the product of tri-dimensional caliper measurements (longest surface length and width, and tumor thickness). N.D.: not detectable at the time of evaluation.

FIG. 9B. A representative result of tumorigenicity study. From right to left: the animals were injected with B104-1-1, B-E1A-2 or NIH3T3 cells 18 days prior to the photographing data.

FIG. 10A. E1A gene products inhibited the cell motility of the neu-transformed 3T3 cells. N-E1A: NIH3T3 cells transfected with E1A; B-neo: B104-1-1 cells transfected with neomycin resistant gene; B-E1A-1 to 5: five independent cell lines generated by transfecting E1A gene into B104-1-1 cells. The motility assays were carried out by using a transwell unit with 5 μm pore size polycarbonate filter in 24 well cluster plate (Costar). Lower compartment of the transwell contained 600 μl of one of the chemoattractants: 20 μm fibronectin (FN) or 100 μm FN dissolved in DMEM/F12, or hepatic endothelial cell conditioned media (HSE), or DMEM/F12 medial only as negative control. The cells (3×10$^4$/0.1 ml in DMEM/F12) were plated in the upper compartment and incubated for 6 hrs at 37° C. in a humidified 5% CO$_2$ atmosphere. After the incubation, the filters were fixed with 3% glutaraldehyde in PBS buffer and stained with Geimsa. ach sample was assayed in triplicate and cell motility was measured by counting the number of cells that had migrated to the lower side of the filter. At least four HPFs were counted per filter. The number of cells migrated to DMEM/F12 has been deducted from each sample to eliminate the background and all the assays were done in triplicates.

FIG. 10B. E1A gene products inhibited the invasiveness of the neu-transformed 3T3 cells. The assay of in vitro invasiveness was done basically as described by Albini et al, 1987 and Repesh, 1989. The basement membrane preparation, matrigel, was purchased from Collaborative Research, Inc. Filters in the transwell unit (same as used in motility assay) were coated with 0.1 ml of 1:20 dilution of matrigel in DMDM/F12 media. Lower compartment contained 0.6 ml of HSE as chemoattractant or DMEM/F12 as negative control. The cells (5×10$^4$/0.1 ml in DMEM/F12) were plated in upper compartment and incubated for 72 hrs at 37° C. in a humidified 5% CO$_2$ atmosphere. Cells were fixed, stained and counted as described in 1.a. All the assays were done in triplicate and assays were repeated twice.

FIGS. 10C–10F. Gross appearance of lungs from the mice injected with B-neo cells (FIG. 10C), N-E1A cells (FIG. 10D), B-E1A-1 cells (FIG. 10E), and B-E1A-2 cells (FIG. 10F); E1A gene products inhibited the lung colonization of neu-transformed cells. See legend for Table 2 for methodological details.

FIG. 11A. Top, animal injected with B104-1-1 cells, a neu oncogene transformed NIH3T3 cell line; Bottom, animal injected with B-E1A2 cells, an E1A transfectant of B104-1-1. Photographs were taken 18 days after injection, and results are representative of other tumorigenicity studies.

FIG. 11B. Left, gross appearance of lungs from mice injected with B104-1-1 cells; Right, gross appearance of lungs from mice injected with the E1A transfected cells, B-E1A2. Mice were inoculated with 1×10$^5$ cells/0.1 ml in PBS via the lateral tail vein at day 0, and were sacrificed 21 days after injection. The numbers of lung tumor nodules were determined following infiltration with India ink, only those lung nodules greater than 1 mm in diameter were counted in the assay.

FIG. 12A. immunoblot analysis of E1A proteins in the cell lysates of the indicated cell lines. Seventy-five mg of proteins from each sample were subjected to electrophoresis on 10% sodium dodecyl sulfate-polyacrylamide gel prior to transfer to nitrocellulose. Filters were incubated with the primary antibody M73, which recognizes E1A proteins. The position of the E1A proteins are indicated to the left of A.

FIG. 12B. immunoblot analysis of the c-erbB-2/neu-encoded p185 proteins in the cell lysates of the indicated cell lines. Seventy-five mg of proteins from each sample were subjected to electrophoresis on 10% sodium dodecyl sulfate-polyacrylamide gel prior to transfer to nitrocellulose. Filters were incubated with the primary antibody c-neu-Ab-3 against p185. The position of the p185 proteins are indicated to the left of B.

FIG. 12C. Southern blot analysis of DNAs from the ip1.E1A and ip1.Efs transfectants. Ten mg of genomic DNA from indicated cell lines were hybridized with the full-length c-erbB-2/neu cDNA probe. DNA markers are shown to the right.

FIG. 13A. reduced growth rate of the ip1.E1A transfectants versus control ip1.Efs cells. The in vitro growth rates of the cell lines were assessed by measuring increases in cell number with the MTT assay (Alley et al., 1988). Cells ($2\times10^3$/well) were plated in 96-well culture plates in 0.2 ml of culture medium. A total of 5 plates (9 wells/cell line/plate) were used. One of the plates was analyzed at 24-h intervals after the addition of 40 µl MTT (Sigma Chemical Co., St. Louis, Mo.) stock solution (1.25 mg MTT/ml of phosphate-buffered saline) to each well on the plate. Cells were incubated at 37° C. for 2.5 h, the medium was aspirated, and the cells were lysed in 100 µl of dimethyl sulfoxide. Conversion of MTT to formazan by metabolically viable cells was monitored by a Dynatech MR 5000 fluorescence microplate reader at a wavelength of 450 nm. Results were analyzed by regression analysis. Each study was repeated for each cell line at least twice.

FIG. 13B. decreased [$^3$H]thymidine incorporation by the ip1.E1A transfectants versus control ip1.Efs cells. For this assay, 10 replicated cell samples were plated into 96-well plates at a density of $8\times10^3$ cells/well in culture medium. [$^3$H]Thymidine (1 µCi) was added to each well at 24, 48, and 72 h, respectively, with continuous incubation after each addition for 12 h at 37° C. Cells were harvested, and cellular DNA was bound to fiberglass filters. The radioactivity of each filter was counted with a scintillation counter. Average cpm were calculated from ten replicate samples.

FIG. 13C. significantly inhibited colony formation for the ip1.E1A transfectants versus control ip1.Efs cells ($P<0.01$). Soft agar assays were performed as previously described (Matin et al., 1990). Cells ($1\times10^3$ cells/well) were plated in a 24-well plate in culture medium containing 0.35% agarose (BRL, Gaithersburg, Md.) overlying a 0.7% agarose layer. The cells were then incubated at 37° C. for 5 weeks, after which the plates were stained with p-iodonitrotetrazolium violet (1 mg/ml) for 48 h at 37° C. Colonies greater than 100 µm were counted for each dish and cell line. The numbers of soft agar colony are shown in the figure. Studies were repeated four times for each cell line.

FIG. 14A. E1A suppressed tumor formation by c-erbB2-/neu-overexpressing ovarian cancer cells. Four- to 6-week-old athymic female homozygous nu/nu mice were purchased from the Animal Production Area, National Canter Institute-Frederick Cancer Research Facility (Frederick, Md.) or from Harlan Sprague Dawley, Inc., (Indianapolis, Ind.). The care and use of the animals was in accordance with institutional guidelines. For tumorigenicity assays, cells in log-phase growth were trypsinized, washed twice with phosphate-buffered saline, and centrifuged at 250×g. The viable cells were counted; of those, $3\times10^6$ cells in 0.1 ml of phosphate-buffered saline were injected s.c. into both the right and left flanks of female mice under aseptic conditions. Tumor volumes were estimated as the product of three-dimensional caliper measurements (longest surface length and width; tumor thickness). The growth of tumors was monitored for a minimum of 80 days and a maximum of 160 days, as shown by the days indicated in the figure.

FIG. 14B. longer survival of mice given injections of E1A-expressing ip1.E1A cells versus mice given injections of ip1.Efs human ovarian cancer cells ($P<0.01$). To assess the formation of malignant ascites after i.p. injection, suspensions of cells (harvested as above) at concentrations of $1\times10^6$ in 0.2 ml of Hank's balanced salt solution were injected i.p. into individual female nu/nu mice. In two studies, totals of nine mice for the ip1.Efs line, eight mice for the ip1.E1A1 line, and nine mice fore the ip1.E1A2 line were given injections. Mice were initially observed twice a twice a week for signs of tumor development and then daily when any or all of the following tumor symptoms appeared: abdominal bloating, loss of subcutaneous fat, hunched posture, and decreased movement. Mice were killed when they appeared moribund or, judging from the inventors previous experience, would not survive more than 24–48 h. Symptom-free mice were killed 120 days after injection. Autopsies were performed on all mice killed. Similar results were obtained from the two studies, and results were combined for analysis.

FIGS. 15A–15C show expression of neu-encoded p185 and LT in B104-1-1 cells stably transfected with plasmids encoding LT.

FIG. 15A. Immunoblotting for anti-p185 of whole cell lysates from B104-1-1 cells stably transfected with LT: BTn16 (lane 1), BTn14 (lane 2), BEn5 (lane 3) and NIH 3T3 (lane 4) cell lines. Following transfer to nitrocellulose, the blots were probed with monoclonal anti-p185 antibody (c-neu, Ab-3, Oncogene Science) followed by goat anti-mouse conjugated to horse radish peroxidase. The blot was subsequently developed using horse radish peroxidase substrate and hydrogen peroxide.

FIG. 15B. Immunoblot for LT of whole cell lysates of the stable transfectants. Blots were probed with anti-LT (SV 40 T-Ag, Ab-2, Oncogene Science) and then with [125I]-protein A. Washed and dried blots were exposed for autoradiography. Lysates of BTn16, lane 1; BTn14, lane 2; BEn5, lane 3 and NIH 3T3 cell line, lane 4.

FIG. 15C. Southern blotting for genomic neu using 32P-labelled 0.4 and 0.8 kb Bam H1 fragments (11) from neu cDNA probe to hybridize with Bam H1 digested genomic DNA isolated from BTn16, lane 1; BTn14, lane 2; BEn5, lane 3 and NIH 3T3 cells, lane 4. The rat neu-specific bands are indicated by a triangle.

FIG. 18A. Series deletion-CAT constructs of the rat neu promoter.

FIG. 18B. Mapping of LT responding region in the neu upstream regulatory sequence using the neu deletion-CAT constructs. One mg of each of the neu deletion-CAT constructs were cotransfected into NIH 3T3 cells with 10 mg of the LT-producing plasmid, pVU-0 (indicated by +) or 10 mg of filler plasmid, pSV2E (indicated by –): Set 1, pneuEcoR1CAT; set 2, pneuXba1CAT; set 3, pneuEcoRV2CAT; set 4, pneuEcoRVCAT; set 5, pneuStu1CAT; set 6, pneuXho1CAT; M, control CAT assay of extracts from untransfected NIH 3T3 cells. Each set (set 1, set 2, etc.) of CAT reactions with (+) and without LT (−) were standardized to equal protein concentrations.

FIG. 20A. Schematic diagram of LT showing Rb binding domain (shaded black). K1 encodes LT with single amino acid change (glu 107 to lys) in the Rb binding domain of the 708 amino acid LT protein.

FIG. 20B. Activity of pneuXho1CAT (with control plasmid pSV2E) and inhibition of activity in the presence of wild type LT (WT), and mutant LT (K1). One mg pneuXho1CAT was cotransfected with 10 mg of filler plasmid, pSV2E, or wild type LT (pVU-0) or mutant LT (pK1).

FIG. 20C. Effect of K1 on the transforming activity of activated neu. One mg of cNeu-104 was cotransfected with 2 mg of K1 and 0.1 mg of pSV2neo into Rat-1 cells. pSV2E was used as filler plasmid so that a final 5 mg DNA was transfected into cells. Cells were split 1:4 48 hours after transfection and duplicate plates were subsequently grown in regular medium (DMEM/F12 plus 10% calf serum) or regular medium supplemented with 250 mg/mL G418. Foci and G418-resistant colonies were stained and counted after 3–4 weeks. Results are expressed as ratio of foci to that of G418-resistant colonies from each transfection to correct for transfection efficiency. The number of foci from transfecting cNeu-104 alone was set at 100%.

FIG. 26A. Mice were administered intraperitoneal SK-OV-3(i.p.), two months later after tumor development, Ad.RSVβgal was administered intraperitoneally. Tumor and organs were evaluated for the presence of β-gal using X-gal. The lacZ gene was localized in tumor cells and only slight β-gal activity was detected in normal organs.

FIG. 26B. Mice were administered intratracheally H820. Two months later, after tumor development, AD.RSVβgal was administered intravenously. Tumor and organs were evaluated for the presence of β-gal using X-gal. The lacZ gene was localized in tumor cells and only slight β-gal activity was detected in some normal organs.

FIG. 28A. Histological section from intraperitoneal SK-OV-3(i.p.) stained with hematoxylin and eosin.

FIG. 28B. Expression level of HER-2/neu P185 protein: stained by polyclonal antibody against P185 with ABC alkaline phosphatase substrate kit. Positive: red color.

FIG. 28C. Expression of AD.E1A protein: stained by monoclonal antibody against AD.E1A with ABC ACE substrate kit for horseradish peroxides. Positive: dark red color. Ad.E1A protein was detected in tumor tissue treated by Ad.E1A(+) in vivo. The expression level of HER-2/neu P185 was greatly inhibited in treated mouse tumor tissue.

DETAILED DESCRIPTION OF THE PREFERRED EMBODIMENTS

Figure 1A:
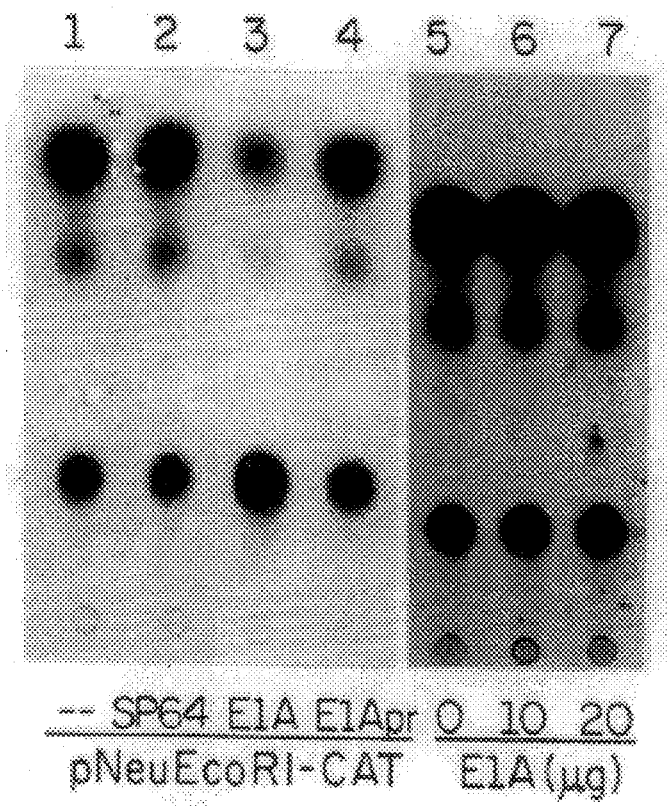
FIGS. 1A and 1B show E1A gene product effects on the neu promoter.

The neu oncogene is a transforming gene originally identified from rat neuro/glioblastomas (Shih et al., 1981).

Subsequently, both the activated neu oncogene and its normal cellular counterpart, the normal neu gene, were cloned from rat and human libraries (Bargmann et al., 1986; Coussens et al., 1985; Hung et al., 1986; Yamamoto et al., 1986). The neu gene encodes a 185-KDa transmembrane protein (p185) which is related to, but distinct from the epidermal growth factor receptor (EGF-r). The neu encoded p185 and EGF-r have identical gross structural organization including ligand-binding, transmembrane and intracellular kinase domains and also share extensive sequence homology, specifically, >80% of the amino acids in the tyrosine kinase domain are identical. Recently, the ligand for the neu-encoded p185 protein has been functionally identified in rat cells and isolated from human breast cancer cells, which will facilitate the better understanding of the function of the neu-encoded p185 protein in normal and malignant cell growth and development (Lupu et al., 1990; Yarden et al., 1989).

The activated neu oncogene contains a single amino acid substitution in the transmembrane domain and possesses an increased tyrosine kinase activity when compared to its normal counterpart. Furthermore, it has demonstrated that amplification of the neu protooncogene facilitates oncogenic activation by a single point mutation (Hung et al., 1989). The human homologue of the rat neu oncogene, also named as HER-2 or c-erbB2, has been shown to be amplified/overexpressed in 25–30% of human primary breast cancers and ovarian cancers (Hung et al., 1988; Slamon et al., 1987). Breast cancer patients with neu overexpression show a significantly lower overall survival rate and a shorter time to relapse than those patients without neu overexpression, suggesting that neu overexpression may be used as a prognostic factor (Id.). Amplification/overexpression of the human neu gene has also been shown to correlate with the number of axillary lymph nodes positive for metastasis in breast cancer patients (Id.). These studies strongly suggest that the neu oncogene may play an important role in malignant transformation and metastasis.

A. EXAMPLES OF NEU SUPPRESSION WITH E1A

The primary function of the adenovirus E1A gene is to activate other adenoviral genes during a permissive viral infection by modifying the host cell transcriptional apparatus, thereby resulting in host cell immortalization of transformation by the whole adenoviral early region (Berk et al., 1986). Although both transcriptional activation and transcriptional repression of non-adenoviral genes by the E1A proteins have been reported (Borrelli et al., 1984; Hen et al., 1985; Lillie et al., 1989; Sassome-Lorsi et al., 1987; Stein et al., 1987), their functional significance and physiological impact is unclear in many cases. Interestingly, it has been shown that exogenously added E1A gene can reduce the metastatic potential of ras transformed rat embryo fibroblasts (REF) cells by activating the cellular nm23 gene which is a lately cloned and characterized cellular metastatic suppressor gene (Pozzaati et al., 1988). Additionally, the transfected E1A gene has been shown to repress secreted protease gene expression at the transcriptional level and inhibits metastasis of human tumor cells (Liotta, 1989).

Recently, the present inventors have studied the effects of the E1A gene products on the promoter activity of the neu gene and found that E1A proteins can repress the expression of both human and rat neu oncogene at the transcriptional level. Since both the neu gene and the E1A gene are well-known transforming oncogenes, these findings raised an interesting question: Is it possible that the E1A proteins may act as transformation suppressor for the neu-transformed cells via transcriptional repression?

To address this question, the inventors undertook to develop a biological functional assay system in which the effects of E1A could be studied. The E1A gene was introduced into the neu transformed B104-1-1 cells to generate a derivative that stably express the E1A gene products, these cells were termed B-E1A cells. The transformed phenotypes of the parental neu-transformed B104-1-1 cell line and the B-E1A cell lines could then be compared following injection of each cell type into nude mice. The findings dramatically demonstrated that the E1A gene products can act as suppressors of neu oncogene-mediated cell transformation and metastasis.

The Examples which follow set forth studies wherein the inventors demonstrate the ability of the E1A gene to suppress neu gene expression (Example I), neu gene-mediated tumorigenicity (Example II), neu gene-mediated metastasis (Example III), to suppress c-erbB-2/neu expression in human ovarian carcinoma (Example IV), and gene therapy with E1A (Example VIII). Examples V and VI demonstrate suppression of neu with LT antigen. While these studies are believed to be exemplary of the invention, it will be appreciated by those of skill in the art that many modifications and alterations may be made in these embodiments without departing from the spirit and scope of the invention.

EXAMPLE I

Transcriptional Repression of the neu Protooncogene by Adenovirus 5 E1A Gene Products This Example relates to studies conducted by the inventors which demonstrate that the adenovirus E1A 12S and 13S products are effective in repressing the transcriptional activity of the neu promoter. In particular, it is demonstrated that the conserved region 2 (CR2) of the E1A proteins are required for repression. Moreover, these studies indicated that a cis-acting DNA element in the upstream region of the neu promoter is responsible for the trans inhibition of the promoter by the E1A gene products.

1. Materials and Methods a. Plasmids

The recombinants used in this study have been described. pE1A (Chang et al., 1989: Hearing et al., 1985) is a plasmid expressing only the E1A region gene; pE1A12S and pE1A13S (Hearing et al., 1985) express 12S E1A protein and 13S E1A protein, respectively; pE1A-d1343 (Hearing et al., 1985) contains a 2-base-pair (bp) frameshift deletion in the E1A coding sequences (adenovirus nucleotide sequence positions 621 and 622); pE1A-d1346 (Hearing et al., 1985) contains an in-frame deletion of nucleotides 859–907 (48 bp), resulting in the deletion of 16 amino acids inside the CR2 of the E1A proteins; pE1Apr contains only the E1A promoter (−499 to +113 relative to the E1A cap site); pE2A-CAT (Chung et al., 1989) is a reporter plasmid containing E2 early promoter fused with the chloramphenicol acetyltransferase (CAT) reporter gene; pRSV-CAT is a reporter plasmid containing the CAT gene under the control of the Rous sarcoma virus (RSV) long terminal repeat (LTR); pE1B, pE2, and pE3 are plasmids expressing E1B, E2, and E3 genes, respectively. pneuEcoR1-CAT contains the 2.2-kilobase (kb) rat neu promoter and upstream sequences linked to the CAT gene. The deletion mutant of the neu promoter used in this study are described in the legends to FIGS. 3A, 3B and 4A. pRSV-β-gal contains the RSV LTR linked to β-galactosidase gene used as an internal control for transfection efficiency.

b. Cell Cultures

Cell cultures were performed as described (Hung et al., 1989; Matin, et al., 1984). The Rat-1 and SK-BR-3 cells were grown in dulbecco's modified Eagle's medium (DMEM) supplemented with 10% calf serum and fetal calf serum, respectively.

c. DNA Transfection

All transfections were carried out with the calcium phosphate precipitation technique of Graham and Van der EB as modified by Anderson et al. (Hung et al., 1989; Anderson et al., 1979; Ausubel et al., 1987). In each transfection, $8 \times 10^5$ Rat-1 cells or $2 \times 10^6$ SK-BR-3 cells ($2 \times 10$ cm dishes) were seeded 24 hr before transfection. Total transfection DNA was kept constant (maximum, 30 µg) among different samples in the same experiment by adding approximate amounts of carrier DNA (pSP64).

d. CAT Assays

Cell extracts were prepared 40 hr after transfection. Portions of cell lysates were assayed for β-galactosidase activity from the cotransfected pRSV-β-gal plasmid. All CAT assays (Gorman et al., 1982) were normalized to the internal transfection efficiency control. The CAT assay monitors acetylation of [$^{14}$C]chloramphenicol in cell extracts; [$^{14}$C]-chloramphenicol and its products are separated by thin-layer chromatography (TLC) and visualized by autoradiography. Individual spots on TLC paper were cut, their radioactivities were assayed by liquid scintillation spectrometry, and the relative CAT activities were calculated accordingly. Each experiment has been reproducibly repeated at least three times and a representative of several studies is shown.

e. Immunoblot

SK-BR-3 cell lysates were made 40 hr after transfection and immunoblots were performed as described (Matin et al., 1984). The mAB-3 monoclonal antibody against the human neu gene product—p185 protein—was purchased from Oncogene Science.

2. Results a. Transcriptional Repression of neu by the Adenovirus 5(ADS) E1A Products

A DNA segment of 2.2 kb containing the neu promoter and upstream sequences was fused with the CAT expression vector to generate the pneuEcoR1-CAT plasmid. In transient-expression assays using Rat-1 cells (FIG. 1A), a cotransfection of pneuEcoR1-CAT with pE1A, a plasmid expressing the E1A gene, led to a significant decrease of CAT activity. Cotransfection with pSP64, a plasmid vector, had no effect on CAT activity. To rule out the possibility that decreased transcription from neu promoters could be due to the titration of cellular transcription factors by the cotransfected E1A promoter, a deletion mutant, pE1Apr, which contains only the E1A promoter, was cotransfected with pneuEcoR1-CAT. No effect on CAT activity was observed. A reporter plasmid containing the CAT gene under the control of the RSV LTR was not E1A responsive, indicating that decreased CAT expression was not due to a general decrease of transcription by E1A.

Figure 1B:
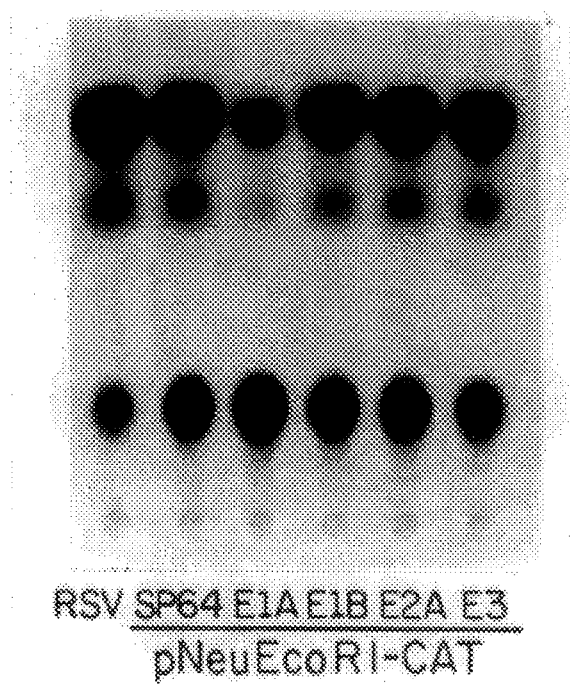

In parallel studies, stimulation of transcription from the E2A transcription unit by the E1A products was assayed by cotransfecting pE1A and pE2A-CAT (CAT gene driven by E2 early promoter). The results showed that repression of neu and transactivation of E2A promoter occur in the same range of pE1A concentration. To see if other adenovirus early genes can repress the neu promoter, plasmids expressing the early genes of adenovirus individually were cotransfected with pneuEcoR1-CAT (FIG. 1B). No change in CAT activity was observed with E1B, E2, or E3 alone, indicating the among these early genes of adenovirus, only the E1A gene could function as a repressor of the neu promoter.

b. Repression of neu Is E1A Concentration Dependent and Requires the E1A Conserved Region 2

Figure 2A:
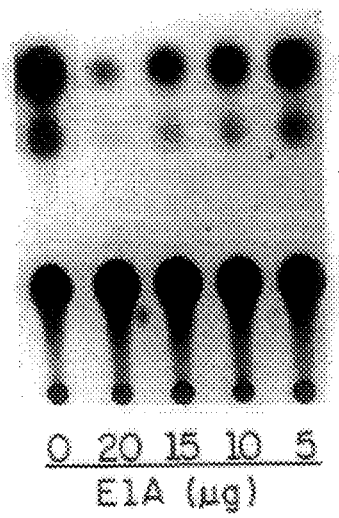
FIGS. 2A–2E show transient expression from neu promoter with cotransfection with increasing amounts of pE1A (FIG. 2A), pE1A-13S (FIG. 2B), pE1A-12S (FIG. 2C), and pE1Ad1346 (FIG. 2C). A constant amount (5 µg) of the pneuEcoR1-CAT construct was cotransfected into Rat-1 cells with 5, 10, 15, and 20 µg of the test constructs. The total amount of the transfected DNA were kept constant by adding the appropriate amount of carrier DNA pSP64. The relative CAT activities without E1A (lanes 0 in FIGS. 2A–2D) are defined as 100%. The relative CAT activities with 5, 10, 15 and 20 µg of test constructs are as follows: E1A, 68%, 35%, 26%, 17%; E1A-13S, 72%, 48%, 36%, 24%; E1A-12S, 66%, 46%, 28%, 21%; E1Ad1346, 102%, 103%, 99%, 102%, (FIG. 2E). Summary of the effects of different E1A mutants on transient expression from the neu promoter. Schematic structures of the proteins encoded by different E1A mutants are shown on the bar diagram. Hatched areas represent the conserved protein regions of the E1A products. Bar diagrams are not drawn to scale.

To further study the interactions of E1A genes products with the neu promoter, increasing amounts of pE1A were cotransfected with pneuEcoR1-CAT in ratios of 1:1, 2:1, 3:1, and 4:1 (FIG. 2A). Inhibition of the gene expression directed by the neu promoter was found to be dependent on pE1A concentration, and 50% repression could be observed at as low as a 1:1 ratio of pE1A:pneuEcoR1-CAT.

Figure 2B:
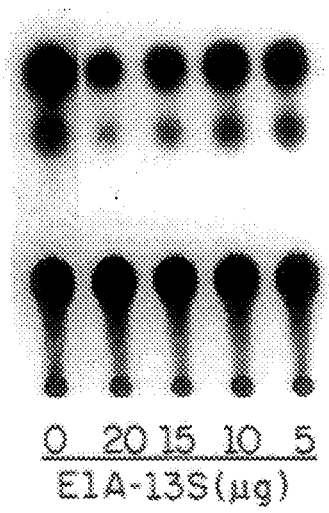
Figure 2C:
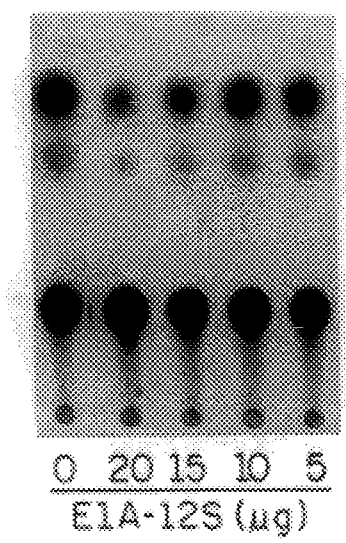

The Ad5 E1A gene produces two major spliced products, the 12S and 13S mRNAs, that encode proteins 243 and 289 amino acids long, respectively (Moran et al., 1987). To determine which E1A gene product was responsible for the observed repression, the same studies were performed with recombinant plasmids expressing either 12S or 13S E1A gene product (pE1A-12S and pE1A-13S). As shown in FIGS. 2B and 2C, both the 12S and 13S products were effective at repressing neu transcription in a concentration-dependent manner.

The E1A gene products contain three highly conserved regions; CR1, CR2, and CR3 (Moran et al., 1987; Van Dam et al., 1989). CR1 and CR2 exist in the 12S and 13S, whereas CR3 is unique to the 13S product. Since 12S itself can repress neu efficiently, the inventors reasoned that the CR3 is dispensable for transcriptional repression of neu by E1A.

Figure 2D:
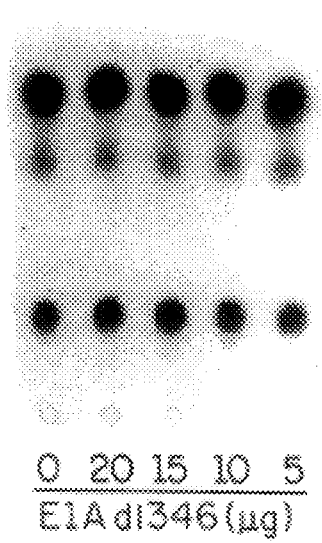
Figure 2E:
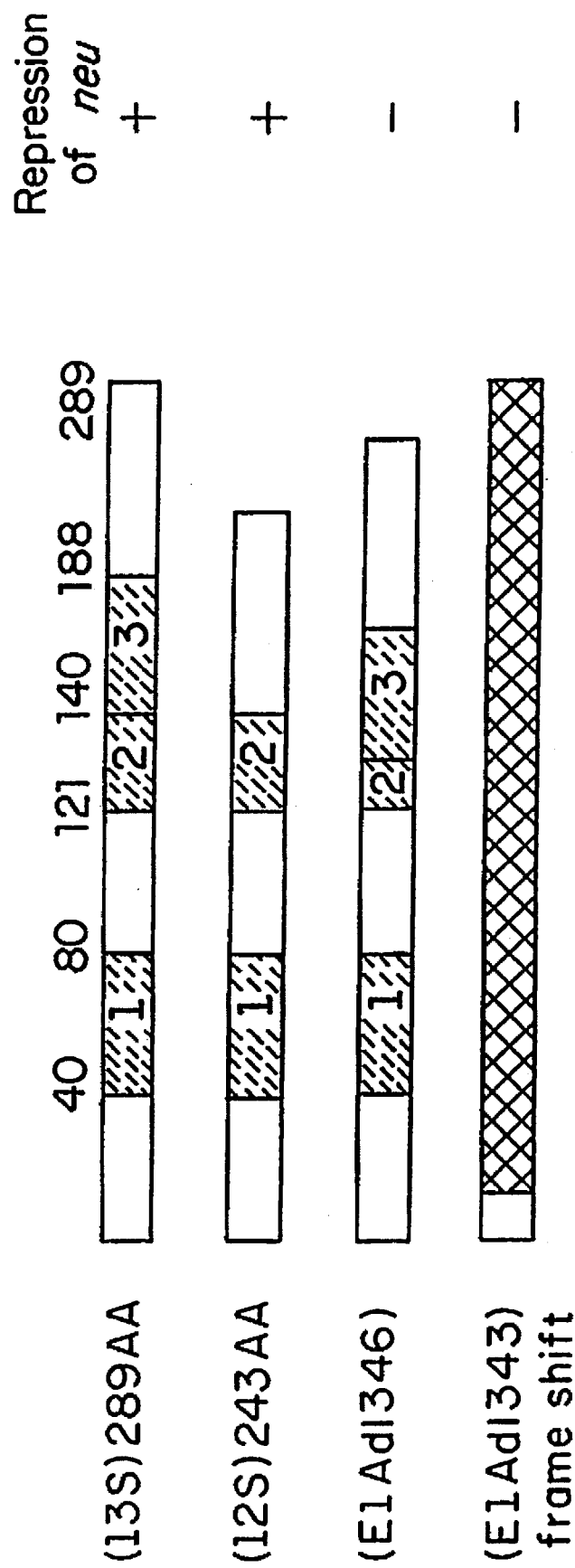
Figure 3A:
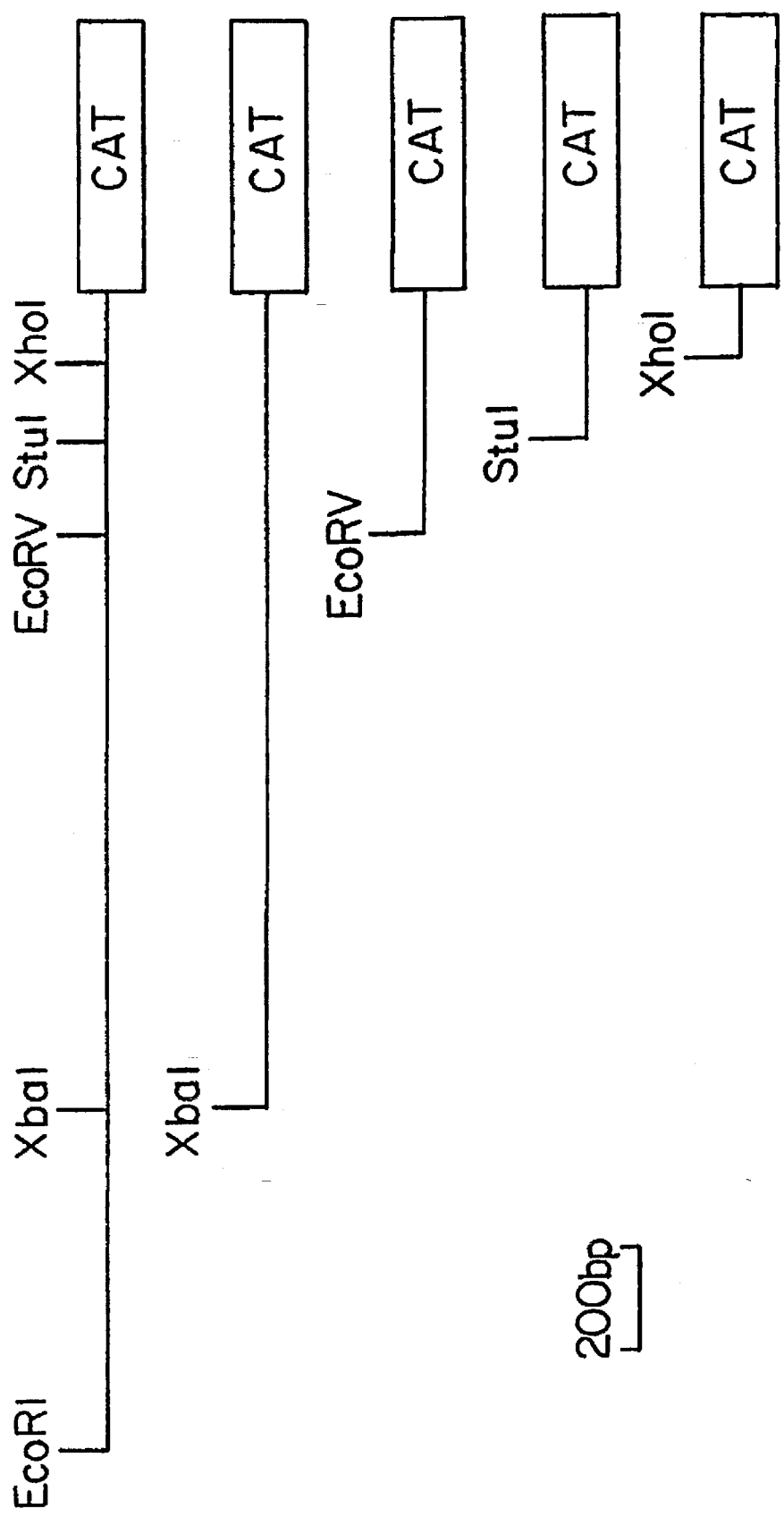
FIGS. 3A and 3B show localization of E1A-responsive DNA element in the upstream region of neu promoter.
Figure 3B:
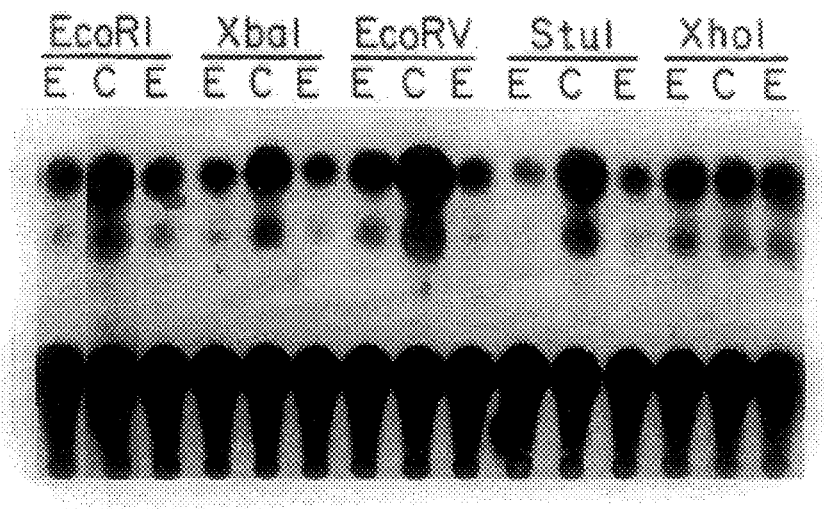

To further localize whether the CR1 or the CR2 in the E1A protein was required for efficient repression of neu, parallel studies were performed using deletion mutants pE1Adl343 and pE1Adl346 (Hearing et al., 1985). The pE1Adl343 mutant contains a 2-bp deletion in the E1A coding sequence, resulting in a frame shift in all three conserved regions of the E1A products and leaving only the N-terminal 40 amino acids intact. No effect on CAT activity was observed when pE1Adl343 mutant was cotransfected with pneuEcoR1-CAT. The pE1Adl346 mutant containing an in-frame deletion, which removed 16 amino acids within the CR2 but reserved the CR1, failed to express neu transcription (FIG. 2D). The inventors concluded that the CR2 of E1A gene products is required for efficient transcriptional repression of neu (FIG. 2E).

c. Localization of Target DNA Element in the neu Promoter Responding to E1A Repression To localize the DNA element in the neu promoter that mediates the transcriptional repression by the E1A products, a series of 5' deletion constructs containing portions of the neu promoter linked to a functional CAT gene were cotransfected with pE1A into Rat-1 cells (FIG. 3A). The transient expression of the CAT gene driven by each of these promoter fragments after transfection with control plasmid vector pSP64 or with pE1A in a ratio of 1:2 is shown in FIG. 3B. Only the pneuXhoI-CAT containing the smallest promoter fragment was not repressed by E1A. Clearly the activity of a site within the Stu I-Xho I restriction fragment is sensitive to E1A repression. This Stu I-Xho I fragment is sensitive to E1A repression. This Stu I-Xho I fragment is located between −198 and −59 with respect to the transcriptional start site of neu. The inventors concluded that the target DNA element responding to E1A repression resides inside this 139-bp Stu I-Xho I fragment.

d. Evidence for the Involvement of Trans-Acting Factor(s)

Figure 4B:
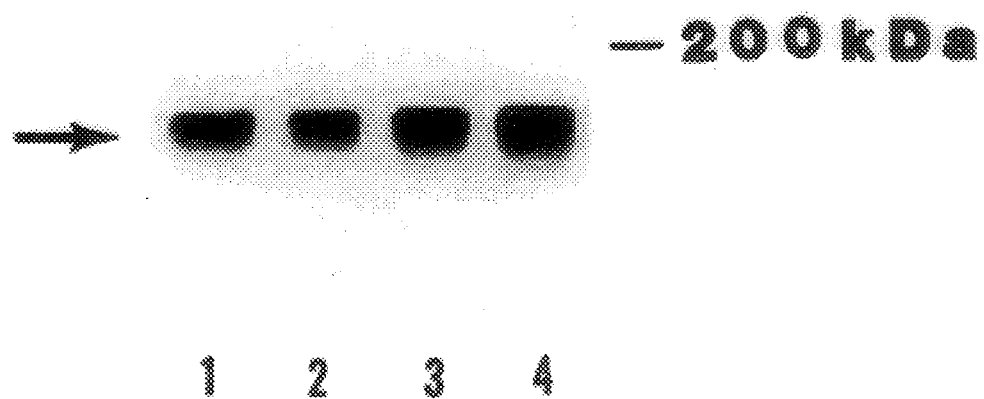
FIGS. 4A and 4B show derepression of neu by cotransfection of competing amounts of Stu I-Xho I neu promoter fragments.
Figure 4A:
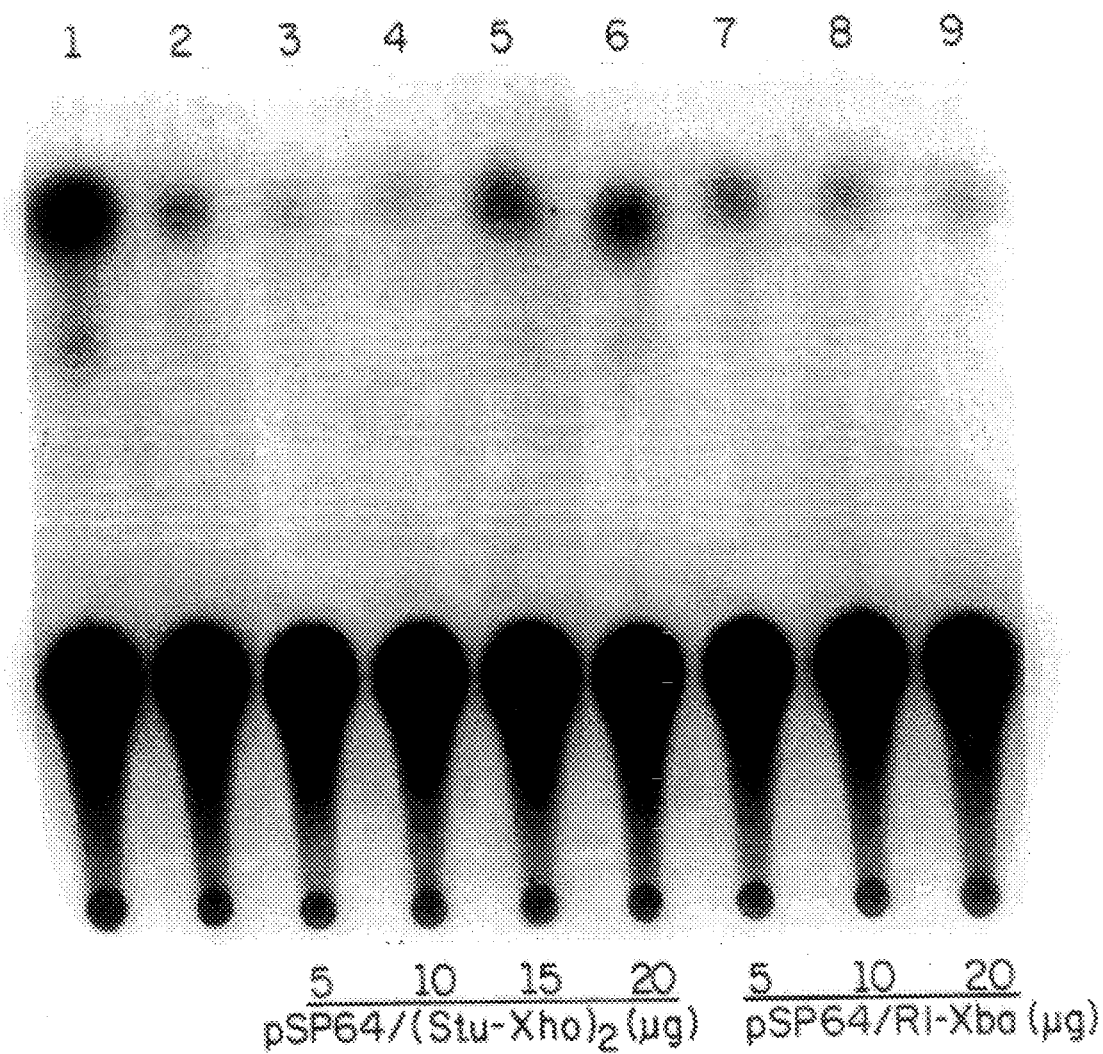

To examine whether this repression by the E1A products is a trans-acting process, the inventors attempted to remove the repression by cotransfecting a third recombinant, pSP64/Stu-Xho, containing only the Stu I-Xho I restriction fragment cloned in pSP64. Increasing amounts of pSP64/Stu-Xho, in cotransfections in which transcription of pneuEcoR1-CAT was repressed by pE1A, relieved the repression of neu transcription in a concentration-dependent manner (FIG. 4A). In contrast, no derepression was observed when pSP64/RI-Xba containing the EcoRI-XBA I restriction fragment cloned in pSP64 was cotransfected. The derepression was effective at a 4:1 ratio of pSP64/Stu-Xho:pneuEcoR1-CAT (FIG. 4A, lane 6), indicating that the Stu I-Xho I fragment can efficiently compete with the neu promoter for the transcription factor(s) involved in the repression of neu by E1A. These results confirm that the target for the E1A repression in the Neu promoter is a cis DNA element within the Stu I-Xho I fragment of this promoter. Furthermore, this repression of transcription may involve an interaction between the DNA element and either the E1A products or some cellular transcription factors(s) interacting with or induced by the E1A products.

e. Repression of Human neu Expression in SK-BR-3 Cells

Comparison of the Stu I-Xho I fragment of rat neu promoter sequence with its counterpart sequence in human neu promoter (Tal et al., 1982) reveals >86% homology. It was suspected by the inventors that the human neu gene might also be repressed by E1A at transcriptional level by way of similar mechanisms. If this is the case, cotransfection of the Stu I-Xho I fragment of rat neu promoter might be able to relieve the repression of human neu incurred by E1A.

To test this possibility, cotransfection studies were carried out by using as recipient cells human breast cancer cell line Sk-Br-3, which is known to overexpress human neu mRNA and p185 proteins (Kraus et al., 1987). Immunoblotting studies with SK-BR-3 cell lysates showed that the expression of human neu gene products, the p185 protein, was reduced by introduction of E1A (FIG. 4B, compare lane 1 with lane 4). Cotransfection of pSP64/R1-Xba plasmids with pE1A at a 4:1 ratio was ineffective in removing the repression of p185 expression by E1A, whereas cotransfection of pSP64/Stu-Xho with pE1A at the same ratio relieved the repression by E1A.

It is known that the maximum efficiency of transient transfection can reach only 50% (Chen et al., 1988); the other 50% of nontransfected Sk-Br-3 cells should still produce high levels of p185 proteins, which can result in high background in the E1A-mediated repression of p185. Therefore, the repression effect on the endogenous neu-encoded p185 by transiently transfected E1A in the immunoblotting assay was not as dramatic as that observed in CAT assays. However, the small difference was detected reproducibly. The best interpretation of the results is that E1A can repress human neu promoter at transcriptional level by targeting at the cis-acting DNA element in human neu promoter corresponding to the Stu I-Xho I fragment of rat neu promoter.

f. The Sequence TGGAATG is an Important Site for the E1A-Mediated Repression

E1A has been reported to repress enhancer mediated transcription activation of simian virus 40 (Borrell et al., 1984), polyomavirus (Velcich et al., 1986), immunoglobulin heavy chain (Hen et al., 1985), and insulin genes (Stein et al., 1987). Comparison of the enhancer sequences of these genes reveals a consensus sequence (shown overleaf), which is likely to be the core sequence of the E1A-responding element.

However, there has been no experimental evidence to support this notion. A sequence, TGGAATG, that matches the consensus sequence has been fund in the Stu 1-Xho 1 E1A-responding element of the rat neu promoter. An identical sequence also exists in the corresponding region of the human neu promoter (Tal et al., 1987). It is therefore conceivable that the sequence TGGAATG may be an important target sequence for the E1A-induced repression.

Figure 5:
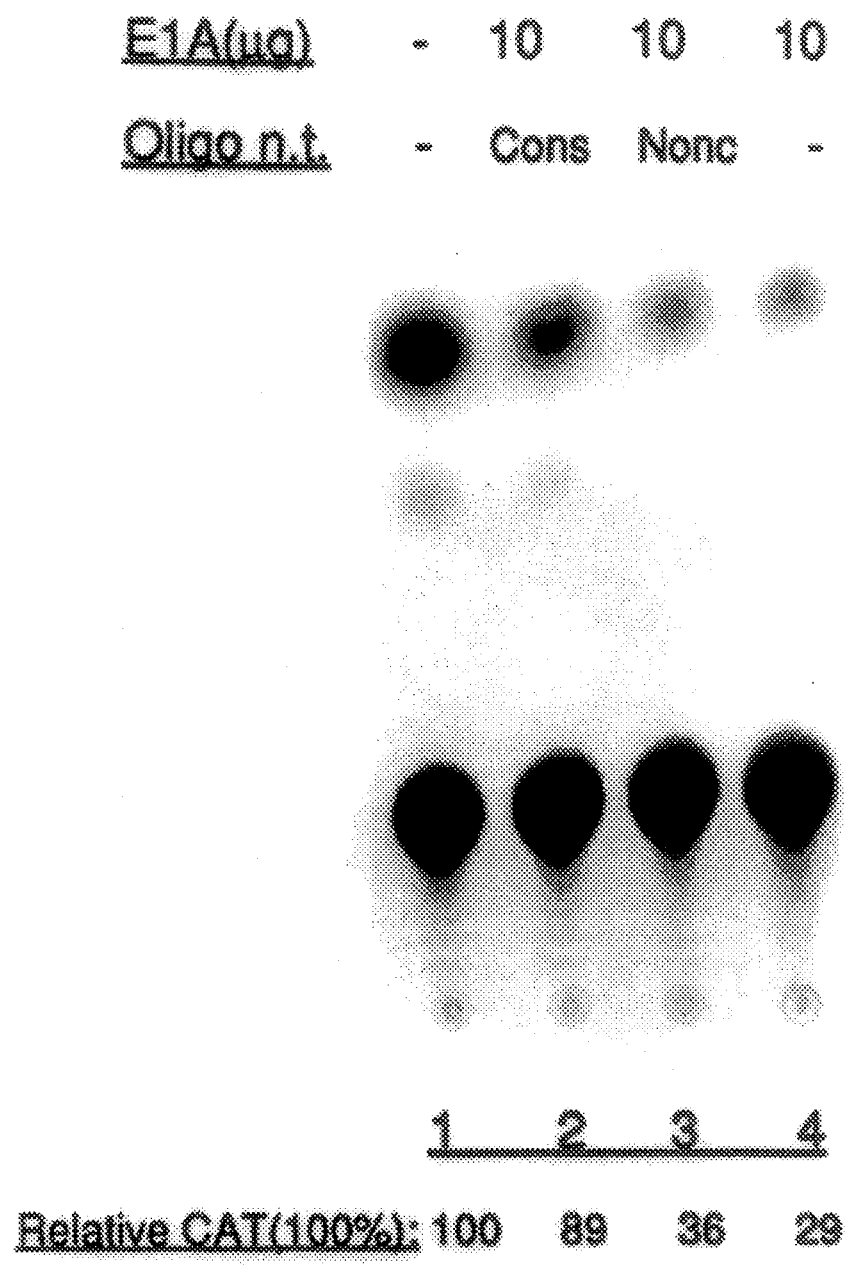
FIG. 5 shows removal of the E1A-mediated repression of neu by cotransfection of a 20-mer oligonucleotide containing the consensus sequence. Rat-1 cells were transfected with 3 µg of pneuEcoRV-CAT plasmids, giving basal neu promoter activity (lane 1); CAT activity after cotransfection with 10 µg of pE1A is shown in lane 4. Two micrograms of the 20-mer double-stranded oligonucleotide containing the consensus sequence (lane 2, Cons) was cotransfected with pneuEcoRV-CAT and pE1A (molar ratio of oligomer:pNeuEcoRV-CAT=35:1), resulting in significant derepression; cotransfection of 2 µg of a 22-mer random nonhomologous oligonucleotide with pneuEcoRV-CAT and pE1A had no significant derepression effect (lane 3, None). The values for relative CAT activity are the average of three studies. The upper strand sequence of the synthetic 20-mer oligonucleotide is shown at the bottom (SEQ ID NO:1); the proposed E1A-responding sequence is underlined.

To investigate this possibility, a 20-mer oligonucleotide from the rat neu promoter containing the sequence TGGAATG was synthesized (FIG. 5). This oligonucleotide efficiently competed with the neu promoter for the transcriptional factors(s) involved in the repression of neu by E1A, resulting in a derepression effect (FIG. 5, lane 2), whereas a 22-met random nonhomologous oligonucleotide had no derepression effect (FIG. 5, lane 3). These data provide experimental evidence that the 20-mer oligonucleotide harbors a critical sequence required for the E1A-induced inhibition. Since the sequence TGGAATG within this 20-mer oligonucleotide resembles the consensus sequence in the enhancer sequences of other genes that can be repressed by E1A, it is likely that this 7-bp sequence is the critical sequence that is mediating the E1A effect.

3. Discussion

The foregoing results show that in a cotransfection system, the E1A gene products repressed the neu expression at the transcriptional level. It is further demonstrated that the repressive effect on neu expression is lost in E1A products when part of the CR2 (amino acids 120–136) is deleted. Notably, a structure motif in this deleted part of the adenoviral E1A CR2 region is shared among the papovaviral large tumor antigens, the v- and c-myc oncoproteins, the E7 transforming proteins of human papilloma viruses, and the yeast mitotic regulator DCD25 gene product (Figge et al., 1988). This region encoding the shared motif is also required by E1A, simian virus 40 large tumor antigen, and human papilloma viruses 16 E7 for their specific binding to the human retinoblastoma gene product, RB protein (Whyte et al., 1988; Whyte et al., 1989).

These studies further elucidate the oligonucleotide sequence mediating E1A-induced repression in the upstream region of neu promoter. The sequence TGGAATG is perfectly conserved between rat and human neu promoter, which is indicative of functional importance. In addition, this sequence matches the consensus sequence of other genes that can also be repressed by E1A at transcriptional level. Taken together, these findings suggest that there may be common mechanisms involved in this type of E1A-mediated repression. It has been proposed that E1A may form a complex with cellular transcription factor(s) and thereby modulate the specific binding of the transcription factor(s) to enhancer elements that are important for transcription (Mitchell et al., 1989). Identification of the defined DNA sequences responsible for the E1A-mediated inhibition of neu transcription will allow us to identify the transcription factor(s) involved in this process.

The neu protooncogene is notably amplified in patients with metastatic breast cancer. Expression of the E1A gene can inhibit experimental metastasis of ras oncogene-transformed rat embryo cells. Here, it is shown that neu transcription can be repressed by E1A products in an established rat embryo fibroblast cell line, Rat-1. Furthermore, the inventors have found that in SK-BR-3 human breast cancer cells expression of the p185 protein, the human neu gene product, was reduced by introduction of E1A gene. The derepression effect observed in the cotransfection experiment with the Stu 1-Xho 1 fragment has demonstrated that this reduction of p185 proteins is likely due to the similar transcriptional repression mechanisms.

EXAMPLE II

Adenovirus-5 E1A Gene Products Act as a Transformation Suppressor of Neu Oncogene In Example I, transcription of the neu protooncogene was shown to be strongly repressed by adenovirus-5 E1A gene products through the use of a transient transfection assay. In the present Example, the E1A gene has been stably introduced into the neu-transformed B104-1-1 cells, to demonstrate that E1A-mediated neu repression can suppress neu-mediated transforming activity. In these studies, cells that expressed E1A products possessed reduced transforming and tumorigenic activity, as evidenced using standard assays for each. These results demonstrated that E1A gene products can act negatively to suppress the transforming phenotype of the neu oncogene, and is believed to be the first example of a gene, i.e., the E1A gene, that can act in one setting as a transforming oncogene, and in another as a transforming suppressor gene.

The B104-1-1 cell line, an NIH3T3 transfectant that has approximately 10-20 copies of mutation-activated genomic neu oncogene has been shown to be highly transforming and tumorigenic (Bargmann et al., 1986; Stern et al., 1986). For the present studies, B104-1-1 cells and control NIH3T3 cells were transfected with either E1A plasmids expressing adenovirus-5 E1A gene, (pE1A), or a derivative plasmid containing only the E1A promoter without the E1A coding sequence (pE1Apr). Cells were cotransfected with pSV2neo plasmids carrying a neomycin resistant marker gene (Southern et al., 1982).

The transfections were carried out with the modified calcium phosphate precipitation procedure of Chen and Okayama (1988). In each transfection, $5 \times 10^5$ B104-1-1 cells or NIH3T3 cells (2×10 cm dishes) were seeded 24 h before transfection. The cells were transfected with either 10 μg of the E1A expressing pE1A plasmid DNA or its derivative pE1Apr plasmid DNA, along with 1 μg of pSV2-neo plasmid DNA (Southern et al., 1982). Approximately 14 h post-transfection, cells were washed and cultured in fresh medium for 24 h and split at a 1:10 ratio. The cells were then grown in selection medium containing 500 μg/ml of G418 for 2-3 weeks and individual G418 resistant colonies were cloned using cloning rings and expanded to mass culture.

Three kinds of stable transfectants were thus established: (1) B-E1A transfectants: B104-1-1 transfectants harboring the E1A gene; (2) B-E1Apr transfectants: B104-1-1 transfectants containing E1A promoter sequence, which is used as a control cell line in this study; and (3) N-E1A transfectants: NIH3T3 cells transfected with the E1A gene.

Cells cultures were performed as described previously (Hung et al., 1989; Matin et al., 1989). The B104-1-1 cell line and NIH3T3 cell line were grown in Dulbecco's modified Eagle's medium (DMEM) supplemented with 10% calf serum in a humidified atmosphere at 5% $CO^2$ at 37° C. The B-E1A transfectants and N-E1A transfectants were grown under the same condition with addition of G418 (500 μg/ml) into the culture media.

FIGS. 6A-6D shows the molecular characterization of the representative stable transfectants used in this study, employing both Southern blot and immunoblot analyses. Southern blot analyses were performed essentially by published techniques as previously described (Zhang et al., 1989). Genomic DNAs extracted from cultured cells were digested overnight at 37° C. with a 2-fold excess of a restriction endonuclease (either EcoR1, Sst1, or BamH1). Ten μg of each sample were then resolved by electrophoresis on a 1% agarose gel and transferred to Nytran membrane (Schleicher & Schuell, Keen, N.H.) using a 10×SSC (1.5 m NaCl, 0.15M sodium citrate). The blotted DNA were hybridized under high stringent conditions (68° C.) with [$^{32}$P] radioactive probe ($1-5 \times 10^8$ CPM μg$^{-1}$) labeled by using Random Primed DNA Labeling Kit (Boehringer Mannheim Biochemicals, Indianapolis, Ind.). The blots were washed twice for 15 min each in 2×SSC, 0.1% SDS at room temperature, and then twice for 30 min each in 0.1×SSC, 0.1% SDS at 68° C. with constant agitation. The filters were dried at room temperature and then exposed to Kodak X-OMAT™ AR film at −80° C. for 1 to 3 days.

Immunoblot analysis were performed basically by published techniques (Towbin et al., 1979) as previously described (Matin et al., 1990). Confluent cells growing in 10 cm plates were lysed with RIPA-B buffer (20 mM sodium phosphate, pH 7.4, 150 mM NaCl, 5 mM EDTA, 1% Triton, 10 μg/ml Aprotinin, 2 mM PMSF, 10 μg/ml Leupeptin and 4 mM iodoacetic acid) and then centrifuged at 10×g for 20 min at 4° C. The protein concentration of the supernatants was determined by Bio-Rad protein assay (Bio-Rad Laboratories, Richmond, Calif.). 50 μg of each sample were subjected to SDS polyacrylamide gel electrophoresis (10%) and transferred to nitrocellulose. The nitrocellulose filters were treated with 3% nonfat dry milk in TPBS buffer (0.05% Tween-20, 138 mM NaCl, 2.7 mM KCl, 4.3 mM Na2HPO4.7H$_2$O and 1.4 mM KH$_2$PO4) for 1 h at room temperature, followed by an overnight incubation at 4° C. with primary monoclonal antibodies M73 against the E1A proteins (a gift of Dr. L. S. Chang, Ohio State Univ.) or mAb-3 against the neu encoded p185 protein (purchased from Oncogene Science Inc., Manhasset, N.Y.). After three 10 min washes with TPBS buffer, the nitrocellulose was then incubated for 1 h at room temperature with 1:1000 dilution of horseradish peroxidase-conjugated goat anti-mouse immunoglobulin (Bio-Rad Laboratories). The nitrocellulose filters were washed 3 times in TPBS buffer and were subjected to color developing reaction with horseradish peroxidase substrate (Kirkegaard & Perry Laboratories, Inc., Gaithersburg, Md.).

Figure 6A:
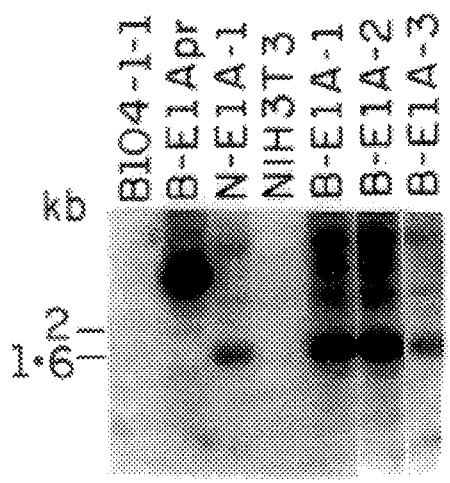
FIGS. 6A–6D show E1A gene presence and protein production in cells.
Figure 6B:
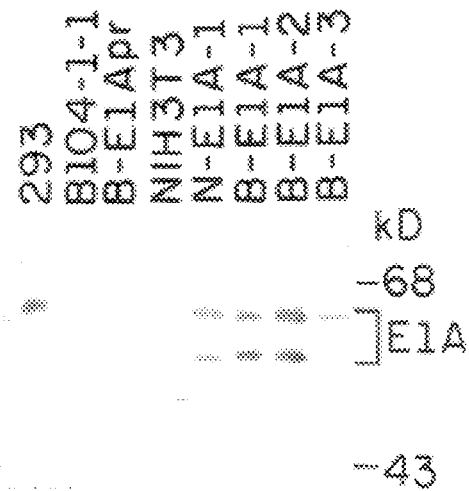

To assure that the exogenous E1A gene or E1A promoter DNA had integrated into the genome of the transfectants, DNA blot analysis with the E1A probe was performed and the results confirmed the integration of transfected foreign DNA (FIG. 6A). Noticeably, the three B-E1A transfectants studied (B-E1A-1, B-E1A-2 and B-E1A-3) acquired different copy numbers of the E1A gene. Immunoblot detection of E1A further confirmed that the B-E1A and N-E1A transfectants actually produced E1A proteins and the E1A protein levels in these transfectants are lower than that in the 293 cell line, an established cell line of primary human embryonal kidney transformed by adenovirus DNA. (FIG. 6B).

Figure 6C:
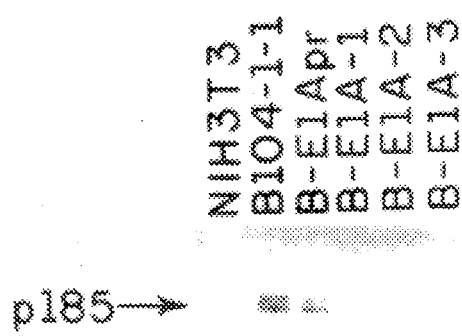
Figure 6D:
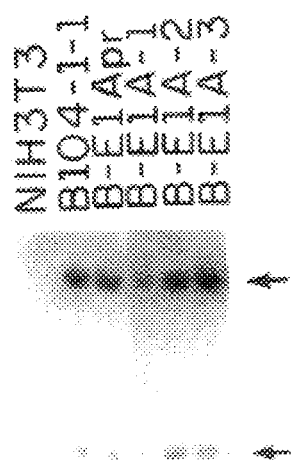
Figure 7A:
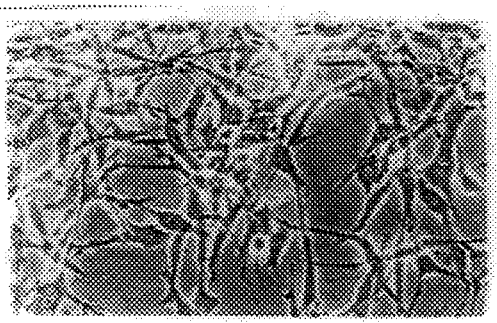
FIGS. 7A–7F show morphologic effects of E1A expression in neu-transformed B104-1-1 cells.
Figure 7B:
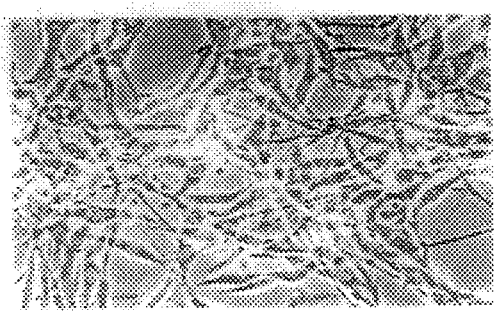
Figure 7C:
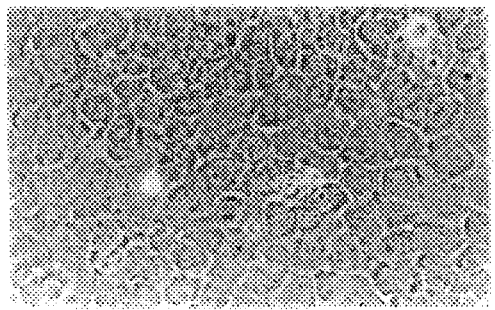
Figure 7D:
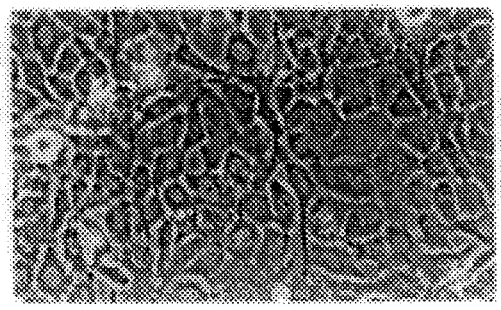
Figure 7E:
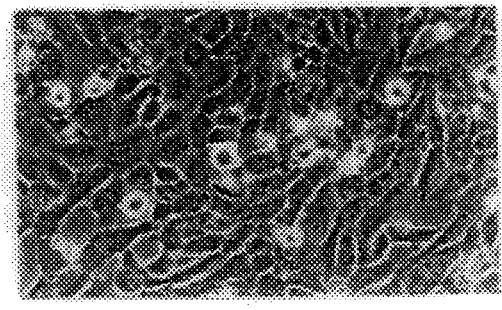
Figure 7F:
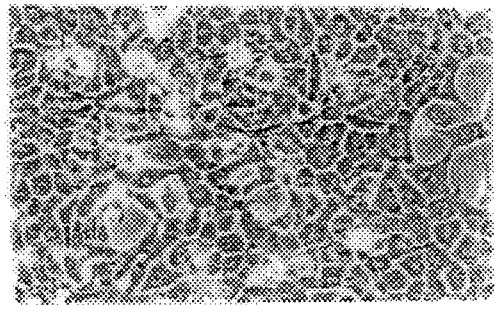

To examine if expression of E1A can inhibit neu expression, immunoblot analysis for the neu-encoded p185 protein was also performed and the p185 proteins were virtually undetectable in all the transfectants using horse radish peroxidase detection method (FIG. 6C). However, slightly higher levels of p185 proteins could be detected in B-E1A-3 than those in B-E1A-1 and B-E1A-2 when the more sensitive $^{125}$I-protein-A detection method was used. Since p185 proteins were barely detectable in B-E1A transfectants, DNA blot analysis for rat neu gene was conducted to make sure that the neu gene was not lost. As shown in FIG. 6D, the incorporation of E1A gene into the genome did not alter the neu gene at the DNA level.

Among the three B-E1A transfectants, B-E1A-2 and B-E1A-3 had levels of the neu gene that were comparable to those of the parental B104-1-1 cell line; while B-E1A-1 appeared to have a lower level neu gene. This may be due to partial loss of the neu gene in this line during the establishment of this transfected cell line. The three B-E1A transfectants shown in FIG. 6 were chosen for further transformation assay because they represented three different subtypes of B-E1A transfectants: (1) B-E1A-1 had fewer copies of neu gene compared to B104-1-1 and more copies of E1A gene; (2) B-E1A-2 retained the same level of neu as B104-1-1 and high levels of E1A gene; (3) B-E1A-3 contained the same amount of neu as B104-1-1, but a low quantity of the E1A gene.

The transforming phenotype of the neu-transformed cells usually includes a transformed morphology, non-contact-inhibited growth pattern, increased DNA synthesis rate, anchorage-independent growth and the ability to induce tumors in nu/nu mice. To determine the effect of E1A expression on the transforming ability of neu-transformed B104-1-1 cells, the B-E1A transfectants as well as the control cell lines were assayed for all the above mentioned transforming parameters using standard protocols.

The results of these studies demonstrated that the highly transformed morphology of B104-1-1 cells was essentially unchanged after pE1Apr transfection but was markedly altered by pE1A transfection (FIGS. 7A–7F). The B-E1A transfectants exhibit non-transformed flattened morphology and a contact-inhibited growth pattern (FIGS. 7A–7F). Expression of E1A proteins in NIH3T3 cells did not significantly alter the monolayered morphology. The results indicated that E1A gene products could specifically reverse the transforming morphology of the neu-transformed cells.

DNA synthesis was also studied as a measure of cell growth, to determine whether the B-E1A transfectants were actively synthesizing DNA as compared to controls. These studies were conducted through the use of a [$^3$H]-thymidine incorporation assay. For these studies, cells were plated in ten replica into 96 well plates at a density of $9\times10^3$ cells/well and cultured in DMEM supplemented with 10% calf serum. [$^3$H]-thymidine (1 μCl) was added to each well at time points of 16, 40 and 64 h and continuously incubated at 37° C. for 2 h. Cells were then harvested and cellular DNA were bound to glass fiber filters. Radioactivities of individual samples were counted by Scintillation counter. Average cpm were calculated from ten replicate samples.

Figure 8A:
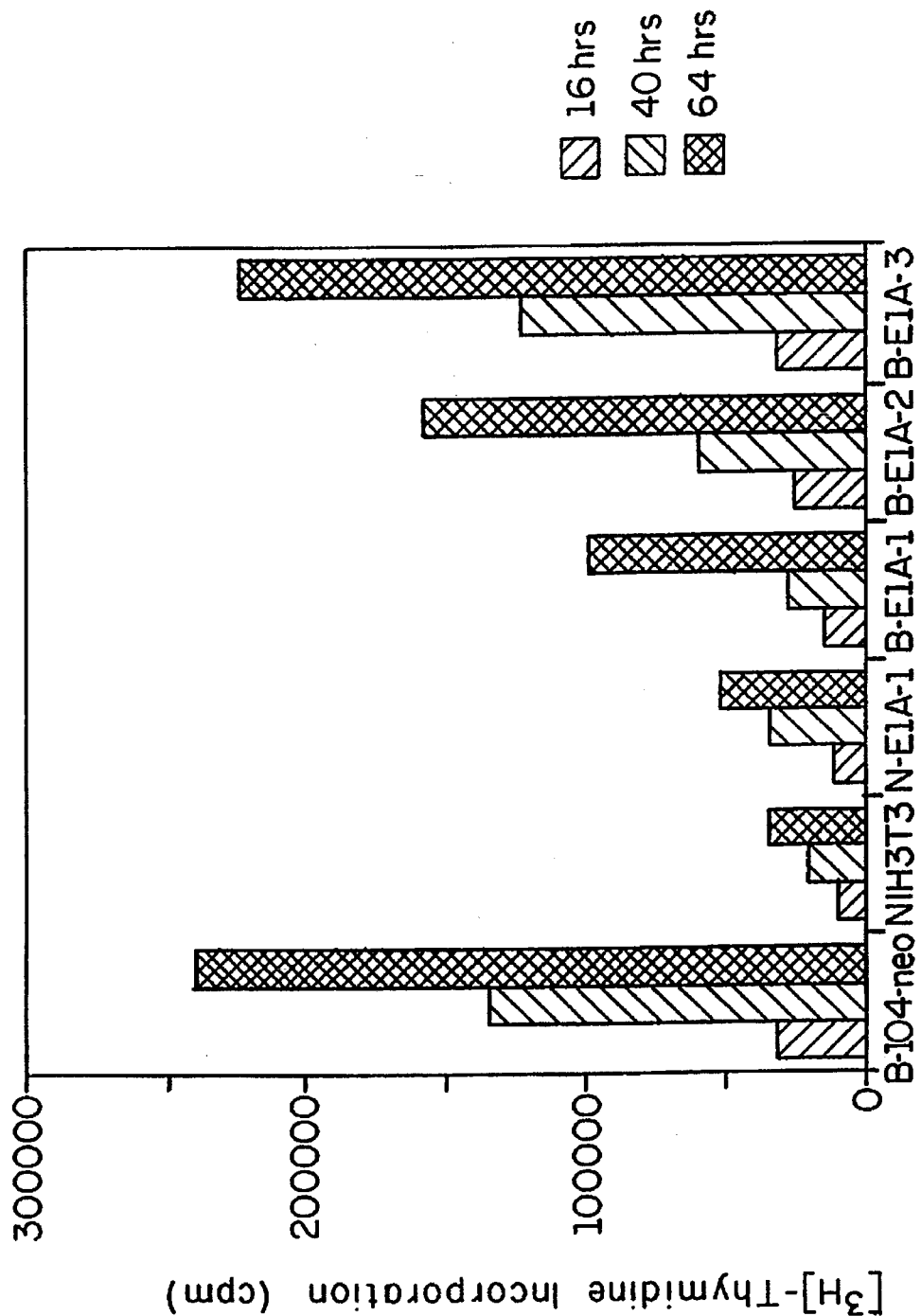

The rate of DNA synthesis, as indicated by [$^3$H]-thymidine incorporation, was different among the three B-E1A transfectants (FIG. 8A). B-E1A-1 and B-E1A-2 displayed a much lower DNA synthesis rate, which coincided with their slower cell growth rate compared to B104-1-1 cells. This E1A-induced decrease in [$^3$H]-thymidine incorporation was not as dramatic in the B-E1A-3 cell line possibly due to the lower level of the E1A proteins. These data suggested that E1A proteins can inhibit the effect of the neu oncogene on DNA synthesis and cell growth.

To test the influence of the E1A proteins on anchorage-independent growth, B104-1-1 cells and the B-E1A transfectants were assayed for their ability to grow in soft agar. The ability of B104-1- cells, B-E1A transfectants, NIH3T3 cells and N-E1A transfectant to grow in soft agarose was determined as described previously (Matin et al., 1990). Cells ($1\times10^3$ cells/plate) were plated in a 24 well plate in DMEM containing 10% calf serum and 0.35% agarose (BRL, Gaithersburg, Md.) over a 0.7% agarose lower layer. The cells were incubated at 37° C. for 3 weeks and the plates were stained with p-iodonitrotetrazolium violet (1 mg/ml) for 24 h at 37° C. and colonies were counted.

Figures 8B, 9B:
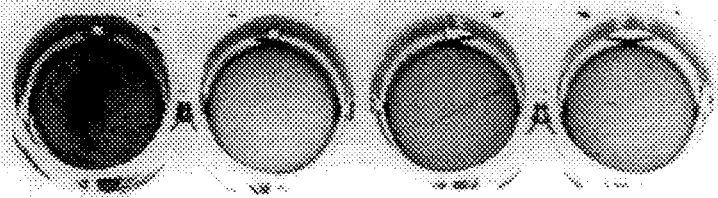

The results of the soft agar studies demonstrated that colony formation by the E1A transfectants were strikingly reduced compared to that of B104-1-1 and B-E1A pr transfectants (FIG. 8B). It is noteworthy that the colony formation by NIH3T3 and N-E1A-1 lines did not vary significantly.

The most stringent experimental test for neoplastic behavior is the ability of injected cells to form tumors in nude mice. Studies in nude mice were conducted because the examination of E1A repression of neu-mediated tumorigenicity in vivo was considered to be a critical test of E1A effectiveness. For conducting tumorigenicity studies, the B104-1-1 cells, B-E1A transfectants, NIH3T3 cells and N-E1A transfectant in log-phase growth were trypsinized and washed twice with phosphate buffered saline and centrifuged at 250×g. The viable cells were then counted, and $1\times10^5$ cells in 0.1 ml of phosphate buffered saline were injected subcutaneously into both the right and left flanks of 5 to 6-week old female homozygous nu/nu (nude) mice (Harlan Sprague Dawley Co.) under sterile conditions. Tumor formation was scored at indicated days as presence or absence of a visible tumor mass. Sixteen days after injection, tumor volumes were estimated as the product of three-dimensional caliper measurements (longest surface length and width and tumor thickness). The growth of tumors was monitored for a minimum of 16 days and maximum of 2 months.

When cells of the parental B104-1-1 line were injected subcutaneously in nude mice, solid tumors developed by 8 days after injection; however, the same quantity of the E1A transfectants did not form tumors in nude mice until 12–26 days after injection and in every case the tumors were much smaller than those from B104-1-1 cells (FIG. 9A).

Figure 11A:
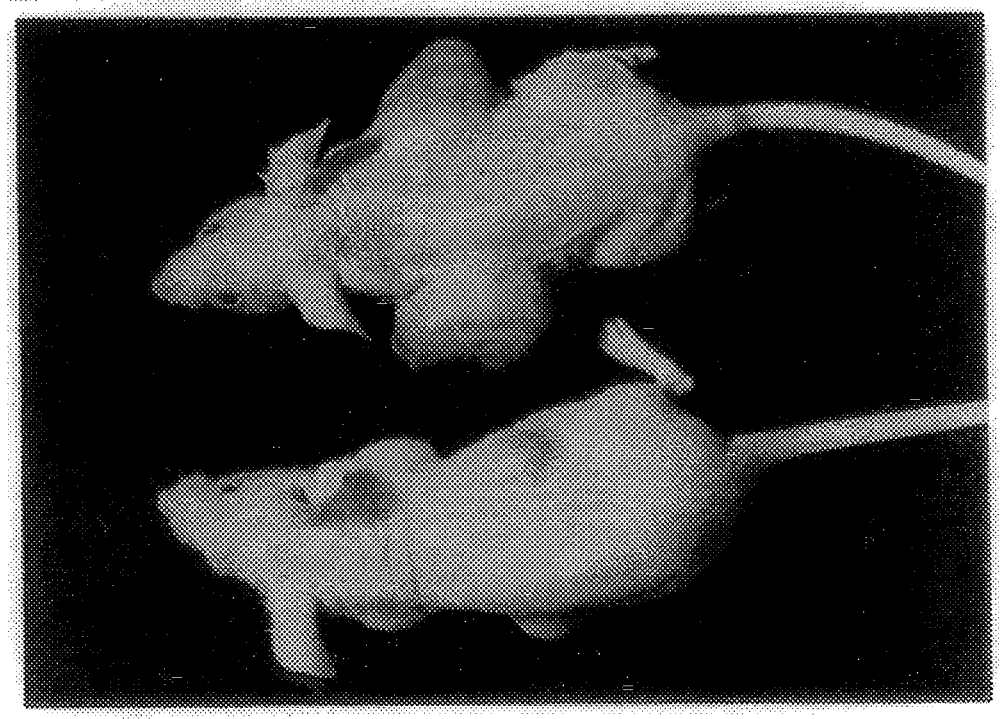
FIGS. 11A and 11B show that E1A suppresses neu-induced tumor formation and metastasis in vivo in nude mice.

Although the B-E1A-1 and B-E1A-2 transfectants contained comparable amounts of the E1A gene, the B-E1A-1 cells did not cause tumor development until a much later time. This is probably due to the lower level of neu gene in this line. On the other hand, although both of the B-E1A-2 and B-E1A-3 transfectants contained the same level of the neu gene as B104-1-1, the transforming suppression effect on B-E1A-3 was not as strong as on B-E1A-2. This was likely due to the lower level of the E1A gene in B-E1A-3. Typical results of E1A expression on neu oncogene induced tumorigenicity are shown in the photographs in FIGS. 9B and 11A. Evaluated 18 days after injection, animals injected with B104-1-1 cells were found to bear huge tumors, whereas those injected with B-E1A-2 transfected cells had considerably smaller tumor nodules. As expected, control animals injected with NIH3T3 cells showed no evidence of tumor formation.

Previous studies of Wilms' tumor cells and human prostate carcinoma DU145 cells demonstrated that reintroduction of chromosome 11 to Wilm's tumor cells or restoration of RB gene to DU145 cells suppressed tumor formation but did not alter the cell morphology, growth rate or colony-forming ability (Weissman et al., 1987; Bookstine et al., 1990). These data suggest that growth rate in culture and tumorigenicity in nude mice are separable phenomena. In the present study, the B-E1A-1 and B-E1A-2 cells exhibited slower growth rate and much weaker tumorigenic activity. However, suppression of tumorigenicity cannot entirely be explained by their slower growth rate and decreased [$^3$H]-thymidine incorporation. For example, the B-E1A-3 cells possessed similar [3H]-thymidine incorporation and cell growth rate as B104-1-1 cells, while their tumorigenic activity was markedly suppressed as well. Taken together, these results clearly demonstrate that introduction of the E1A gene into B104-1-1 cells suppresses all the transforming properties of the neu-transformed cells.

EXAMPLE III

Suppression of Neu-Mediated Metastasis by E1A Gene Products

Additional studies were conducted using B-E1A transfectants of B104-1-1 to demonstrate that E1A products also suppress neu-mediated metastasis. These studies employed B-E1A transfectants (B-E1A-1 through B-E1A-5) as well as the negative and positive controls, NIH/3T3 and B104-1-1, respectively, in a cell motility, in vitro invasion and an experimental metastasis assay.

Figure 11B:
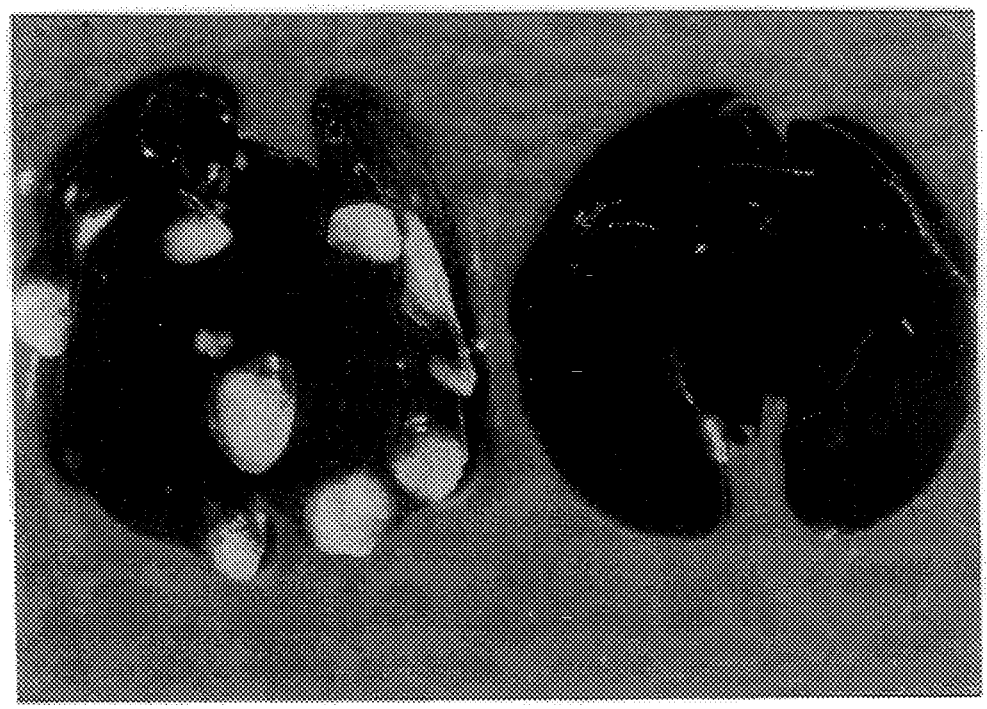

The metastasis studies were performed essentially as described by Wexler, 1966. Briefly, six-week-old pathogen-free female nude mice (Harland) were quarantined for 1 week and then used in the studies. Seven to ten mice/experimental group were inoculated with 1×10$^5$ cells/0.1 ml in PBS via the lateral tail vein at day 0. Each cell line was then assessed at two different passage numbers. Mice were sacrificed at 21 days following injection and the number of lung metastases were determined by infiltration with India ink. Only those lung nodules >1 mm in diameter were counted. On further examination, no extrapulmonary metastases were found. Representative photographs illustrating the gross appearance of the lungs from these animals are shown in FIG. 11B, whilst the quantitative data from these studies are detailed below in Table 2.

TABLE 2

EXPERIMENTAL METASTASIS ASSAY

| Cell Line | Transfected gene | Experimental metastasis Frequency | No. of lung modules (mean ± SE) |
|---|---|---|---|
| 2NIH/3T3 | — | 0/9 | 0.0 ± 0.0 |
| B104-1-1 | neu | 9/9 | 10.9 ± 10.3 |
| N-E1A | E1A | 0/8 | 0.0 ± 0.0 |
| B-neo | neu + E1A | 7/7 | 9.5 ± 7.9 |
| B-E1A-1 | neu + E1A | 0/8 | 0.0 ± 0.0 |
| B-E1A-2 | neu + E1A | 3/9 | 0.8 ± 0.4 |
| B-E1A-3 | neu + E1A | 0/8 | 0.0 ± 0.0 |
| B-E1A-4 | neu + E1A | 1/7 | 0.1 ± 0.4 |
| B-E1A-5 | neu + E1A | 1/10 | 0.1 ± 0.4 |

The effectiveness of E1A at inhibiting neu-mediated metastasis is clearly illustrated in FIG. 11B. Furthermore, this single result was found to be representative of the entire study. None of the negative control mice, NIH/3T3 and E1A transfected NIH/3T3 (N-E1A), exhibited metastatic lung nodules. However, all of the positive controls (B104-1-1 and B-neo), exhibited metastatic nodules, at a mean frequency of about 10 nodules. In contrast, all of the experimental lines (B-E1A-1 through B-E1A-5) exhibited a reduced metastatic potential, with a frequency ranging from one to three (out of ten and nine, respectively), and a mean number of 0.1 to 0.8 nodules in those animals that were positive. Note that two of the experimental lines, B-E1A-1 and B-E1A-3, were totally free of metastases.

Figure 10A:
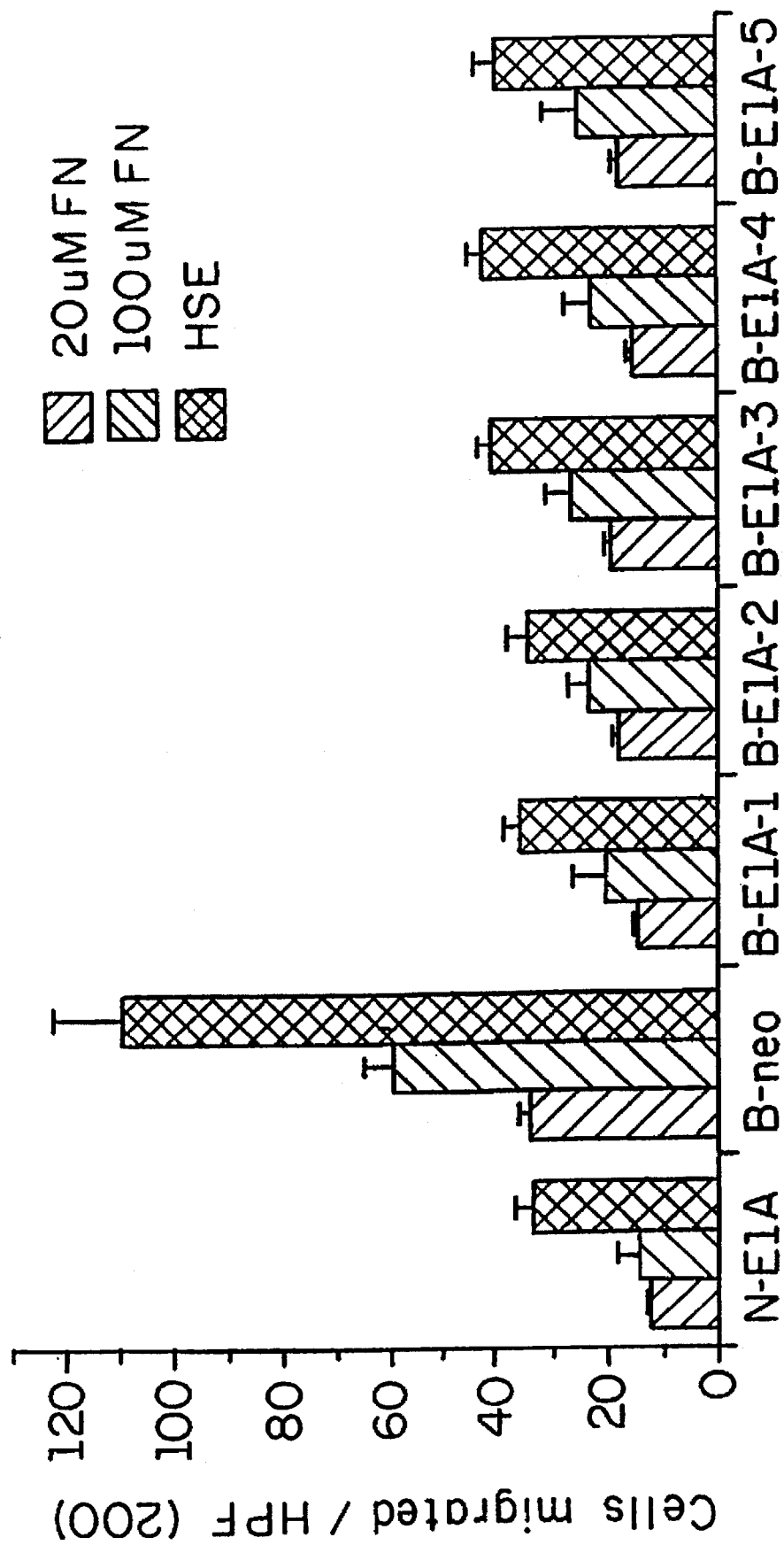
FIGS. 10A–10F show E1A inhibition of neu-transformed cells.

An increase in cell motility has been shown to correlate with a higher metastatic potential. Therefore, a motility assay, which measures the migration of the tested cell to a chemo-attractant, fibronectin or hepatic sinusoidal endothelial cell conditioned media, was performed. As shown in FIG. 10A, all of the B-E1A transfectants showed decreased migration rate to different chemoattractants than that of B-neo cell line, which are B104-1-1 cells transfected with neomycin-resistant (neo$^r$) gene alone. The N-E1A cells also had a low migration rate which is comparable to that of N1H3T3 cells.

Figure 10B:
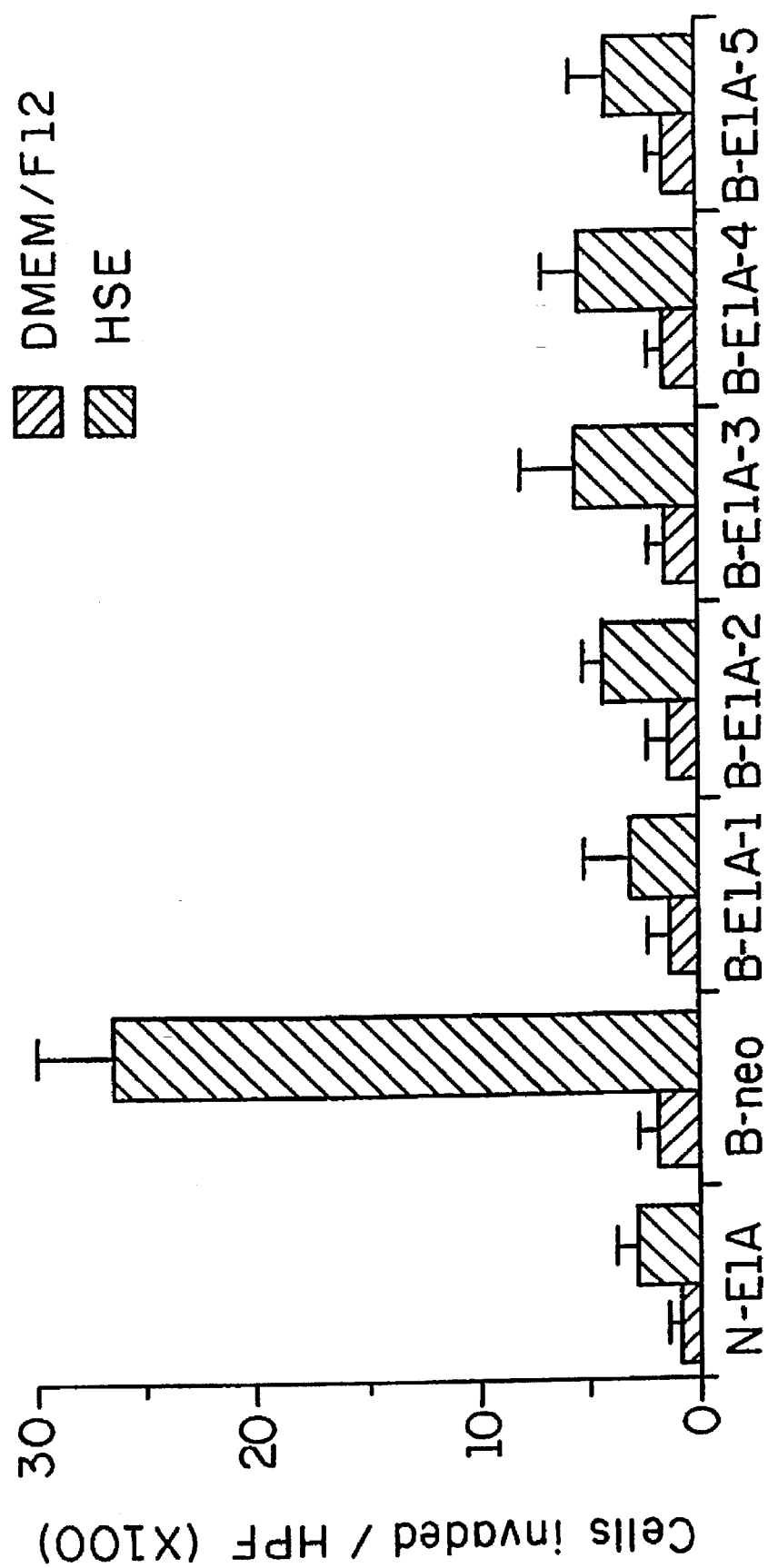
Figure 10C:
Figure 10D:
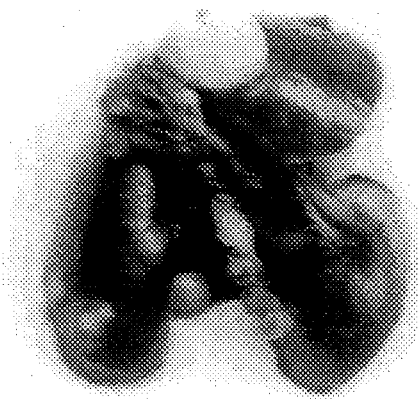
Figure 10E:
Figure 10F:

Another step in the metastatic process involves invasion of tissues and basement membranes. In vitro invasion assays also revealed significant differences between the B-neo cells and the B-E1A cell lines. B-neo cells demonstrated a high rate of invasion similar to that of B104-1-1 cells, while the B-E1A transfectants failed to invade the Matrigel. Injection of the B-neo cells and the five B-E1A cell lines into the tail vein of the nude mice showed dramatic differences in the frequencies and number of lung nodules (FIG. 10B and Table 2). Two of the five B-E1A transfectants did not give rise to any experimental metastatic tumors and the other three B-E1A lines had a very low incidence of experimental metastasis compared to that of B-neo cells (p>0.01). As expected, N-E1A cells were unable to produce any metastatic lung nodule. From these results, it is evident that E1A gene products can reduce the metastatic potential of neu-transformed 3T3 cells, possible by transcriptional repression of neu gene expression.

These results, typified by those shown in FIG. 11B, demonstrate that E1A gene products are able to suppress not only the tumorigenic and transformation events mediated by the neu gene (Example II), but are further able to suppress metastatic events that are neu mediated.

EXAMPLE IV

E1A Suppresses c-erbB-2/neu Expression Connected with Severe Malignancies in Human Ovarian Carcinoma The present example is directed to studies concerning the action of E1A in repressing c-erbB-2/neu overexpression in SKOV3.ip1 cells and the functions of E1A as a tumor suppressor gene in c-erbB-2/neu-overexpressing human cancer cells. 1. Inhibited Expression of c-erbB-2/neu-encoded p185 in E1A-expressing Ovarian Carcinoma Transfectants The E1A-expressing plasmid was cotransfected into SKOV3.ip1 cells together with the pSV2-neo plasmid carrying the neomycin-resistance marker gene, thus generating the E1A-expressing ovarian carcinoma stable transfectants. The G418-resistant clones were selected and expanded into cell lines, which were designated ip1.E1A cell lines. The same approach was used to select control cell lines, in which the pE1Ad1343 plasmids containing a 2-base pair frameshift deletion in the E1A coding sequence and producing non-functional protein products were introduced into the SKOV3.ip1 cells to generate the ip1.Efs cell line.

Figure 12A:
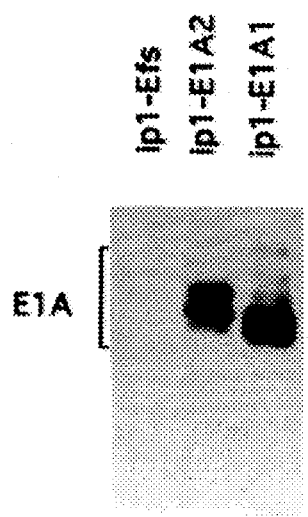
FIGS. 12A–12C show the molecular characterization of the ip1, E1A and ip1.Efs transfectants described in Example IV.

It was possible that some of the stable transfectants selected by this cotransfection strategy only harbored the neomycin resistance gene but not the E1A gene. Therefore, to identify those ip1.E1A transfectants that integrated the E1A gene and actually produced E1A proteins, immunoblot analysis with anti-E1A antibodies was performed (FIG. 12A). Two of the ip1.E1A transfectants expressed multiple species of E1A proteins as described by Harlow et al., (1985), whereas the control ip1.Efs cell line, as expected, did not express E1A proteins.

In this manner, the inventors thus established two kinds of stable transfectants: (a) ip1.E1A cells (i.e., SKOV3.ip1 E1A-expressing transfectants), which were used to test the tumor-suppressing function of E1A; and (b) ip1.Efs cells (i.e., SKOV3.ip1 transfectants containing E1A frameshift mutants), which were used as a control cell line to make sure that the changes in transformation phenotypes (if any) in ip1.E1A transfectants were not due to the selection process or to transfection of the plasmids and the pSV2-neo gene.

As shown herein, E1A proteins can repress c-erbB-2/neu-encoded p185 expression in the c-erbB-2/neu oncogene-transformed N1H3T3 cells. In addition, it is also shown herein that E1A proteins can decrease the c-erbB-2/neu mRNA level as well as c-erbB-2/neu-encoded p185 in c-erbB-2/neu-overexpressing breast cancer cell lines. To determine if the expression of E1A in ip1.E1A transfectants can inhibit p185 expression, immunoblot analysis of c-erbB-2/neu-encoded p185 protein was performed.

Figure 12B:
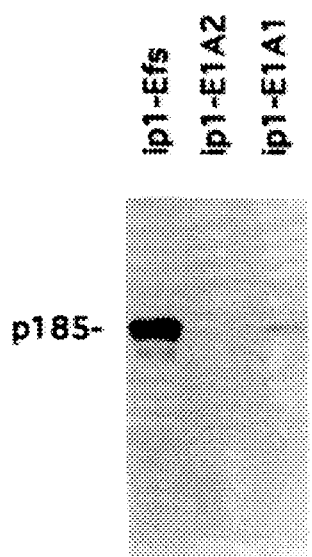
Figure 12C:
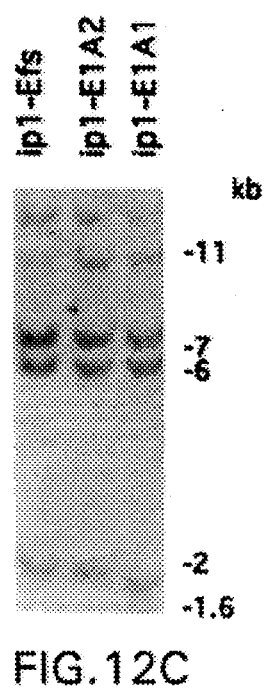

It was found that p185 protein levels were dramatically decreased in both the ip1.E1A1 and ip1.E1A2 cell lines versus the control ip1.Efs cell line (FIG. 12B), which expressed an amount of c-erbB-2/neu-encoded p185 protein comparable to that of the parental SKOV3.ip1 cell line. Since p185 proteins were dramatically reduced in ip1.E1A transfectants, DNA blot analysis of the c-erbB-2/neu gene was conducted to ensure that the reduction in c-erbB-2/neu-encoded p185 protein level was not due to loss of the c-erbB-2/neu gene. As shown in FIG. 12C, both the ip1.E1A1 and ip1.E1A2 cell lines contained copy numbers of the c-erbB-2/neu gene similar to that of ip1.Efs cell line. Therefore, the incorporation of the E1A gene into the genome of SKOV3.ip1 cells did not alter the c-erbB-2/neu gene at the DNA level. Furthermore, these results indicate that the E1A can repress the c-erbB-2/neu-encoded p185 protein expression in ip1.E1A transfectants.

2. In Vitro Suppression of SKOV3.ip1 Cell Transformation by E1A Expression

Figure 13A:
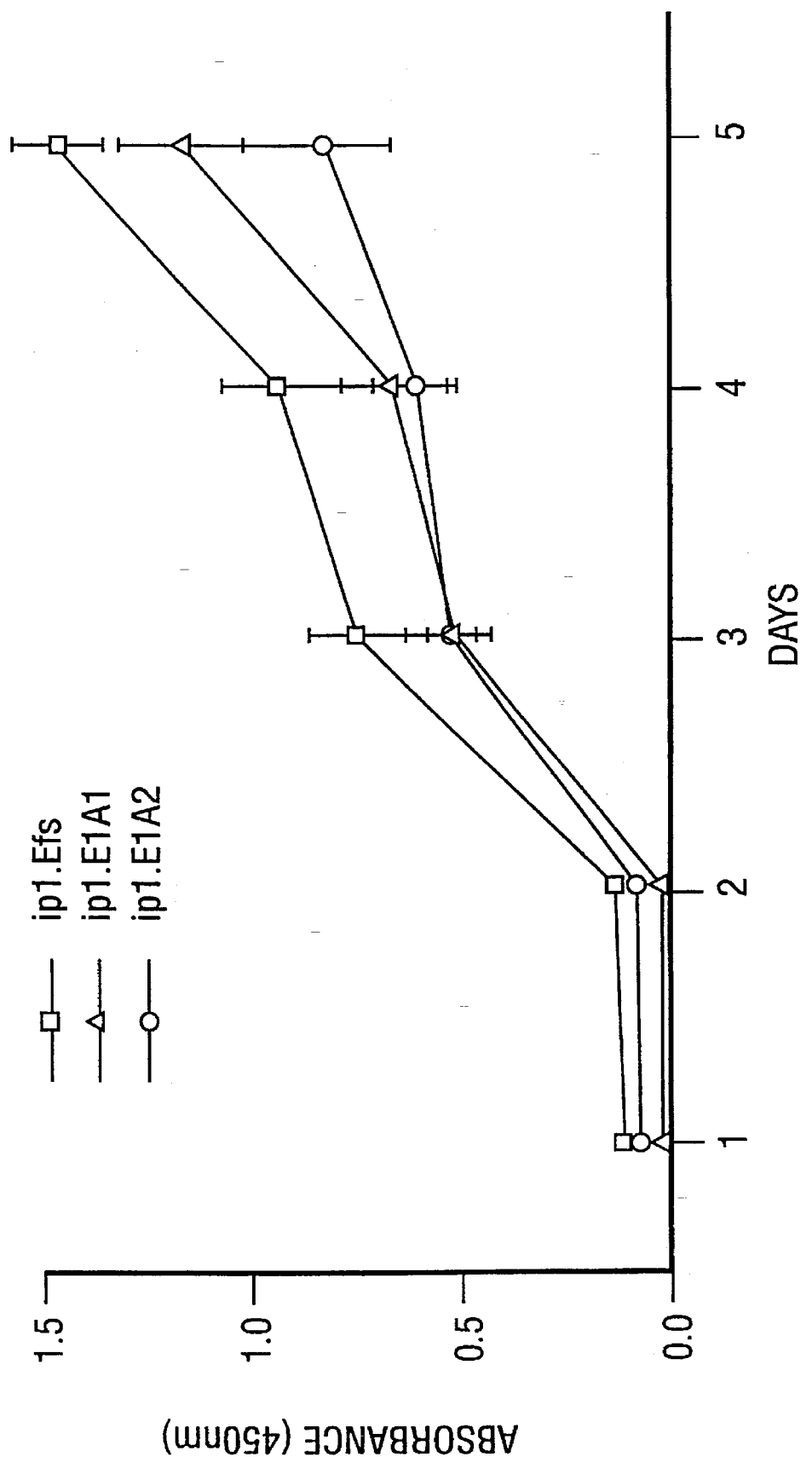
FIGS. 13A–13C show the reduced growth rate of the ip1.E1A transfectants versus control ip1.Efs cells, the decreased [$^3$H]thymidine Incorporation by the ip1.E1A transfectants versus control ip1.Efs cells, and significantly inhibited colony formation for the ip1.E1A transfectants versus control ip1.Efs cells, respectively.
Figure 13B:
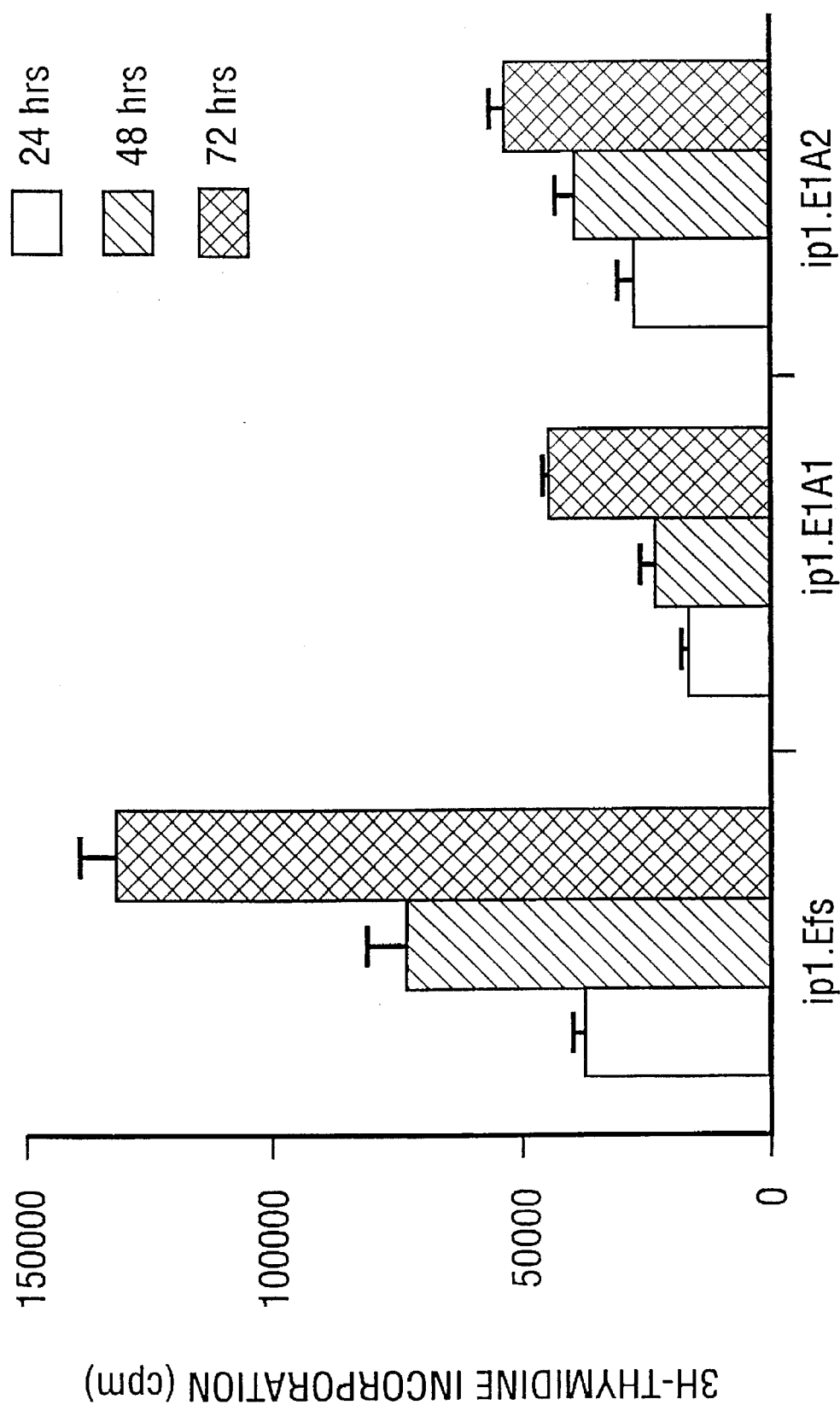

Once the E1A-expressing ip1.E1A lines were established, the inventors examined the effect of E1A expression on the c-erbB-2/neu-overexpressing ovarian cancer cells in vitro, assessing growth properties, DNA synthesis rate, and colony formation in soft agar. The growth curves of the E1A-expressing ip1.E1A1 and ip1.E1A2 cell lines and control ip1.Efs cell line indicated that E1A expression slightly reduced the growth rate of these ovarian cancer cells versus the control cells (FIG. 13A). Measurement of the DNA synthesis rate by [$^3$H]thymidine incorporation assays revealed that the control ip1.Efs cells had a high level of [$^3$H]thymidine incorporation that was similar to that of SKOV3.ip1 cells and significantly higher than the [$^3$H] thymidine incorporation in the E1A-expressing ip1.E1A1 and ip1.E1A2 cell lines (FIG. 13B).

Figure 13C:
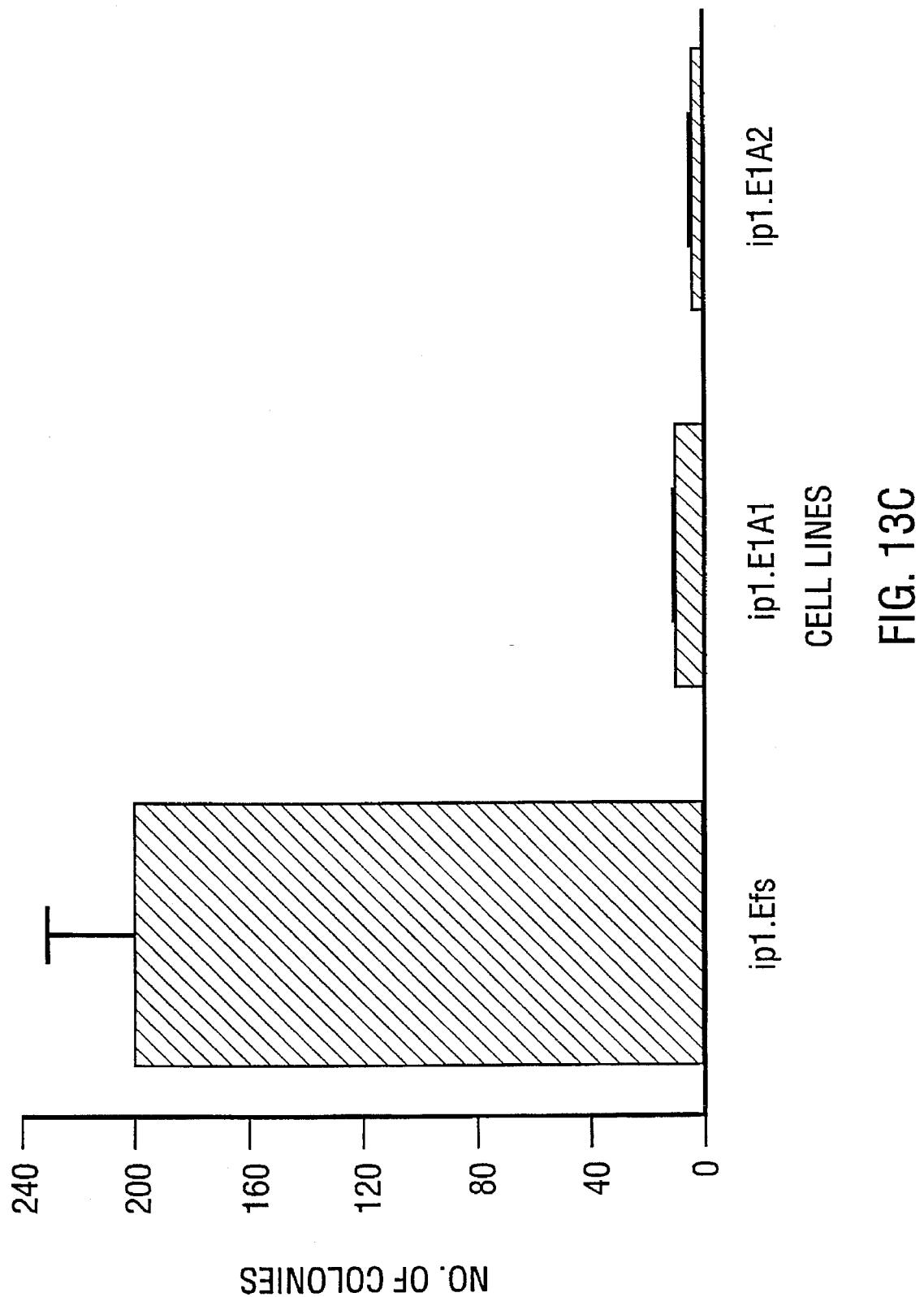

FIG. 13C shows that the c-erbB-2/neu-overexpressing ip1.Efs cells exhibited high efficiency in forming soft agar colonies, whereas the colony-forming efficiencies of the two ip1.E1A transfectants were strikingly reduced. These data suggested that E1A proteins can suppress the effect of the c-erbB-2/neu-overexpression in ovarian cancer cells and inhibit cell growth, DNA synthesis, and anchorage-independent growth.

Figure 14A:
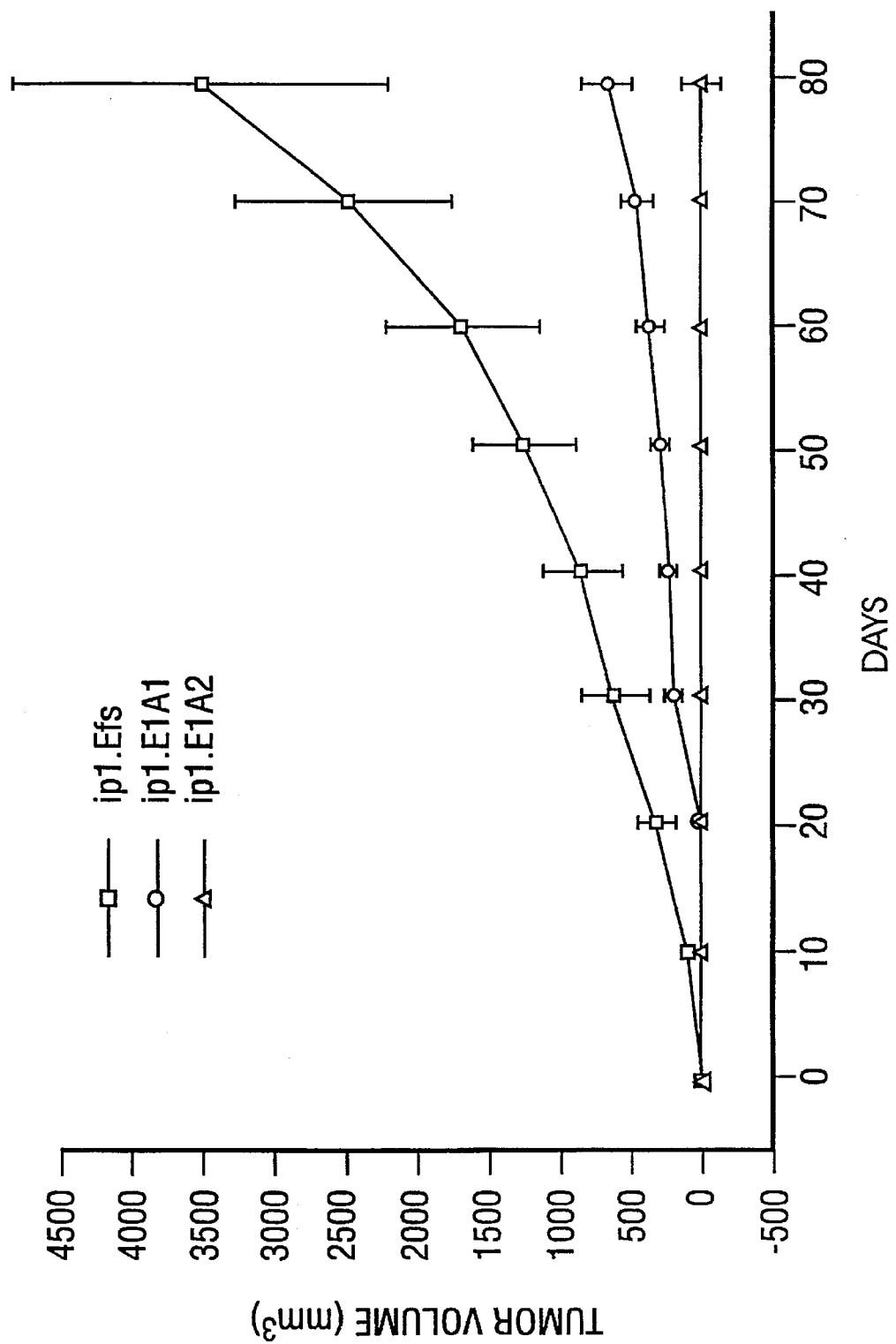
FIGS. 14A and 14B show the E1A suppressed tumor formation by c-erbB2-/neu-overexpressing ovarian cancer cells and the longer survival of mice given injections of E1A-expressing ip1.E1A cells versus mice given injections of ip1.Efs human ovarian cancer cells.

3. E1A as a Tumor Suppressor Gene for c-erbB-2/neu-Overexpressing Human Ovarian Carcinoma SKOV3 .ip1 Cells A critical test for E1A-mediated transformation suppression function in ovarian cancer cells is the ability of E1A to suppress tumor formation in vivo. Therefore, tumorigenicity assays were performed in mice that were injected s.o. with $3\times10^5$ cells from either the E1A-expressing ip1.E1A1 and ip1.E1A2 cell lines or the control ip1.Efs cell line (FIG. 14A). Like mice given injections of the parental SKOV3.ip1 cells, mice given injections of the control ip1.Efs cells formed tumors 7 days after injection and had huge tumor burdens of $3280\pm1310$ mm$^3$ by 80 days postinjection. However, nu/nu mice given injections of the same number of ip1.E1A1 transfectants did not form tumors until 21–30 days after injection, and their tumor burdens were only $460\pm170$ mm$^3$ by 80 days postinjection.

The tumor-suppressing function of E1A was more dramatic in mice given injections of the ip1.E1A2 transfectants, which did not induce tumors until 40–50 days postinjection, and 2 of 6 mice did not develop any tumor, even at 160 days postinjection. The tumor size in the four mice given injections of ip1.E1A2 were $290\pm220$ mm$^3$ at 160 days postinjection. Therefore, these results clearly demonstrated that E1A can suppress the tumorigenic potential of the ovarian carcinoma SKOV3.ip1 cells.

Figure 14B:
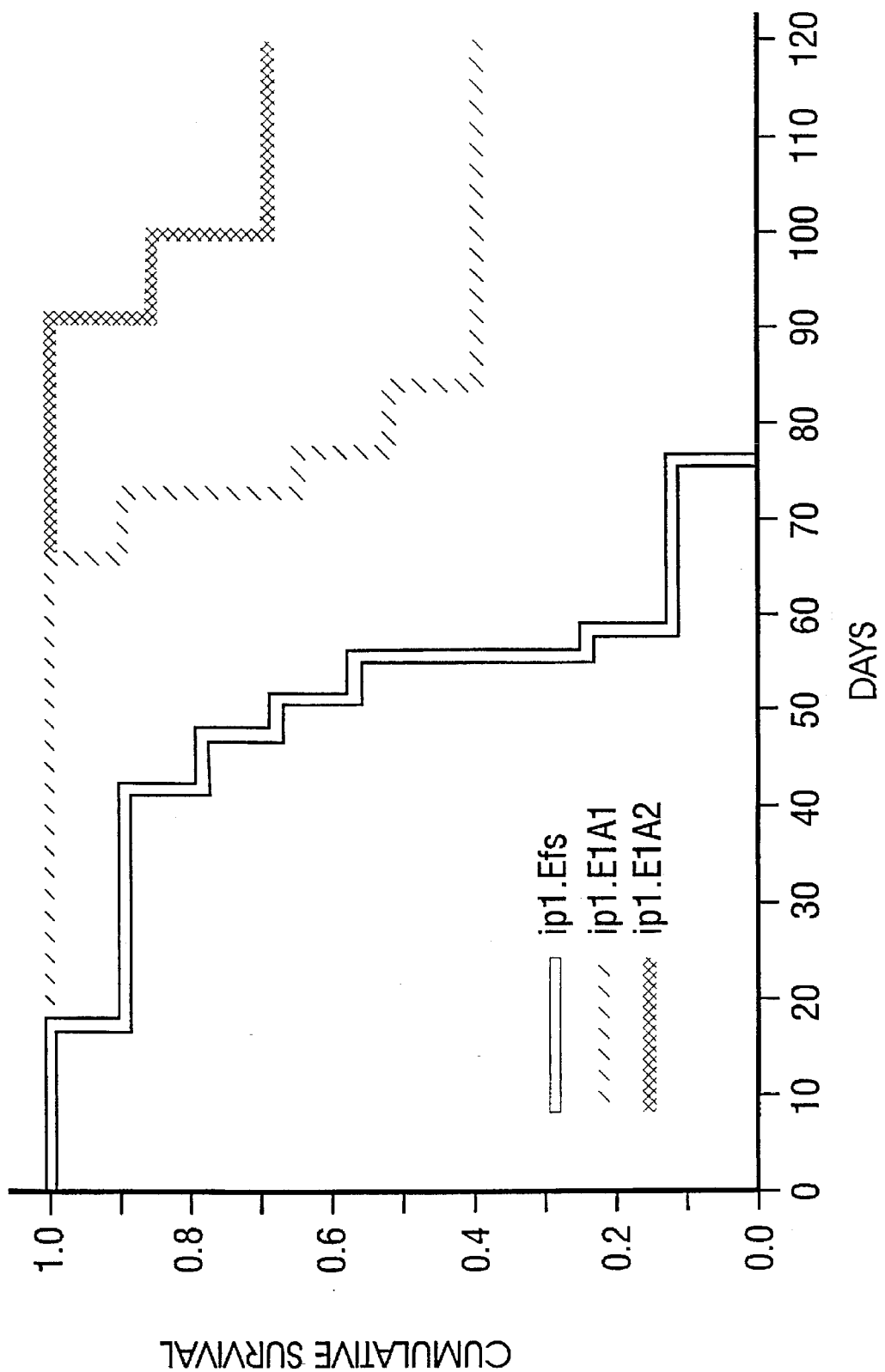

It is shown above that SKOV3.ip1 cells, when compared to SK-OV-3 cells, induced a higher mortality rate and shorter survival following i.p. injection into nu/nu mice. To determine whether E1A expression in SKOV3.ip1 cells could counteract the effect of c-erbB-2/neu overexpression and reduce the mortality rate, the inventors gave mice i.p. injections of the E1A-expressing ip1.E1A1 and ip1.E1A2 cell lines and the control ip1.Efs cell line. Mice given injections of $1\times10^4$ ip1.Efs cells developed tumor symptoms similar to those described in the previous section; one of the mice died of tumor as early as 19 days postinjection, and all of the other mice died within 75 days postinjection (FIG. 14A). However, there was a significant increase in survival for mice given injections of the E1A-transfected lines versus the parent SKOV3.ip1 and frameshift-transfectant ip1.Efs cell line (P<0.01) (FIG. 14B). The results indicated that E1A expression can reduce the mortality of mice given injections of c-erbB-2/neu-overexpressing human ovarian carcinoma cells.

4. Discussion

The inventors have isolated a derivative cell line termed SKOV3.ip1 from the ascites that developed in mice given injections of human ovarian carcinoma SK-OV-3 cells. Compared with parental SK-OV-3 cells, the SKOV3.ip1 cell line expresses higher levels of c-erbB-2/neu-encoded p185 protein and corresponding exhibits more malignant phenotypes determined by in vitro and in vivo assays. This association between enhanced c-erbB-2/neu expression and more severe malignancy is very consistent with previous studies in which c-erbB-2/neu overexpression was shown to correlate with poor prognosis in ovarian cancer patients (Slamon et al., 1989).

The inventors data provided actual evidence to support those clinical studies that c-erbB-2/neu overexpression can be used as a prognostic factor for ovarian cancer patients and that c-erbB-2/neu overexpression may play an important role in the pathogenesis of certain human malignancies such as ovarian cancer. Although not important to the utility of the claimed invention, it will be interesting to further study the molecular mechanisms and biochemical pathways involved in c-erbB-2/neu overexpression and the associated malignant phenotype. The recent identification and molecular cloning of the ligands for the c-erbB-2/neu-encoded p185, which can increase the tyrosine phosphorylation of p185, will enable future direct examination of the molecular mechanisms and the biological effects of c-erbB-2/neu overexpression in human cancer and cancer metastasis (Peles et al., 1992; Holmes et al., 1992; Lupe et al., 1990; Yarden & Peles, 1991; Huang & Huang, 1992; Dobashi et al., 1991).

The adenovirus E1A gene was originally defined as a transforming oncogene that can substitute for the myo oncogene and simian virus 40 large tumor antigen gene in the ras cotransformation assay of primary embryo fibroblasts (Land et al., 1983; Ruley, 1983; Weinberg, 1985). As detailed herein, the inventors have found that E1A products can act as transformation and metastasis suppressors in the mutation-activated rat neu-transformed mouse 3T3 cells. In this particular example, it is further demonstrated that the E1A gene products effectively repressed c-erbB-2/neu gene expression in SKOV3.ip1 ovarian carcinoma cells, suppressed transformation phenotypes in vitro, and reduced tumorigenicity and mortality rate in vivo. These results indicate that the adenovirus E1A gene can function as a tumor suppressor gene for c-erbB-2/neu-over expressing human cancer cells as well as inhibit transformation induced by mutation-activated neu oncogene in rodent cells.

Since the inventors have previously demonstrated that E1A products can dramatically inhibit the c-erbB-2/neu mRNA level and c-erbB-2/neu-encoded p185 expression in human breast cancer cell lines, and have shown that the E1A gene products can repress neu gene expression at the transcriptional level by targeting at a specific DNA element in the neu gene promotor, it is likely that the reduced p185 expression in the ip1.E1A cell lines is due to transcriptional repression of the overexpressed c-erbB-2/neu gene, which may be one of the diverse molecular mechanisms that account for the tumor suppressor function of E1A in SKOV3.ip1 ovarian cancer cells. Interestingly, it has been shown that adenovirus E1A can render hamster cell lines more susceptible to lysis by natural killer cells and macrophages (Cook & Lewis, 1984; Sawada et al., 1985) increased sensitivity to cytotoxicity by tumor necrosis factor in transfected NIH3T3 cells (Cook et al., 1989). Therefore, it is conceivable that the tumor-suppressing function of E1A may be partly due to an increased susceptibility to cytolytic lymphoid cells and molecules.

Recently, E1A protein was shown to induce a cytotoxic response that resembles programmed cell death (apoptosis) (Rao et al., 1992), which may also contribute to the tumor-suppressing function of E1A. In addition, E1A has been reported to convert three unrelated types of human cancer cells into a nontransformed state (Frisch, 1991). This suggests that E1A may also function as a tumor suppressor gene for certain human cancer cells in which c-erbB-2/neu is not overexpressed. It is not yet clear whether growth signals associated with the c-erbB-2/neu-encoded p185 protein might be activated in these human cancer cells and whether E1A might repress transforming phenotypes of these human cancer cells by blocking the signal transduction pathway associated with p185 protein via repressing c-erbB-2/neu expression; or E1A might suppress tumor formation through other mechanisms in certain human cancer cells. Despite the potential involvement of different molecular mechanisms, these results clearly establish E1A as a tumor suppressor gene for c-erbB-2/neu-overexpressing human ovarian cancer cells and indicate that E1A is a potential therapeutic reagent for the treatment of these human cancers.

It has been proposed that there are cellular "E1A-like" factors that may mimic the function of E1A in certain cell types (Nelson et al., 1990). Many common features between E1A and c-myc suggest that the c-myc gene product may be one of the cellular homologue of the E1A protein. These common features include the following: E1A and c-myc share a similar structural motif (Figge & Smith, 1988; Figge et al., 1988); both E1A and c-myc can transform primary embryo fibroblasts in cooperation the ras oncogene (Land et al., 1983; Ruley, 1983); both can bind specifically to the human Rb gene product, the RB protein (Whyte et al., 1988; Rustgi et al., 1991); both can induce apoptosis in certain cell types (Rao et al., 1992; Frisch, 1991; Nelson et al., 1990; Figge & Smith, 1988; Figge et al., 1988; Whyte et al., 1988; Rustgi et al., 1991; Evan et al., 1992); and both have been shown to block transformation of certain transformed cell lines (Frisch, 1991; Nelson et al., 1990; Figge & Smith, 1988; Figge et al., 1988; Whyte et al., 1988; Rustgi et al., 1991; Evan et al., 1992; Suen & Hung, 1991). In addition, the inventors have found that, similar to the E1A proteins, the c-myc gene product can repress c-erbB-2/neu gene expression at the transcription level, resulting in reversal of the neu-induced transformed morphology in NIH3T3 cells (Wang et al., 1991). Whether c-myc can suppress the malignancy of c-erbB-2/neu-overexpressing human cancer cells is an interesting issue that the inventors propose to examine.

E1A can inactivate the Rb tumor suppressor gene by complexing the Rb gene product, Rb protein, and by inducing RB protein phosphorylation (Whyte et al., 1988; Rustgi et al., 1991; Evan et al., 1992; Suen & Hung, 1991; Wang et al., 1991). Therefore, the inventors have recently examined whether RB might also regulate c-erbB-2/neu expression. Similar to E1A, RB can also repress c-erbB-2/neu gene expression at the transcriptional level (Yu et al., 1992). The cis-acting elements responding to E1A and RB are different but only a few base pairs away from each other. It will be interesting to study further the possibility that E1A and RB might interact with each other to regulate c-erbB-2/neu transcription.

The E1A gene of adenovirus 2, a close sera type of adenovirus 5, was shown to reduce the metastatic potential of ras-transformed rat embryo cells (Pozzatti et al., 1988). It was hypothesized that the Ad-2 E1A gene may regulate the expression of one or more cellular genes that contribute to the metastatic phenotype and expression of nm23, a gene associated with low metastatic potential in certain cell types that was subsequently shown to be elevated in E1A-expressing ras-transformed rat embryo cells (Steeg et al., 1988). Although the inventors have found that E1A can repress c-erbB-2/neu gene expression and suppress the metastatic potential of c-erbB-2/neu-transformed 3T3 cell, the c-erbB-2/neu gene expression levels in the parental ras-transformed rat embryo cells and E1A-expressing ras-transformed rat embryo cells is not known. Therefore, it is not clear at this moment whether repression of c-erbB-2/neu gene expression contributes to the metastasis suppression function of E1A in ras-transformed rat embryo cells.

One of the interesting issues on the correlation between c-erbB-2/neu overexpression and poor clinical outcome in human breast and ovarian cancers is whether c-erbB-2/neu overexpression is the result of an aggressive tumor or has a causative role for aggressive tumors. The data presented here support a direct role for c-erbB-2/neu overexpression in the pathogenesis of aggressive tumors. First, comparison of the SK-OV-3 cell line and the derivative SKOV3.ip1 cell line revealed a direct relationship between an increased c-erbB-2/neu expression level and an enhanced malignant phenotype measured by in vitro and in vivo assays. Second, c-erbB-2/neu expression in the E1A-expressing ip1.E1A cells was dramatically repressed, and, accordingly, the malignant potential of these cells was diminished. Taken together, these observations argue for a causative role of c-erbB-2/neu overexpression in the more malignant tumor pattern. Since c-erbB-2/neu-overexpressing ovarian tumors may be more malignant, more aggressive therapy might be beneficial to those ovarian cancer patients whose tumors overexpress c-erbB-2/neu-encoded p185.

EXAMPLE V

Suppression of the Neu Promoter with LT

1. Materials and Methods a. Cell Culture

NIH 3T3, B104-1-1 and Rat-1 cells were maintained in 5% CO2 in Dulbecco's modified Eagle's medium (DMEM/F-12) supplemented with 10% calf serum and 100 IU/mL penicillin and 100 mg/mL streptomycin. Cells transfected with the drug selection plasmid, pSV2neo, were grown in the above media containing 400 mg/mL G418.

b. Plasmids

The following plasmids have been described: neu deletion-CAT constructs (Suen et al., 1990), EGF receptor-CAT construct, pERCAT-9 (37), plasmid encoding activated genomic neu, cNeu-104 (Hung et al., 1986) and control filler plasmid, pSV2E (Suen et al., 1990). Two LT encoding plasmids were used, pZ189 or pVU-0, both of which showed similar results. Plasmids pVU-0 (Seidman et al., 1985) and mutant LT encoding plasmids, pK1 and pK7 (Kalderon et al., 1984), were generous gifts from Dr. Livingston.

c. Stable Transfections

The drug selection plasmid pSV2neo was cotransfected with plasmids encoding LT into B104-1-1 cells. The transfected plates were trypsinized after 48 h and split into 4 plates and subsequently maintained in media containing 400 mg/mL G418. After 3 weeks, colonies were isolated and established in media containing G418).

d. Transient Transfections and CAT assays

Cells were transfected using the modified calcium phosphate precipitation technique (Chen et al., 1987). Cells were harvested 48 h after transfection and cell extracts obtained by freeze-thawing. For transfections involving LT, the protein concentration was determined using an aliquot of the extract. Aliquots of extracts containing equal amounts of protein were used for CAT assay (Gorman et al., 1982). Transfections and CAT assays were repeated 3–4 times and representative data is shown.

e. Immunoblotting

Immunoblotting was done as described (Matin et al., 1990). Confluent cells grown in 10-cm dishes were washed and lysed with lysis buffer and 100 mg protein was loaded for electrophoresis on SDS-polyacrylamide gels followed by transfer to nitrocellulose. To detect expression of p185, blots were incubated with anti-neu antibody (c-neu, Ab-3, Oncogene Science, Manhasset, N.Y.), then reacted with secondary antibody, goat anti-mouse conjugated with horse radish peroxidase. The nitrocellulose was subsequently developed with horse radish peroxidase substrate, 4-chloro-1-napthol and hydrogen peroxide. To analyze the expression of LT antigen, blots were probed with monoclonal antibody specific for LT (SV 40 T-Ag, Ab-2, Oncogene Science). Blots were incubated with 1 mg/mL [125I]-protein A. After further washing, dried blots were exposed for autoradiography.

f. Southern blotting

Genomic DNA was harvested from cells and digested with Bam H1 for Southern blotting as described (Zhang et al., 1989). Blots were hybridized using 32P-labelled rat neu cDNA probe.

g. Focus forming assay

Focus forming assay was carried out as described (Yu et al., 1992). The cosmid clone, cNeu-104 (Hung et al., 1986), contains 30 kb of activating genomic rat neu including 2.2 kb of the neu promoter. cNeu-104 (0.5 mg) was cotransfected into normal fibroblasts (Rat-1 cells) with 0.1 mg of the drug selection plasmid, pSV2neo, and 5–10 mg plasmids encoding mutant LT (pK1) or control filler plasmid, pSV2E. Cells were trypsinized and split into 4 plates 48 h after transfection. Two plates were maintained in regular media while the other 2 plates were maintained in media supplemented with G418. For cells kept in regular media for 3 weeks, foci of transformed cells appeared on a background monolayer of nontransformed cells. G418 resistant colonies appeared for plates maintained in G418 media. Foci and G418 resistant colonies were stained with 1% crystal violet and counted. To normalize for transfection efficiency, the number of foci formed for each transfection was divided by the number of G418 colonies obtained.

2. Results a. LT Reduces Neu-Encoded p185 Levels in Cells That Overexpress p185

To test the effect of LT in cells that overexpress neu encoded p185, plasmids encoding LT, pZ189 (driven by the SV 40 promoter), together with pSV2neo (plasmids encoding the gene for neomycin resistance) were cotransfected into B104-1-1 cells. B104-1-1 cells are derived from NIH 3T3 cells transformed by the mutation-activated genomic rat neu oncogene (Shih et al., 1981; Hung et al., 1986). B104-1-1 cells express high levels of activated neu encoded p185, are phenotypically transformed (Padhy et al., 1982; Shih et al., 1981), highly tumorigenic (Yu et al., 1991; Hung et al. 1989) and have increased metastatic potential (Yu et al., 1991; Yu et al. 1992). The LT-transfected and G418 resistant B104-1-1 cells were cloned after 3 weeks and 2 cell lines expanded from the clones (named BTn14 and BTn16 cell lines) were analyzed for expression of LT and p185. Immunoblotting of cell lysates for LT using anti-LT antibody (SV 40 T-Ag, Ab-2, Oncogene Science), showed 2 bands of molecular weights less than 111 kd indicating expression of LT in BTn14 and BTn16 cell lines (FIG. 15B, lanes 1 and 2). The bands are probably different phosphorylated forms of LT, as reported previously (Livingston et al., 1987). A control cell line, BEn5, was generated by transfecting B104-1-1 cells with pSV2neo and pSV2E (control plasmid similar to pZ189, containing the SV 40 promoter but lacking the LT coding region). As expected, BEn5 and NIH 3T3 cells do not express LT (FIG. 15B, lanes 3 and 4).

The level of neu encoded p185 in these cell lines by immunoblotting whole cell lysates with monoclonal anti-p185 antibody (c-neu Ab-3, Oncogene Science), which recognizes the carboxy terminus of p185 was then analyzed. The control cell line, BEn5, expresses a high level of rat neu encoded p185 (FIG. 15A, lane 3) similar to parental B104-1-1 cells (data not shown). No p185 expression was detected in the negative control cells, NIH 3T3, using this antibody and detection system (FIG. 15A, lane 4). The two cell lines expressing LT antigen (BTn14 and BTn16 cell lines) had significantly lower levels of p185 expression (FIG. 15A, lanes 1 and 2) compared to BEn 5 cell line which does not express LT. The expression of p185 in the LT transfected cells decreased by approximately 60% to 80%. BTn16 cells (FIGS. 15A and 15B, lane 1) expressed higher levels of LT and had lower p185 expression, suggesting an inverse correlation between LT expression and p185 level.

To ensure that the decreased expression of p185 was not due to decreased copy number of rat genomic neu oncogene, the level of rat neu DNA in these cells was analyzed by Southern blot analysis. The levels of genomic rat neu oncogene in the BTn14 and BTn16 cell lines (FIG. 15C, lanes 1 and 2) were equivalent to that in BEn5 cell line (FIG. 15C, lane 3). The parental NIH 3T3 cells used as control does not have rat neu DNA. These studies show that when LT is stably expressed in cells that originally express high levels of neu-encoded p185, there is a resulting decrease in the level of p185, indicating that LT, similar to c-myc and E1A, can repress neu expression.

b. LT Specifically Inhibits the Neu Promoter

Figure 16:
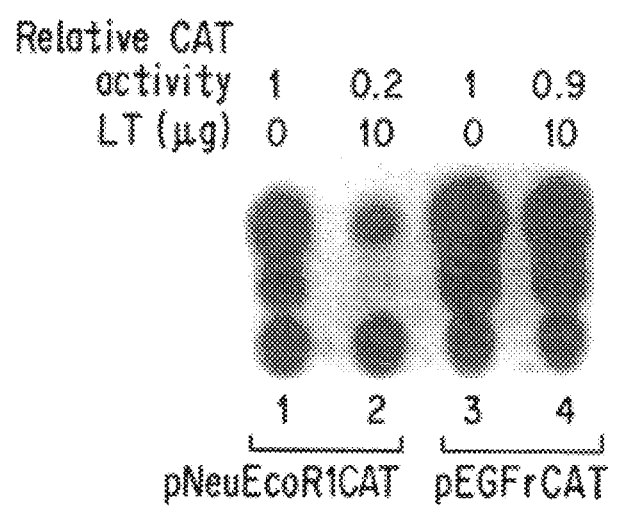
FIG. 16 shows the effect of LT on the upstream regulatory sequences of neu and epidermal growth factor receptor. One mg of pNeuEcoR1CAT (lanes 1 and 2) or pEGFrCAT (lanes 3 and 4) were cotransfected into NIH 3T3 cells with 10 mg of plasmid encoding LT, pVU-0 (lanes 2 and 4) or with control plasmid, pSV2E (lanes 1 and 3) which does not contain LT coding region. Transfections and CAT assays were carried out as described previously (Yu et al. 1992). CAT assays were standardized to equal protein concentrations of the cell extracts. The study was repeated 4 times and experimental error was within 13%. One representative set of data is shown.
Figure 17:
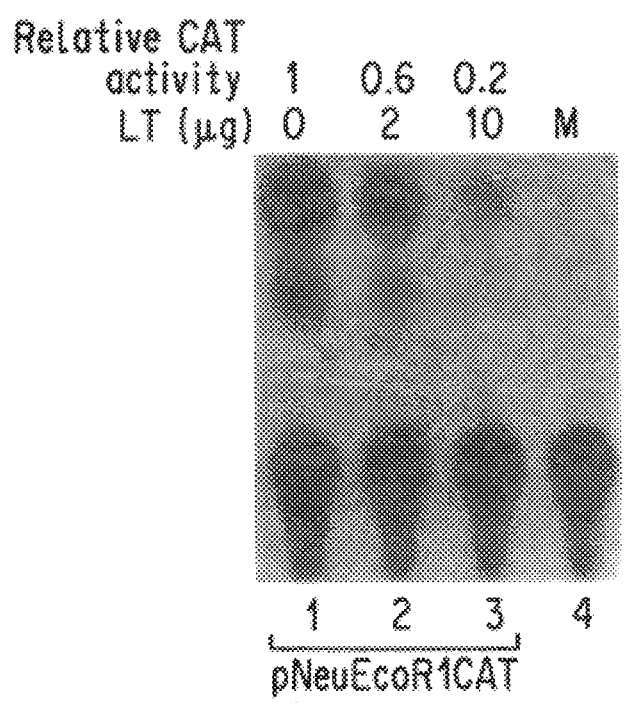
FIG. 17 shows the effect of increasing concentrations of LT on the activity of the regulatory sequences of neu. Two and 10 mg of pVU-0 were cotransfected with 1 mg of pneuEcoR1CAT into NIH 3T3 cells. The total amount of DNA transfected was equal for all reactions, with the control plasmid, pSV2E, being used to make up a final DNA concentration of 11 mg. Lane 4, M, is control CAT assay of extracts from untransfected NIH 3T3 cells. Representative data of 3 studies is shown; standard deviation was 11%.

To determine whether the LT antigen inhibited rat neu expression at the transcriptional level, the effect of LT on the upstream regulatory sequences of neu using transient transfection assays was examined. Plasmids encoding LT antigen (pVU-0 or pZ189) (Kalderon et al., 1984) were cotransfected with plasmids encoding 2.2 kb rat neu upstream regulatory sequences linked to a reporter chloramphenicol acetyl transferase (CAT) gene (pNeuEcoR1CAT) (Suen et al., 1990) into NIH 3T3 cells. The control plasmid, pSV2E, was used as a filler plasmid to adjust concentrations in cotransfections. About 80% inhibition of the 2.2 kb neu promoter activity was achieved by a 10-fold excess of LT plasmid (FIG. 16, lanes 1 & 2). The inhibitory activity of LT was specific to neu since the activity of the epidermal growth factor receptor regulatory sequence (pEGFrCAT) (Johnson et al., 1988) was unaffected by a similar amount of LT (FIG. 16, lanes 3 & 4). In addition, LT had a dose dependent effect on the activity of the regulatory sequences of neu as increasing amounts of LT led to decreased CAT activity of pneuEcoR1CAT (FIG. 17). Thus, LT specifically inhibits the activity of the rat neu promoter.

c. Repression of Neu by LT is Mediated Through the Xho1-Nar1 Region

Figure 18A:
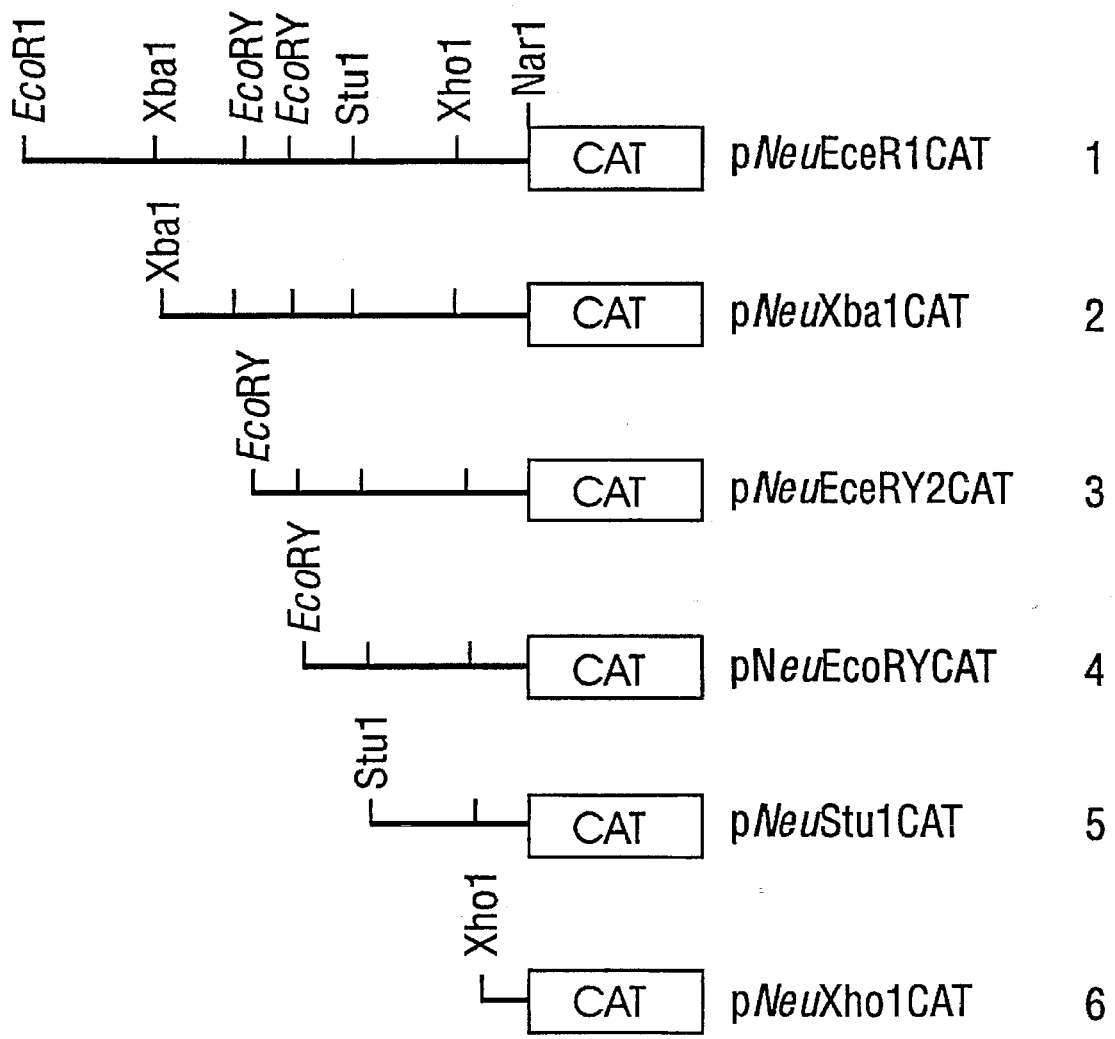
FIGS. 18A and 18B show data from serial deletions.
Figure 18B:
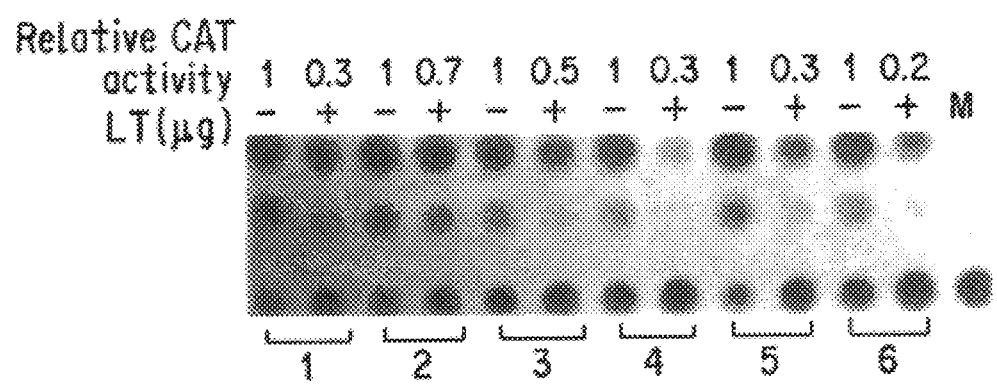

The region of the 2.2 kb neu regulatory sequence that responds to LT was mapped. To this end, series deletion constructs of the neu regulatory sequence-CAT (FIG. 18A) (Suen et al., 1990) were cotransfected with plasmid encoding LT into NIH 3T3 cells. FIG. 18B shows that the CAT activity of each of the neu-deletion constructs and the inhibition of this activity in the presence of LT (pVU-0 or pZ189). There was a 70%–80% inhibition of the CAT activity of most of the neu-deletion constructs except for pneuXba1CAT and pNeuEcoRV2CAT. In repeated studies, the inventors found less repression by LT of these two constructs. Overall, the activity of all the deletion constructs, including pneuXho1CAT, were repressed by LT. This indicates that repression of neu by LT is mediated through the 94 base pair Xho1-Nar1 region (−172 to −79, relative to first ATG) of the rat neu promoter.

S1 protection studies have identified four transcription initiation sites in the rat neu promoter. Three of them, including the two major sites (at −158 and −147) are within 30 bp downstream of the Xho1 site (Suen et al., 1990). Further deletions of nucleotides were made downstream of the Xho1 site using Bal 31 digestion (Yanisch-Perron et al., 1985). However, this led to dramatic reduction of activity of the neu promoter (data not shown). Thus the Xho1-Nar1 region of neu encompasses the minimum promoter of the rat neu gene and LT inhibits the activity of the minimum promoter of neu.

Figure 19:
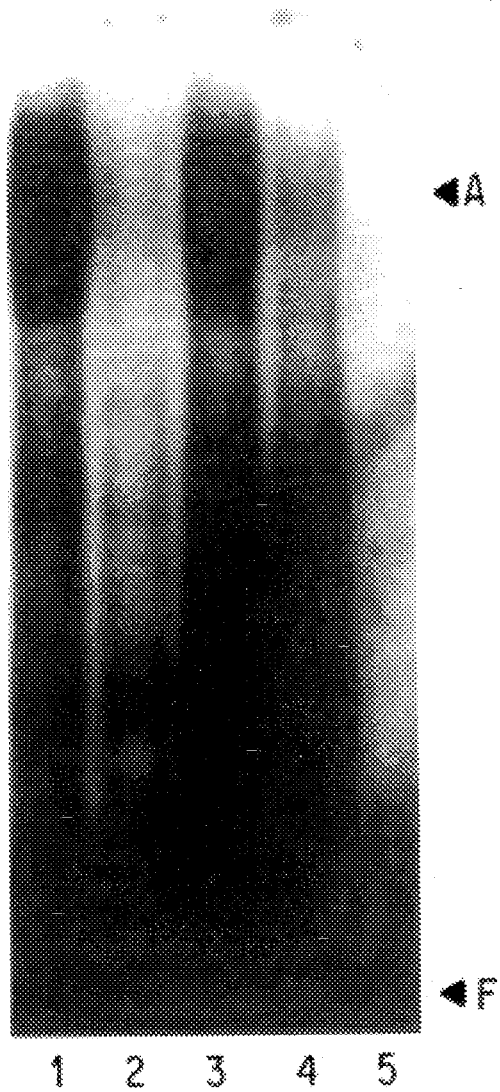
FIG. 19 shows gel shift assay demonstrating DNA-protein complex formed with the XhoI-NarI region of the neu promoter. The $^{32}$P-labelled DNA is the 94 base pair XhoI-NarI fragment. Lanes 1 and 2, nuclear extract from NIH 3T3 cells; lanes 3 and 4, nuclear extract from BTn 14 cell line. Lanes 2 and 4 contain approximately 250-fold unlabelled XhoI-NarI fragment as specific competitor. Lane 5, $^{32}$P-labelled XhoI-NarI fragment only. Incubation of probe ($10^5$ cpm) with nuclear extracts (3 µg) were carried out as described (Dynlacht et al., 1991) and samples were electrophoresed through a native 4.5% polyacrylamide gel (80:1; acrylamide:bisacrylamide) containing 0.5×TBE (45 mM boric acid, 1 mM EDTA, pH 8) for 2.5 h at 40° C. F indicates free probe.

Gel-shift assays indicated that the 94 base pair Xho1-Nar1 DNA fragment specifically complexes with proteins in the nuclear extract of NIH 3T3 cells (FIG. 19, lane 1). The complex, A, is detected using gels with large pore size (4.5% gels, acrylamide: bisacrylamide=80:1) which have been previously shown to detect large DNA-protein complex involved in transcription initiation (Dynlacht et al., 1991), but not with gels with smaller pore size (acrylamide: bisacrylamide=29:1) (data not shown). This suggests A is a large DNA-protein complex that may involve factors in the initiation or elongation complex for neu transcription. However, nuclear extracts from cells that express LT, BTn 14 cell line, also gave a similar DNA-protein complex profile in such gel-shift assays (FIG. 19, lane 3). Thus, the presence of LT in the nuclear extract did not affect the mobility of complex A. One explanation of this is that complex A is already so large that the presence of LT (in nuclear extracts from BTn 14 cells) does not create a observable difference in the shift. Indeed, complex A is found very near the top of the gel and is a broad band suggesting the present of multiple types of DNA-protein complexes. Another possibility is that LT has indirect or subtle effects on complex A at the Xho1-Nar1 fragment such as a change in phosphorylation of protein factors or a change in conformation of some factors that can not be detected by gel-shift assays.

d. A Non-transforming Mutant of LT (K1) is a Suppressor of Neu

Figure 20A:
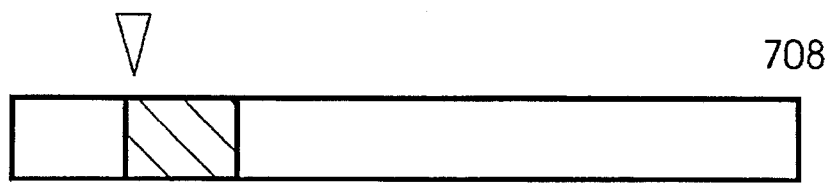
FIGS. 20A–20C show the effect of mutant LT on neu promoter activity.
Figure 20B:
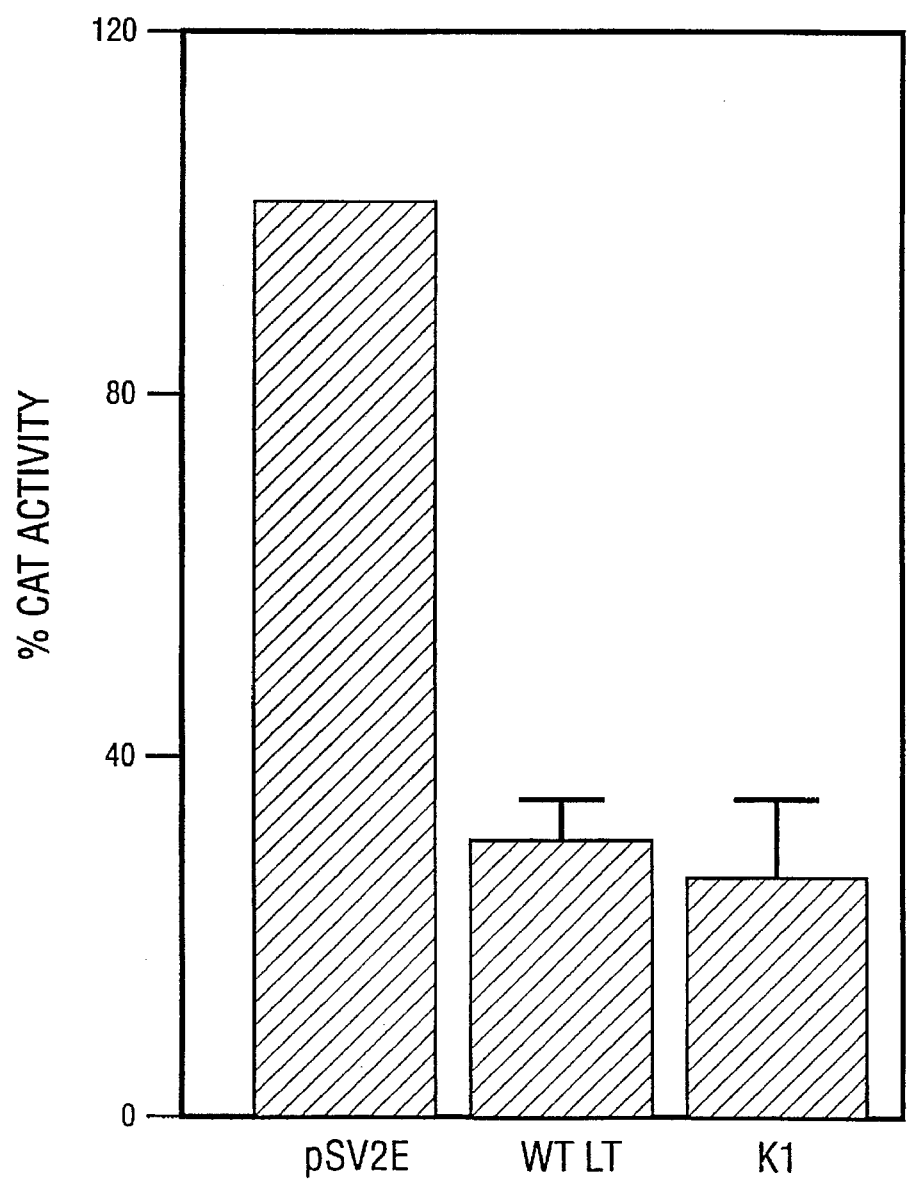

LT and Rb are known to form a protein complex (DeCaprio et al., 1988) and Rb also modulates neu expression (Yu et al., 1992), therefore, it might be expected that the LT-Rb complex is involved in repression of neu. To examine this, an available mutant of LT (K1) was utilized. K1 has a single amino acid change within the region required for Rb binding (amino acids 105–114 of LT) (FIG. 20A) (Kalderon et al., 1984). K1 expresses mutant LT protein which is unable to complex Rb (DeCaprio et al., 1988) and K1 is defective for transformation as assayed by focus forming assay in Rat-1 cells (Kalderon et al., 1984; Cherington et al., 1988). pneuXho1CAT together with plasmids encoding wild type (pVU-0) or mutant LT (K1) were cotransfected into NIH 3T3 cells. Surprisingly, K1 represses neu as effectively as wild type LT (FIG. 20B). Therefore, complex formation between LT and Rb is not required for LT-mediated neu repression.

Figure 20C:
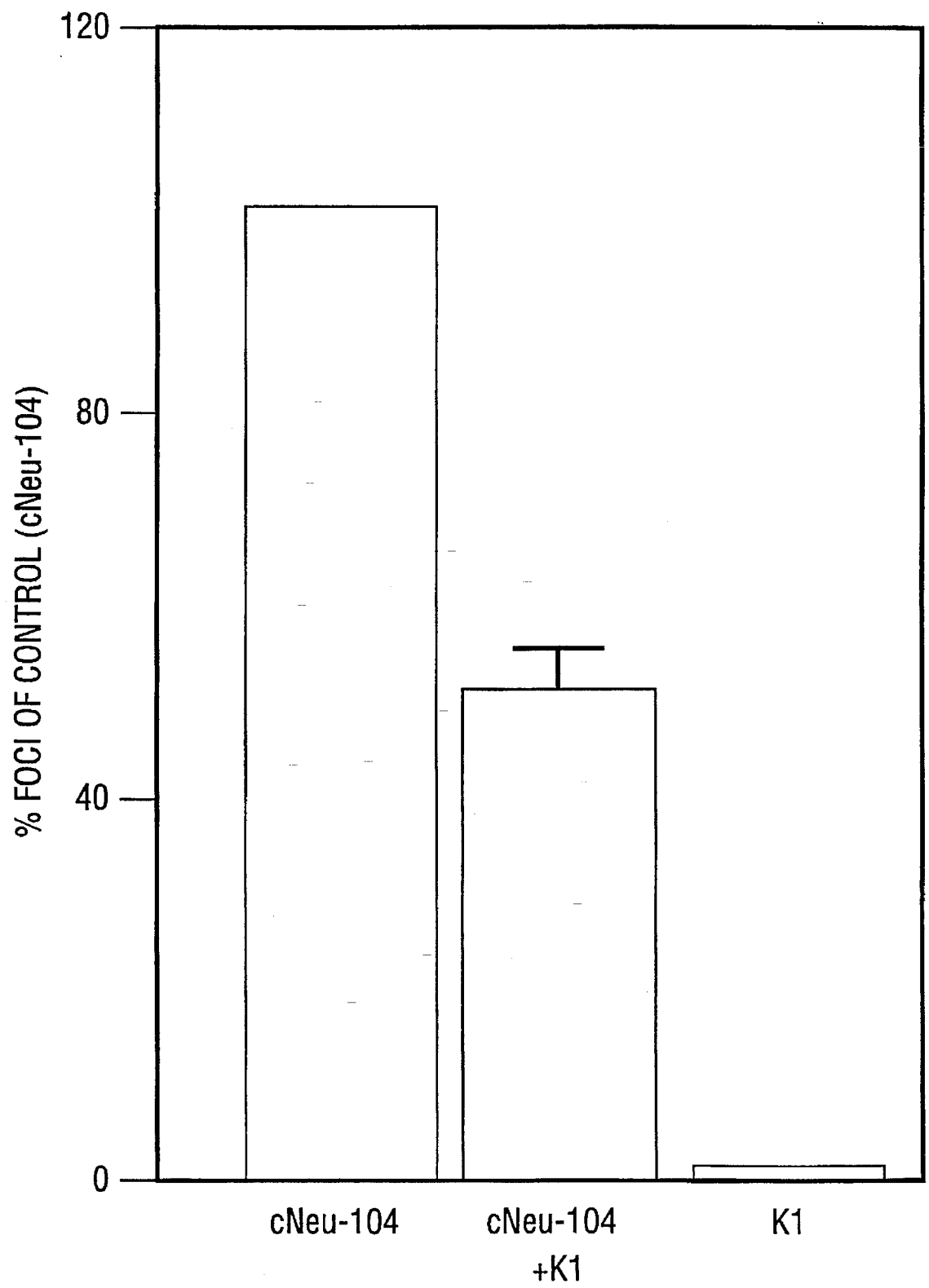

K1, unlike wild type LT, is unable to transform Rat-1 cells in focus forming assays (Kalderon et al., 1984). Therefore, the above results raises an interesting question whether K1 may function as a transformation suppressor of activated neu in Rat-1 cells. To test this possibility, focus forming assays were carried out to determine the effect of stably transfecting K1 with activated genomic neu. The plasmid cNeu-104 encodes the activated genomic neu which has a single point mutation in the transmembrane domain and is driven by 2.2 kb of neu upstream regulatory sequences (Hung et al., 1986). Upon introduction of cNeu-104 into normal Rat-1 fibroblasts, those cells that stably express activated neu are transformed and 3–4 weeks later form visible foci on a background of normal monolayer cells. When K1 was cotransfected with cNeu-104 into Rat-1 cells, it led to 50% reduction in the number of foci formed by cNeu-104 (FIG. 20C). Transfection of K1 only does not induce any foci. Suppression of neu-transforming activity with wild type LT (pVU-0) is complicated by the fact that wild type LT itself forms transformed foci in Rat-1 cells (data not shown) which makes it impossible to analyze the data. Therefore, mutant LTs unable to complex with Rb that act as transformation suppressors of activated neu may be the most clinically useful of the LT gene products.

3. Discussion

The results of these studies show that the function of the rat neu promoter is suppressed by the transforming viral oncoprotein, SV 40 LT antigen. This activity of LT is similar to that observed for the adenovirus 5 E1A and the c-myc oncoproteins, with whom LT shares a few structural and functional similarities but striking differences. The inhibitory activity of LT is apparent in the LT-transfected stable cell lines which showed an inverse correlation of neu p185 to LT protein expression. Thus, expression of LT in cells leads to reduced expression of neu encoded p185 in cells.

LT inhibits neu by repressing the activity of the minimum neu promoter. Series deletion analysis of the upstream regulatory sequences of neu showed that repression by LT is mediated through the 94 bp Xho1-Nar1 region of the neu gene, which contains the minimum promoter 30 bp downstream of the Xho1 site. This result is unlike that of c-myc and E1A, since these repress neu through an upstream region of the regulatory sequences of neu. Thus LT mediates repression of neu through a different pathway compared to c-myc and E1A. Therefore, these structurally related oncogenes repress the activity of the neu promoter by acting through different regions of the regulatory sequences of neu. Although the promoter of the epidermal growth factor receptor and the promoter of neu share some common features (Suen et al.,1990; Johnson et al., 1988), LT did not inhibit the activity of the promoter of epidermal growth factor receptor. Thus, LT specifically affects the promoters of certain growth factor receptors.

Since LT mediates repression of neu through the Xho1-Nar1 region which contains only minimum sequence upstream of the two major transcription initiation sites, it is possible that LT may modulate transcription initiation or elongation from the neu promoter. LT is known to interact with cellular transcription factors such as AP-2 and abrogate its function (Mitchell et al., 1987). However, examination of the 94 bp sequences within Xho1-Nar1 revealed no motif with significant homology to the AP-2 (Suen et al., 1990).

EXAMPLE VI

Suppression of Neu-Mediated Cancer with LT

1. Suppression of Neu-Mediated Cancer by LT in Mice

The inventors are conducting ongoing studies of the abilities of pK1 to suppress the growth and metastasis of neu-overexpressing human ovarian cancer cells (SK-OV-3 cells) in female homozygous nu/nu (nude) mice. SK-OV-3 cells express high levels of neu and are highly metastatic in nude mice (Yu et al. 1993). These studies involve treatment of these mice with a liposomal complex liposomes comprising lipids and pK1. pK1 comprises DNA encoding a non-transforming mutant of LT (Kalderon et al. 1984). Details of this study are given in Example VII, 2.

2. LT Suppression of Neu-Mediated Cancer in Humans

The results obtained using the cell lines and animal models described in this application are of the type widely accepted by those of skill in the art as being predictive of success in human treatment regimens. Indeed, clinical trials concerning the use of LT to suppress the expression of neu in humans are contemplated. However, due to precautions which are necessarily attendant to every new pharmaceutical, the compositions and methods of the present invention have not yet been tested in such a clinical setting. Nevertheless, the results presented herein reasonably demonstrate that LT will be useful in combating cancers which exhibit neu-overexpression, such as breast cancers, ovarian cancers, lung cancer, gastric cancer, oral cancers and prostate cancer.

One of the initial clinical trials to be performed involves non-transforming mutants of LT, for example K1. These non-transforming mutants have demonstrated the ability to suppress neu-mediated cancers in both cell cultures studies and in vivo animal model studies. The use of such mutants avoids potential problems with transformation. In these clinical studies, K1 will be introduced into the human cancer cells to suppress the production of neu.

Among those patients who will benefit from this therapy are those whose cancer cells express high levels of neu. The level of neu expression in a given patient can be determined by analysis of biopsy samples of cancer tissue using routine techniques such as immunohistochemistry or western blotting. These diagnostic techniques are routinely practiced and well known to those of skill in the art.

Targeting of cancerous tissues overexpressing neu may be accomplished in any one of a variety of ways. Plasmid vectors and retroviral vectors, adenovirus vectors, and other viral vectors all present means by which to target human cancers. The inventors anticipate particular success for the use of liposomes to target LT genes to cancer cells. In one of the first series of clinical phase to be performed, DNA encoding nontransforming mutants of LT such as K1 will be complexed with liposomes in the manner described in Example VII, and this DNA/liposome complex will be injected into patients with certain forms of cancer, such as breast cancer, intravenous injection can be used to direct the K1 gene to all cells, including those which overexpress neu. Directly injecting the liposome complex into the proximity of a cancer can also provide for targeting of the complex with some forms of cancer. For example, cancers of the ovary can be targeted by injecting the liposome mixture directly into the parataenial cavity of patients with ovarian cancer. Of course, the potential for liposomes that are selectively taken up by a population of cancerous cells exists, and such liposomes will also be useful for targeting the LT gene.

Those of skill in the art will recognize that the best treatment regimens for using LT to suppress neu-mediated cancers can be straightforwardly determined. This is not a question of experimentation, but rather one of optimization, which is routinely conducted in the medical arts. The in vivo studies in nude mice provide a starting point from which to begin to optimize the dosage and delivery regimes. The frequency of injection will initially be once a week, as was done in the mice studies. However, this frequency might be optimally adjusted from one day to every two weeks to monthly, depending upon the results obtained from the initial clinical trials and the needs of a particular patient. Human dosage amounts can initially be determined by extrapolating from the amount of LT used in mice, approximately 15 µg of plasmid DNA per 50 g body weight. Based on this, a 50 kg woman would require treatment with 15 mg of DNA per dose. Of course, this dosage amount may be adjusted upward or downward, as is routinely done in such treatment protocols, depending on the results of the initial clinical trials and the needs of a particular patient.

3. Liposomal Transfection with E1A and/or LT to Suppress neu-Mediated Cancers

One particularly useful way to use E1A and/or LT to repress neu-mediated phenotypes is via the use of liposomes for carrying the suppressor's DNA into the oncogenic cells.

EXAMPLE VII

Preparation of Liposome/DNA Complexes and Prevention of Neu-Mediated Tumors with the Complexes 1. Preparation of Liposomes Catatonic liposomes which are efficient transfection reagents for both the E1A and LT genes for animal cells can be prepared using the method of Gao et al. (1991). Gao et al. describes a novel catatonic cholesterol derivative that can be synthesized in a single step. Liposomes made of this lipid are reportedly more efficient in transfection and less toxic to treated cells than those made with the reagent Lipofectin. These lipids are a mixture of DC-Chol ("3β(N-(N'N'-dimethylaminoethane)-carbamoyl cholesterol") and DOPE ("dioleoylphosphatidylethanolamine"). The steps in producing these liposomes are as follows.

DC-Chol is synthesized by a simple reaction from cholesteryl chloroformate and N,N-Dimethylethylenediamine. A solution of cholesteryl chloroformate (2.25 g, 5 mmol in 5 ml dry chloroform) is added dropwise to a solution of excess N,N-Dimethylethylenediamine (2 ml, 18.2 mmol in 3 ml dry chloroform) at 0° C. Following removal of the solvent by evaporation, the residue is purified by recrystallization in absolute ethanol at 4° C. and dried in vacuo. The yield is a white powder of DC-Chol.

Cationic liposomes are prepared by mixing 1.2 μmol of DC-Chol and 8.0 μmol of DOPE in chloroform. This mixture is then dried, vacuum desiccated, and resuspended in 1 ml sterol 20 mM Hepes buffer (pH 7.8) in a tube. After 24 hours of hydration at 4° C., the dispersion is sonicated for 5–10 minutes in a sonicator form liposomes with an average diameter of 150–200 nm.

To prepare a liposome/DNA complex, the inventors use the following steps. The DNA to be transfected is placed in DMEM/F12 medium in a ratio of 15 μg DNA to 50 μl DMEM/F12. DMEM/F12 is then used to dilute the DC-Chol/DOPE liposome mixture to a ratio of 50 μl DMEZM/F12 to 100 μl liposome. The DNA dilution and the liposome dilution are then gently mixed, and incubated at 37° C. for 10 minutes. Following incubation, the DNA/liposome complex is ready for injection.

2. In Vivo Treatment of Neu-Mediated Cancer Via Liposomes

The inventors have shown that liposome-mediated direct gene transfer techniques can be employed to obtain E1A suppression of neu-overexpressing human cancer cells in living host. The protocol for this study was as follows.

Female nude mice (5–6 weeks old) were given intraperitoneal injections of SK-OV-3 cells (2×10⁶/100 μl). SK-OV-3 cells are human ovarian cancer cells that have been shown to grow within the peritoneal cavity of nude mice. After five days, the mice were given intraperitoneal injections of various compounds. Some mice were injected with E1A DNA alone, some were injected with liposome/E1A DNA complex prepared in the manner described above, and some were injected with liposome/Efs (an E1A frameshift mutant) DNA complex. 200 μl of a given compound was injected into a given mouse. After the initial injections, injections were repeated every seven days throughout the life of the mouse.

Figure 21:
FIG. 21 shows liposome-deviated direct gene transfer techniques allow the delivery of the E1A gene to neu-overexpressing SK-OV-3 human ovarian cancer cell. The three mice were each injected with SK-OV-3 cells. Five days later, the mice were injected with (1) E1A DNA only, (2) complex of liposome and Efs DNA (an E1A frame shift mutant that does not cause active E1A to be produced), and (3) complex of liposome and E1A DNA. Booster injections of the same compositions were given each respective mouse on a weekly basis for the remainder of the mouse's life. Mouse 1 developed extensive bloody ascites and died 65 days after SK-OV-3 injection. Mouse 2 developed extensive blood ascites and a large tumor and died 76 days after the injection of SK-OV-3 cells. Mouse 3 appeared healthy and was alive 160 days after SK-OV-3 injection.

FIG. 21 shows the results of this study. Mouse 1, was injected with E1A DNA alone and developed extensive bloody ascites. Mouse 1 died 65 days after the injection of the SK-OV-3 cells. Mouse 2 was injected with liposome/Efs DNA complex. Mouse 2 developed extensive bloody ascites and a large tumor and died 76 days after injection of the SK-OV-3 cells. Mouse 3 was injected with the liposome/E1A DNA complex. This mouse looked healthy and normal and was still alive 160 days after the injection of the SK-OV-3 cells.

These results indicate that liposome-mediated E1A gene transfer can inhibit neu-overexpressing human ovarian cancer cell growth. Therefore, it is predictable that liposome-mediated E1A or LT gene therapy may serve as a powerful therapeutic agent for HER-2 neu-overexpressing human ovarian cancers by direct targeting of E1A or LT at the HER-2 neu-oncogene.

The inventors are presently testing the effects of the LT mutant pK1 on the growth and metastasis of the human ovarian cancer cells SK-OV-3 in essentially the same manner as used to test the effects of E1A on these cells. In these experiments, nude mice were intraperitoneally injected with 1.8×10⁶ SK-OV-3 cells per ml of phosphate buffered saline. The following week, and every week thereafter, the mice were injected with 15 μg pK1 in suspension with 1 μmol liposome (DC-Chol-containing liposomes prepared as previously described). As controls, 5 mice were injected with SK-OV-3 cells and then injected with the control plasmid pGEM liposomes every week. Based on the fact that previous data has shown that pK1 can suppress neu-induced foci and transcription from the neu gene promoter, it is expected that the injected pK1 will reduce tumor growth of the SK-OV-3 cells in the mice.

3. Liposomal Transfection With E1A and/or LT to Treat Humans

Based on the results of the in vivo animal studies described above, those of skill in the art will understand and predict the enormous potential for human treatment of neu-mediated cancers with E1A and/or LT DNA complexed to liposomes. Clinical studies to demonstrate these affects are contemplated. One set of such studies is described in Example VI, 2. where clinical trials involving the use of LT complexed to liposomes are described. E1A or any other neu-suppressing gene product may be complexed with liposomes and employed in human studies in a manner similar to that described for LT. These clinical trials are anticipated to show utility of LT, E1A, and other neu-suppressing gene products for the treatment of neu-overexpressing cancers in humans. Dosage and frequency regimes will initially be based on the data obtained from in vivo animal studies, as was described in Example VI, 2.

EXAMPLE VIII

Adenoviral E1A Gene Therapy of Human Cancers Expressing High Levels of P185

The present example provides for the introduction of the E1A or LT gene for treatment of human cancers expressing high levels of P185. This may be achieved most preferably by introduction of the desired gene through the use of a viral vector to carry either the E1A or LT sequences to efficiently infect the tumor, or pretumorous tissue. These vectors will preferably be an adenoviral, a retroviral, a vaccinia viral vector or adeno-associated virus (Muro-cacho et al., 1992). These vectors are preferred because they have been successfully used to deliver desired sequences to cells and tend to have a high infection efficiency. The inventors have conducted studies showing that native adenovirus can be employed to transfer the E1A gene in accordance with the invention. However, a particularly preferred type of adenovirus is the group of replication-deficient adenoviruses.

The HER-2/neu oncogene encodes a MW 185,000 epidermal growth factor receptor-related transmembrane protein (p185) with intrinsic tyrosine kinase activity. Overexpression of the normal human HER-2/neu protooncogene, which can also lead to higher overall tyrosine kinase activity, is a frequent event in many types of human cancers, including cancers of the breast, ovarian, lung, uterine cervix, stomach and colon cancer, for example. Correlation between the overexpression of HER-2/neu and the number of lymph node metastases in breast cancer patients and decreased survival in both breast and ovarian cancer patients has been reported. The present inventors have shown in the previous examples that adenovirus 5 E1A gene product can repress HER-2/neu oncogene expression and suppress the tumorigenic and metastatic potential of activated rat neu oncogene-transformed mouse 3T3 cells. Introduction of the E1A gene into the human ovarian cancer cell line SK-OV-3(i.p.), which has enhanced expression of HER-2/neu, resulted in reduced malignant phenotypes in vitro and in vivo. Those data indicated that the E1A gene can be considered as a tumor suppressor gene for HER-2/neu overexpressing human cancer cells.

Replication-deficient adenovirus represents a gene delivery system that should be able to efficiently transfer an exogenous gene directly to tumor cells in vivo. Unlike vectors that require target cell replication for gene transfer, such as retrovirus which can aonly infect proliferating cells, adenovirus can transfer genes into both proliferating and non-proliferating cells. The extrachromosomal location of adenovirus in the cells (non-integration) decreases the chance of activating cellular oncogenes. A high titer of adenovirus is easily produced and purified. Replication-deficient adenovirus containing E1A was constructed by E3 and E1B deletion matant (E1B and E3 is required for adenovirus replication), control virus was constructed by additional E1A deletion mutant.

Figure 22:
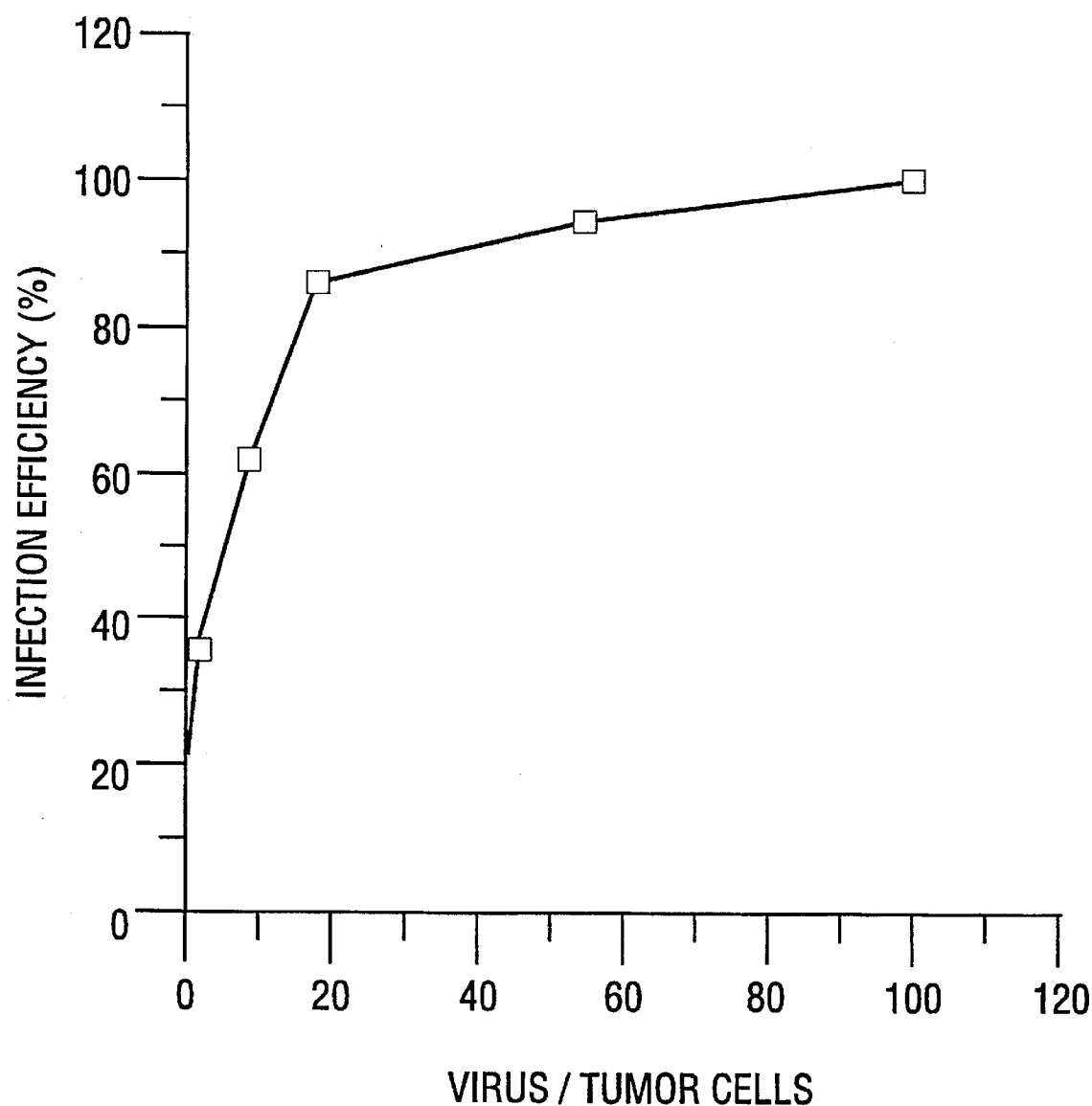
FIG. 22 shows the infection efficiency of adenovirus in ovarian cancer SK-OV-3(i.p.). SK-OV-3(i.p.) in 6 well plates (2.5×$10^5$/well) were infected once by Ad. RSVβgal at different virus/tumor cell ratios. Two days later, cells were fixed and stained with X-gal. Infection efficiency=No. of positive cells/No. of total cells×100%.
Figure 23:
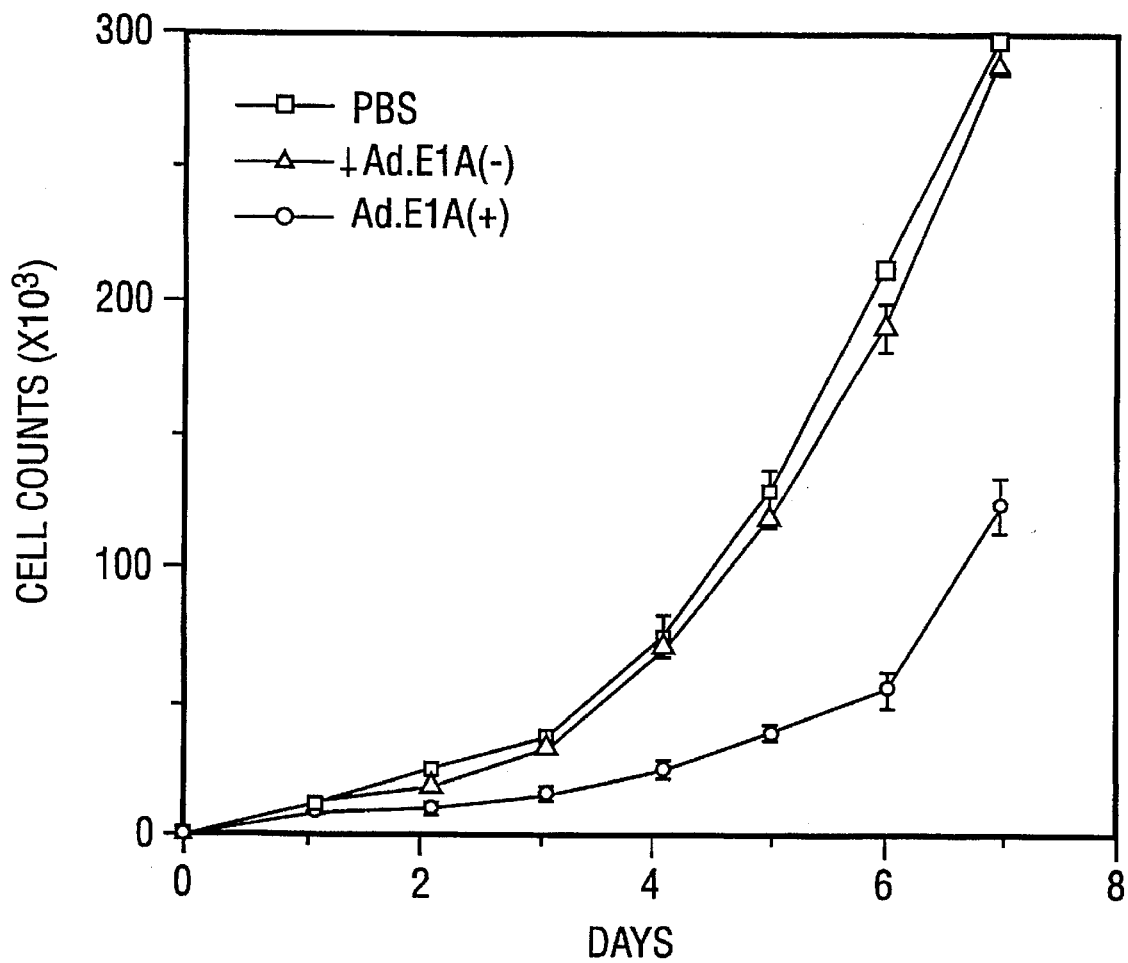
FIG. 23 shows a growth curve of SK-OV-3(i.p.) after treatment by Ad. E1A in vitro. SK-OV-3(i.p.) in 12 well plates ($10^4$/well) were infected once by 2×$10^5$ adenovirus and cell growth was followed for 7 days.
Figure 24:
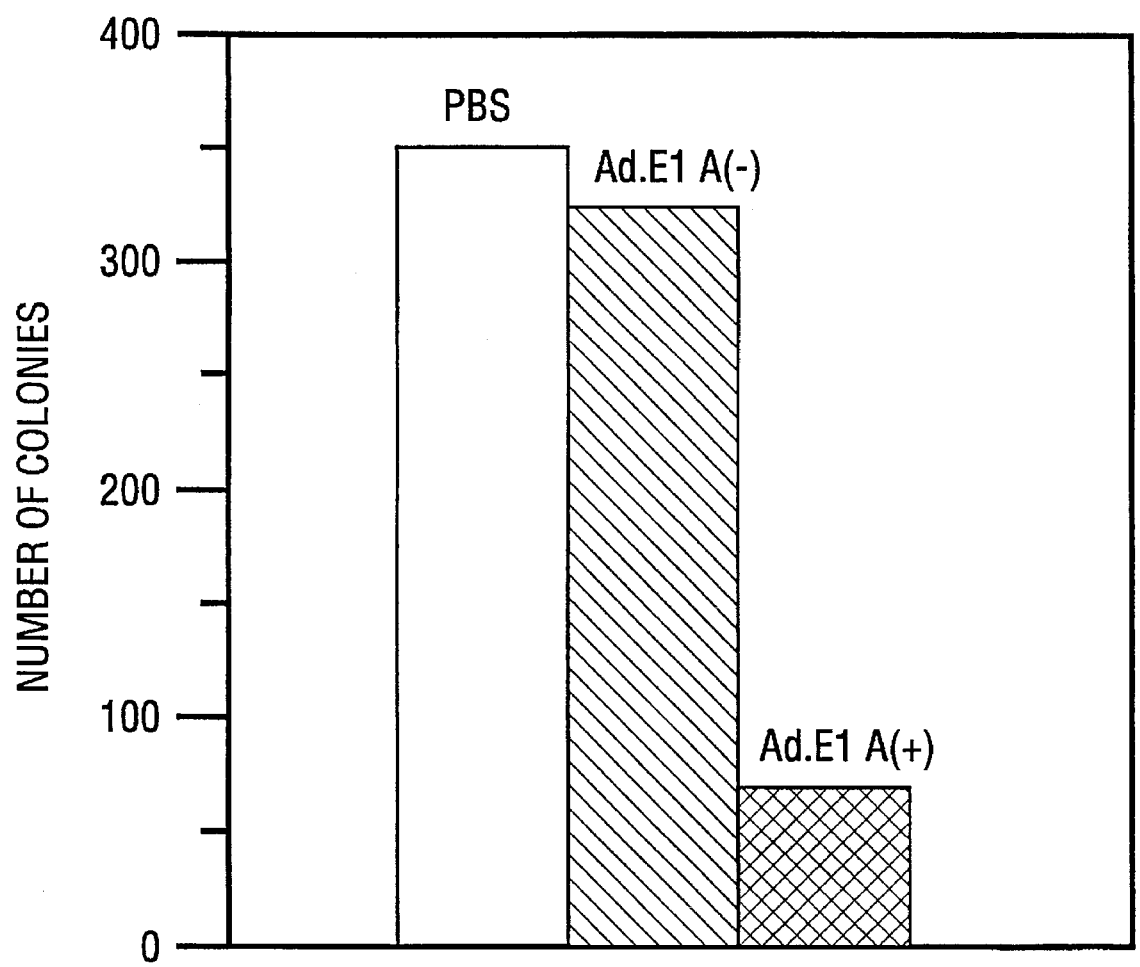
FIG. 24 shows colony formation in soft agarose. SK-OV-3(i.p.) cells were infected once with adenovirus at a virus/tumor ratio of 20/1. Aliquots of 5×$10^4$ cells were mixed with 0.35% agarose in DMEM medium and plated over a base layer of 0.7% agarose. Culture medium was allowed to harden in 6 well plates (n=3). Colonies were stained and counted about 6 weeks later.
Figure 25:
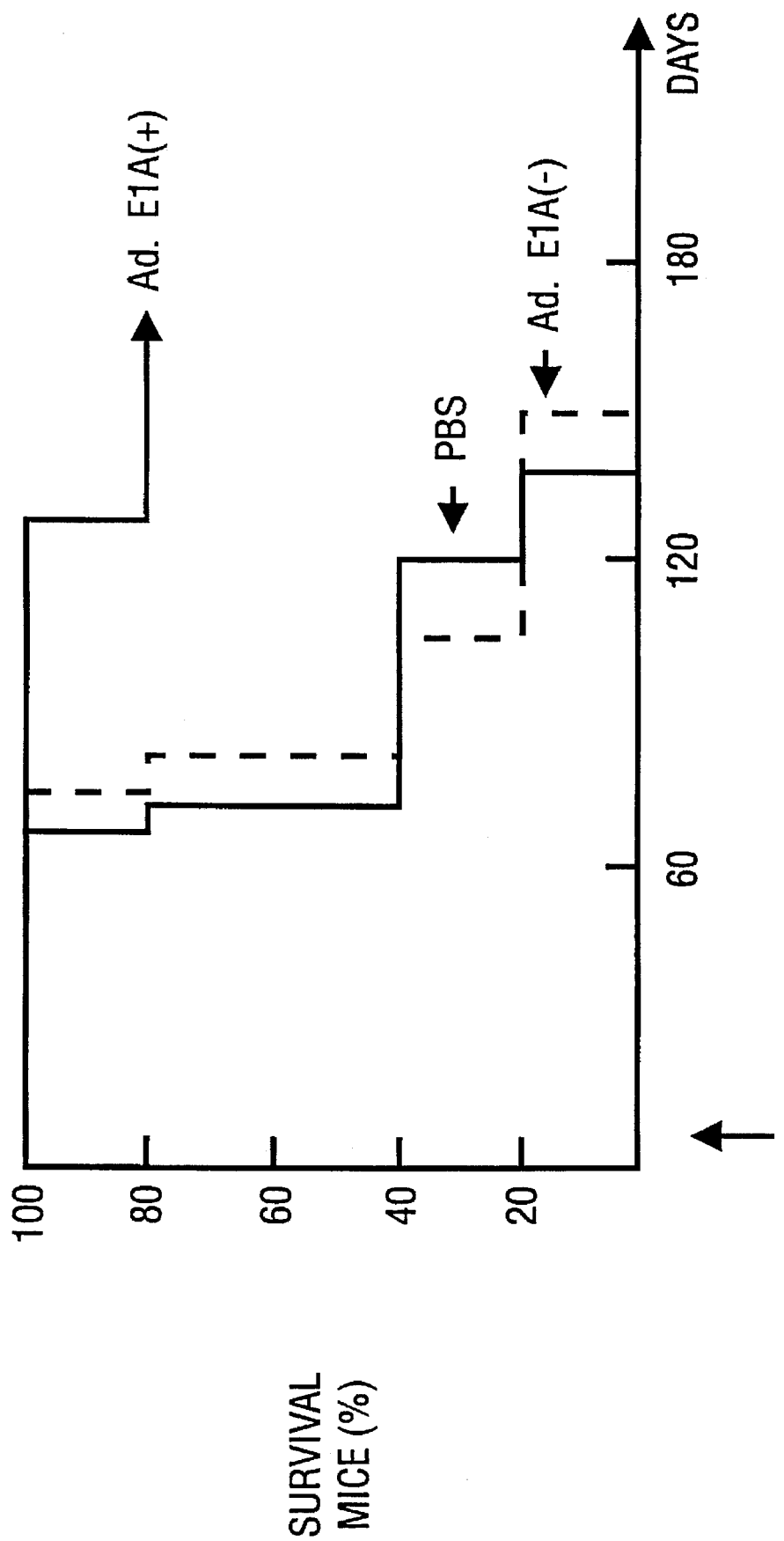
FIG. 25 shows the Ad. E1A therapeutic effect on ovarian cancer SK-OV-3(i.p.) SK-OV-3(i.p.) ($10^6$/mouse) were injected i.p. in female nu/nu mice. Five days later, mice were given i.p. injection of 0.1 ml of viral solution (titer: 2×$10^9$ PFU/ml) once/day for three days, then once/week for 4.5 months. The responses and survival rate were observed for more than one-half year (n=5).
Figure 26A:
FIGS. 26A and 26B show in vivo Ad. RSVβgal-mediated transfer of the lacZ gene to intraperitoneal SK-OV-3(i.p.), (FIG. 26A); and to intratracheal H820, (FIG. 26B).
Figure 26B:
Figure 28A:
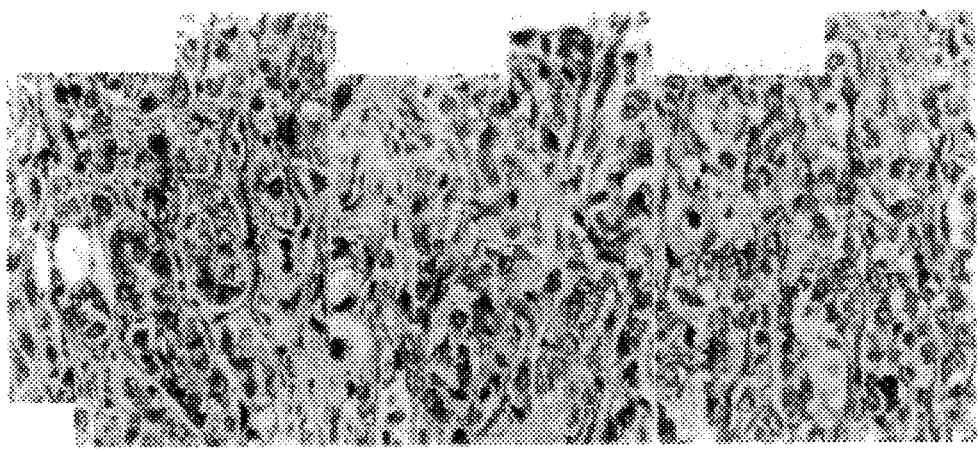
FIGS. 28A–28C show a histoimmunochemical analysis of representative histological sections of treated and control mice.
Figure 28B:
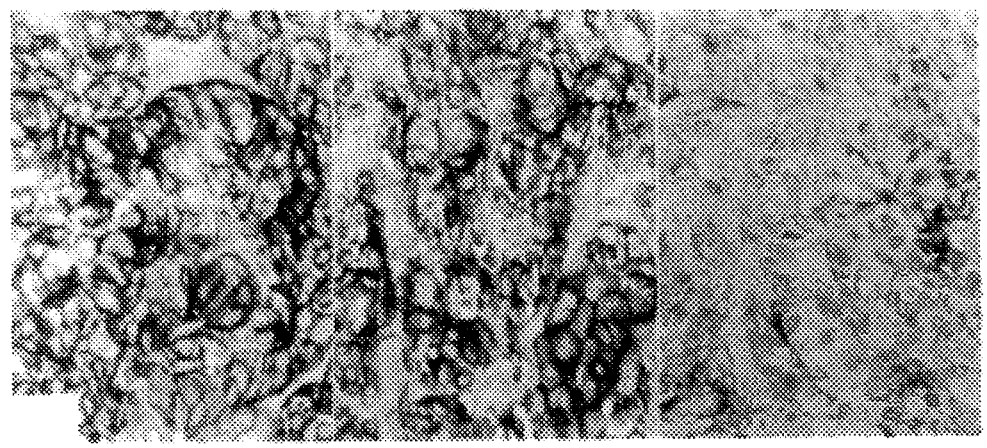
Figure 28C:
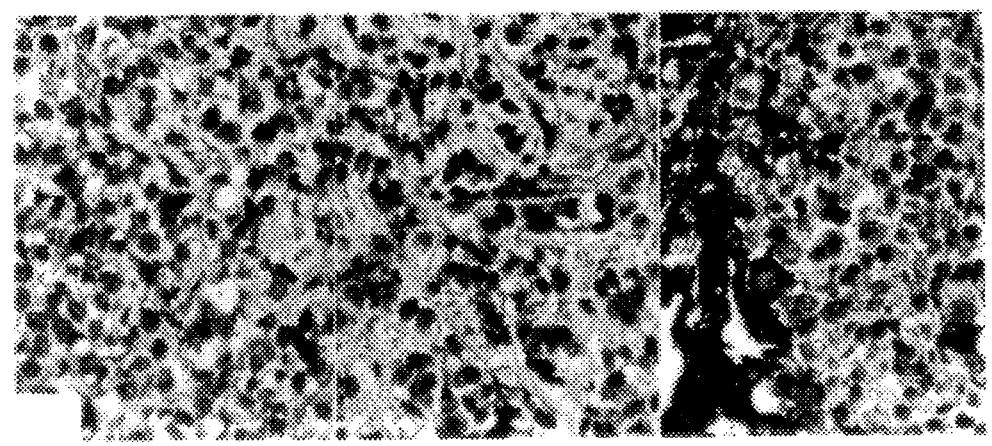

The present example provides for the transduction of replication-deficient adenovirus containing E1A gene [Ad.E1A(+)] into human cells in vitro and in vivo. Tumor suppressor gene E1A was efficiently transduced into human ovarian cancer cell SK-OV-3(i.p.) cells by Ad.E1A(+) in vitro and in vivo (FIG. 22 and FIGS. 26A and 26B). Up to 100% of the cells can be infected at either the virus/tumor ratio >50/1 or at lower ratios with multiple infections. Tumor growth in vitro (FIG. 23) and colony formation ability in soft agarose (FIG. 24) were greatly inhibited by Ad.E1A(+). SK-OV-3(i.p.) ($10^6$/mouse) was transplanted into the peritoneal cavity of nu/nu mice. Five days later they received an intraperitoneal injection of viral solution (titer: $2\times10^9$ PFU/ml) from either Ad.E1A(+), Ad.E1A (-), or Just PBS for 3 days, followed by once/week for 4.5 months. Clinical observation and survival rates showed that Ad.E1A(+) significantly prolonged the survival time of the mice and some mice were kept tumor free (FIG. 25). Histoimmunochemical analysis indicated that Ad.E1A protein was expressed in tumor tissue after gene delivery in vivo and expression of HER-2/neu P185 protein was greatly suppressed (FIGS. 28A–28C).

Figure 27:
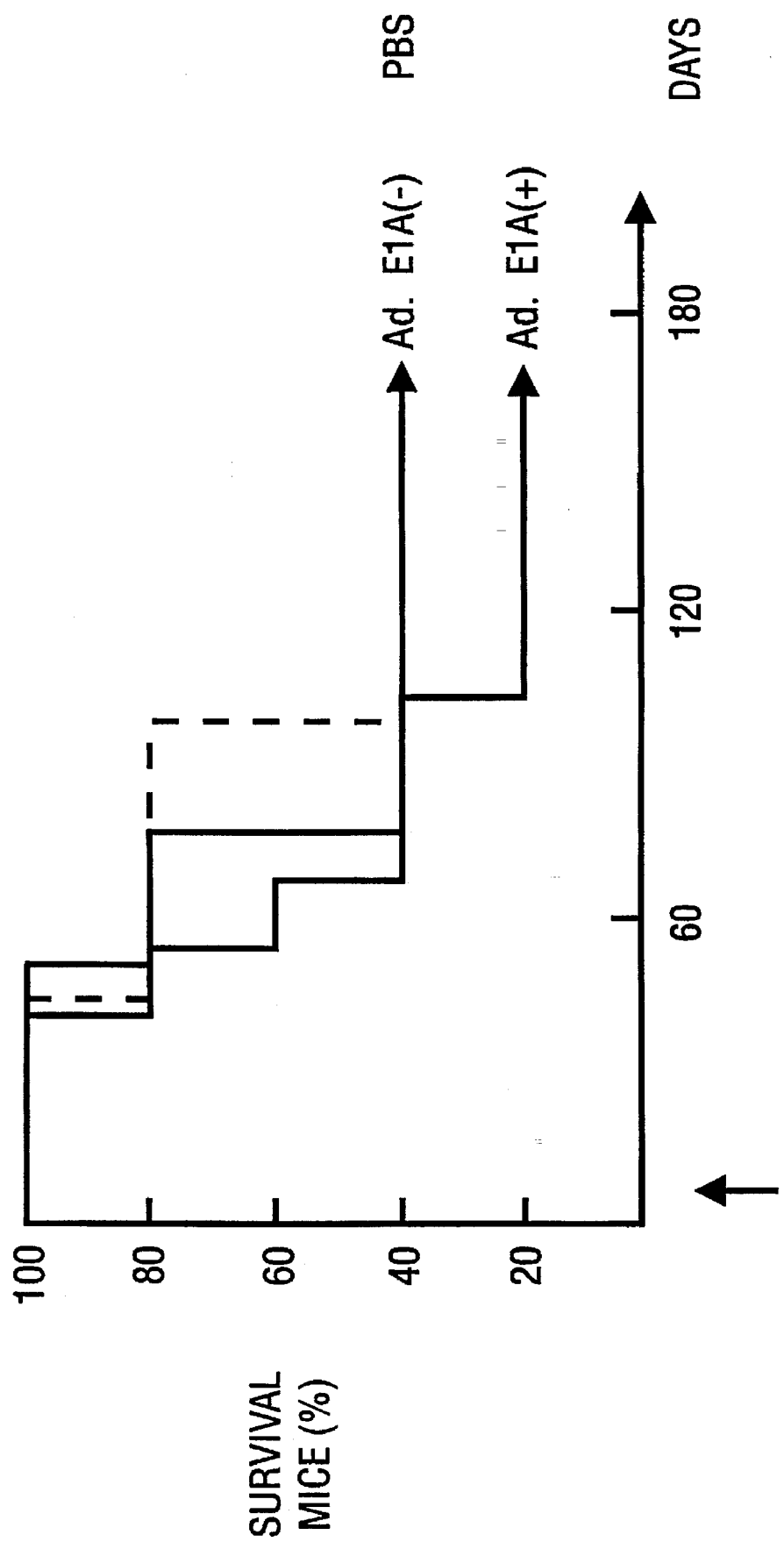
FIG. 27 shows the survival of mice bearing ovarian cancer 2774 after treatment by Ad.E1A. Human ovarian cancer cell line 2774 which has low level expression of HER-2/neu was injected i.p. into nu/nu mice (5×$10^5$/mouse). Five days later, mice were given i.p. injection of 0.1 ml of viral solution (titer: 2×$10^9$/ml) once/day for three days, then once/week for 4.5 months. The responses and survival rate were observed. AD.E1A(+) did not have significant therapeutic effect in 2774. Analysis of the results and the data of SK-OV-3(i.p.) which has high expression level of HER-2/neu indicate that AD.E1A(+) can specifically inhibit the growth of tumor which has high expression level of HER-2/neu.

The ovarian cancer cell line 2774, which has a very low level of expression of HER-2/neu P185 protein, was also tested for the therapeutic effect of Ad.E1A(+) (FIG. 27). Results showed that Ad.E1A(+) can not significantly prolong the survival rate of the 2774 cell line, indicating that Ad.E1A(+) specifically targets P185 high expression tumor cells.

Figure 29A:
FIGS. 29A–29C show representative mediastinal blocks of treated and control mice, see Table 3 for details. Arrow: Tumor.
Figure 29B:
Figure 29C:
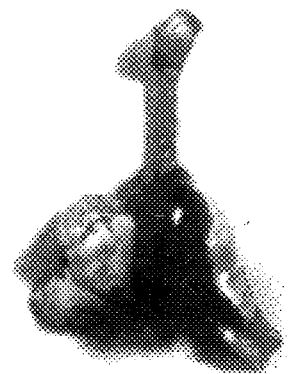

An orthotopic human lung cancer model in nu/nu mice was used to study the effect of Ad.E1A(+) on tumor growth of human lung cancer cell line NCI-H820 expressing a high level of P185 in vivo. Mouse tumor cells ($5\times10^6$), were inoculated intratracheally. Five days later, mice were treated by intratracheal instillation of viral solution (titer: $2\times10^9$ PFU/ml) of Ad.E1A(+), Ad.E1A(−), or PBS, followed by once/week i.v. injection treatment for 2.5 months. At autopsy, more than 80% of control mice but only 20% of treated mice had tumors as shown in Table 3 and FIGS. 29A–29C.

TABLE 3

THERAPEUTIC EFFECT OF Ad.E1A
ON LUNG CANCER H820 IN NU/NU MICE

|  | Ad.E1A(+) | Ad.E1A(−) | PBS |
|---|---|---|---|
| No. mice with tumor/total (%) | 1/5 (20%) | 4/5 (80%) | 5/5 (100%) |
| Mean volume + SD ($cm^3$) | 0.31 | 0.59 + 0.29 | 0.43 + 0.27 |

Human non-small cell lung cancer line NCI-H820 that has high expression of HER-2/neu was injected intratracheally into nu/nu mice ($5 \times 10^6$/mouse) via a tracheotomy incision. Five days later, the mice were treated once with intratracheal injection (0.1 ml) of either PBS, or Ad.E1A(−), Ad.E1A(+) (Viral titer: $2 \times 10^9$ PFU/ml), followed by weekly i.v. injection treatment for 2.5 months. Then, mediastinal blocks were removed and tumor volume was calculated. The results indicate that Ad.E1A(+) can prevent the growth of human lung cancer cells implanted orthotopically in nu/nu mice.

From the above data, it is clear that the adenoviral gene delivery system is effective and that Ad.E1A(+) has a therapeutic effect on HER-2/neu expressing human ovarian and lung cancer tumors.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for or teach methodology, techniques and/or compositions employed herein.

Adelman et al. (1983) DNA 2:183
Albini et al. (1987), Cancer Res., 47:3239.
Alley et al. (1988) Cancer Res., 48:589.
Anderson et al. (1979), Cell, 16:63.
Ausubel et al. (1987), Current Protocols in Molecular Biology Greene/Wiley-Interscience, New York.
Bargmann et al. (1986), Cell, 45:649.
Bargmann et al. (1986), Nature, 39:226.
Bargmann et al. (1986), Nature, 319:226–230.
Berchuck et al. (1990), Cancer Res., 50:4087–4091.
Berk et al. (1978), Cell, 14:695.
Berk, A. J. (1986), Ann. Rev. Genet., 20:45.
Borrelli et al. (1984) Nature, 312:608.
Campisi et al. (1983), Cell, 33:357.
Chang et al. (1989), J. Virol., 63:3479.
Chen et al. (1987), Mol. Cell. Biol., 7:2745–2752.
Chen et al. (1988), BioTechniques, 6:632.
Cherington et al. (1988), Mol. Cell. Biol., 8:1380–1384.
Cook & Lewis (1984), Science, 224:612–615.

Cook et al. (1989), *J. Immunol.*, 142:4527–4534.
Coussens et al. (1985), *Science*, 230:1132.
Crea et al. (1978), *Proc. Natl. Acad. Sci. U.S.A* 75:5765
DeCaprio et al. (1988), 54:275–283.
Dobashi et al. (1991), *Proc. Natl. Acad. Sci. USA*, 88:8582–8586.
Downward et al. (1984), *Nature* (London), 307:521.
Dynlacht et al. (1991), *Cell*, 66:563–576.
Eichenlaub, R. (1979), *J. Bacteriol* 138:559–566
Evan et al. (1992), *Cell*, 69:119–128.
Fiers et al. (1978), *Nature* 273:113.
Figge et al. (1988), *Nature* (London), 334:109.
Figge et al. (1988), *J. Virol.*, 62:1814–1818.
Frisch, S. M. (1991), *Proc. Natl. Acad. Sci. USA*, 88:9077–9081.
Gao et al., (1991), *Biochemical and Biophysical Research Communications*, 179(1):280–285.
Gorman et al. (1982), *Mol. Cell. Biol.*, 2:1044–1051.
Gribskov et al. (1986), *Nucl. Acids Res.*, 14:6745.
Haley et al. (1984), *Proc. Natl. Acad. Sci. USA*, 81:5734.
Harlow et al. (1985), *J. Virol.*, 55:533).
Hearing et al. (1985), *Mol. Cell. Biol.*, 5:3214.
Hen et al. (1985), *Science*, 230:1391.
Holmes et al. (1992), *Science*, 256:1205–1210.
Hopp, U.S. Pat. No. 4,554,101
Houweling et al. (1980), *Virology*, 105:537.
Hung et al. (1986), *Proc. Natl. Acad. Sci. USA*, 83:261–264.
Huang & Huang, (1992), *J. Biol. Chem.*, 267:11508–11512.
Hung, M-C (1988), *The Cancer Bull.*, 40:300–303.
Hung et al. (1989), *Proc. Natl. Acad. Sci. USA*, 86:2545–2548.
Hung et al. (1992), *Cancer Letters*, 61:95–103.
Johnson et al. (1988), *J. Biol. Chem.*, 263:5693–5699.
Kalderon et al. (1984), *Virology*, 139:109–137.
Kern et al. (1990), *Cancer Res.*, 50:5184–5191.
King et al. (1985), *Science*, 229:974–976.
Kraus et al. (1987), *EMBO J.*, 6:605.
Kyte & Doolittle, *J. Mol. Biol.*, 157:105–132, 1982.
Land et al. (1983), *Science*, 222:771.
Land et al. (1983), *Nature*, 304:596–602.
Lillie et al. (1989), *Nature* (London), 338:39.
Liotta, L. A. (1989), in *Influence of Tumor Development on the Host*, 7:58–71, Kluwer Academic Publishers, Dordrecht.
Livingston et al. (1987), *Mol. Biol. Med.*, 4:63–80.
Lupu et al. (1990), *Science*, 249:1552.
Matin et al. (1989), *Oncogene*, 5:111.
Matin et al. (1990), *Oncogene*, 5:111–116.
Messing et al. (1981) Third Cleveland Symposium on Macromolecules and Recombinant DNA, Editor A. Walton, Elsevier, Amsterdam
Mitchell et al. (1987), *Cell*, 50:847–861.
Mitchell et al. (1989), *Science*, 245:371.
Moran et al. (1987), *Cell*, 48:177.
Morgenstern et al. (1990), *Nucleic Acids Res.*, 18:3587–3596.
Muller et al. (1982), *Nature* (London), 299:640.
Muro-cacho, C. A. (1992), *J. of Immunotherapy*, 11:231–237.
Nabel et al. (1990), *Science*, 249:1285–1288.
Needleman et al. (1970), *J. Mol. Biol.*, 48:443.
Nelson et al. (1990), *Proc. Natl. Acad. Sci. USA*, 87:8041–8045.
Nicolau et al. (1983), *Biol. Cell*, 47:121–130.
Nicolau et al. (1987), *Methods in Enzymology*, 149:157–176.
Padhy et al. (1982), *Cell*, 28:865–871.
Peles et al. (1992), *Cell*, 69:205–216.
Pozzatti et al. (1988), *Mol. Cell. Biol.*, 8:2984.
Rao et al. (1992), *Proc. Natl. Acad. Sci. USA*, 89:7742–7746.
Reddy et al. (1978), *Science*, 200:494.
Repesh, L. A. (1989), *Invasion and Metastasis*, 9:192.
Robert et al. (1985), *J. Virol.*, 56:404.
Ruley, H. E. (1985), *Nature*(London), 304:602.
Rustgi et al. (1991), *Nature*, 352:541–544.
Sassone-Corsi et al. (1987), *Proc. Natl. Acad. Sci, USA*, 84:6430.
Sawada et al. (1985), *Virology*, 147:413–421.
Schechter et al. (1984), *Nature* (London), 312:513.
Schechter et al. (1985), *Science*, 229:976–978.
Schneider et al. (1989), *Cancer Res.*, 49:4968–4971.
Schwartz et al., eds. (1979), *Atlas of Protein Sequence and Structure*, National Biomedical Research Foundation, pgs. 353–358.
Senba et al. (1985), *Proc. Natl. Acad. Sci. USA*, 82:6497.
Seidman et al. (1985), *Gene*, 38:233–237.
Shih et al. (1981), *Nature* (London), 290:261–264.
Slamon et al. (1987), *Science*, 235:177–182.
Slamon et al. (1989), *Science*, 244:707–712.
Smith et al. (1981), *Adv. Appl. Math.*, 2:482.
Southern et al. (1982), *J. Mol. Appl. Genet.*, 1:327.
Steeg et al. (1988), *Cancer Res.*, 48:6550–6554.
Stein et al. (1987), *Mol. Cell. Biol.*, 7:1164.
Suen et al. (1990), *Mol. Cell. Biol.*, 10:6306–6315.
Suen et al. (1991), *Mol. Cell. Biol.*, 11:354–362.
Sullenger et al. (1990), *Mol. Cell. Biol.*, 10:6512–23.
Tal et al. (1987), *Mol. Cell. Biol.*, 7:2597.
Tooze, J. (1981), *Molecular Biology of Tumor Viruses*, Part 2, 2d ed. Cold Spring Harbor Laboratory, Cold Spring Harbor, N.Y.
Towbin et al. (1979), *Proc. Natl. Acad. Sci., USA*, 76:4350.
Van Dam et al. (1989), *Oncogene*, 4:1207.
Velcich et al. (1986), *Mol. Cell. Biol.*, 6:4019.
Wallich et al. (1985), *Nature* (London), 315:301.
Wang et al. (1991), *Mol. Cell. Biol.*, 11:4253–4265.
Weinberg, R. A. (1985), *Science*, 230:770–776.
Weiner et al. (1990), *Cancer Res.*, 50:421–425.
Wen et al. (1992), *Cell*, 69:559–572.
Wexler, H. (1966), *J. Natl. Cancer. Inst.*, 36:641.
Whyte et al. (1988), *Nature* (London), 334:124–129.
Whyte et al. (1989), *Cell*, 56:67.
Yamamoto et al. (1986), *Nature* (London), 319:230.
Yan et al. (1991), *Oncogene*, 6:343–345.
Yanisch-Perron et al. (1985), *Gene*, 33:103–109.
Yarden et al. (1989), *Proc. Natl. Acad. Sci, USA*, 86:3179.
Yarden & Peles (1991), *Biochemistry*, 30:3543–3550.
Yokota et al. (1986), *Lancet*, i:765–767.
Yokota et al. (1988), *Oncogene*, 2:283–287.
Yu et al. (1990), *Proc. Natl. Acad. Sci. USA*, 87:4499–4503.
Yu et al. (1991), *Oncogene*, 6:1991–1996.
Yu et al. (1992), *J. Biol. Chem.*, 267:10203–10206.
Yu et al. (1992), *Oncogene*, 7:2263–2270.
Yu et al. (1993), *Cancer Res.*, 53:891–898.
Zhang et al. (1989), *Oncogene*, 4:985–989.

What is claimed is:

1. A method to suppress the growth of a neu oncogene-mediated tumor in a mammal, said method comprising introducing to a cell of a tumor an adenovirus containing an adenoviral E1A gene operatively linked to a promoter, wherein the production of the E1A gene product results in a decrease in the growth rate of said tumor.

2. The method of claim 1, wherein the adenovirus is a replication-deficient adenovirus.

3. The method of claim 2, wherein the replication deficient adenovirus is the Ad.E1A(+) adenovirus.

4. The method of claim 1, wherein the E 1A gene product comprises the E 1A 12S or 13S gene product.

5. The method of claim 4, wherein the E1A gene encodes either the E 1A 12S or 13S gene product.

6. The method of claim 4, wherein the E 1A gene encodes both the E1A 12S and 13S gene products.

7. The method of claim 1, wherein the mammal is a human.

8. The method of claim 1, wherein the tumor is a breast tumor.

9. The method of claim 1, wherein the tumor is an ovarian tumor.

10. The method of claim 1, wherein the tumor is a lung tumor.

11. The method of claim 1, further comprising introducing to a tumor an SV40 large T antigen (LT) via either a vector comprising a nucleic acid encoding an SV40 large T antigen (LT) gene product operatively linked to a promoter or a liposome complexed to a nucleic acid encoding an SV40 large T antigen (LT) gene product operatively linked to a promoter, wherein the LT gene product is produced in said tumor.

12. The method of claim 11, wherein the LT gene product is a nontransforming LT mutant.

13. The method of claim 12, wherein the nontransforming mutant is K1.

14. The method of claim 11, wherein the the introduction of the SV40 large T antigen is via a vector comprising a nucleic acid encoding an SV40 large T antigen (LT) gene product operatively linked to a promoter.

15. The method of claim 14, wherein the vector is a viral vector.

16. The method of claim 15, wherein the viral vector is an adenoviral vector.

17. The method of claim 15, wherein the vector is a retroviral vector.

18. The method of claim 14, wherein the vector is a plasmid vector.

19. The method of claim 18, wherein the plasmid vector is pZ189, pVO-0, pK1, or pK7.

20. The method of claim 11, wherein wherein the the introduction of the SV40 large T antigen is via a liposome complexed to a nucleic acid encoding an SV40 large T antigen (LT) gene product operatively linked to a promoter.

21. A method of providing an adenovirus E1A gene product to a neu oncogene-mediated tumor in a mammal, the method comprising introducing to said tumor an adenovirus containing an adenoviral E1A gene operatively linked to a promoter, wherein expression of the E1A gene results in regression said tumors.

22. A method to suppress the growth of a neu oncogene-mediated tumor in a mammal, the method comprising introducing to said tumor an adenovirus containing an adenoviral E1A gene operatively linked to a promoter, wherein the production of the E1A gene product results in a decrease in the growth rate of said tumor.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "DNA"

( x i ) SEQUENCE DESCRIPTION: SEQ ID NO:1:

TCTTGCTGGA ATGCAGTTGG 20